United States Patent
Shinde et al.

(10) Patent No.: US 11,140,899 B2
(45) Date of Patent: Oct. 12, 2021

(54) METHODS OF PLANT ENHANCEMENT WITH MICROALGAE BIOMASS

(71) Applicant: HELIAE DEVELOPMENT, LLC, Gilbert, AZ (US)

(72) Inventors: Sandip Shinde, Gilbert, AZ (US); Manakandadas Mathilakathu Madathil, Gilbert, AZ (US); Michael Warner, Phoenix, AZ (US); Stephen Ventre, Mesa, AZ (US); Laura Carney, CHadler, AZ (US); Michael Miller, Chandler, AZ (US); Ganapathy Chellapan, Naperville, IL (US); Jon Hansen, Gilbert, AZ (US); Michael Lamont, Gilbert, AZ (US)

(73) Assignee: Heliae Development, LLC, Gilbert, AZ (US)

(*) Notice: Subject to any disclaimer, the term of this patent is extended or adjusted under 35 U.S.C. 154(b) by 190 days.

(21) Appl. No.: 16/333,593

(22) PCT Filed: Jun. 16, 2017

(86) PCT No.: PCT/US2017/037880
§ 371 (c)(1),
(2) Date: Mar. 14, 2019

(87) PCT Pub. No.: WO2018/052502
PCT Pub. Date: Mar. 22, 2018

(65) Prior Publication Data
US 2020/0267995 A1    Aug. 27, 2020

Related U.S. Application Data

(60) Provisional application No. 62/462,654, filed on Feb. 23, 2017, provisional application No. 62/410,931, filed on Oct. 21, 2016, provisional application No. 62/395,178, filed on Sep. 15, 2016.

(51) Int. Cl.
*A01N 65/03* (2009.01)
*A01N 37/46* (2006.01)
*C12P 19/04* (2006.01)

(52) U.S. Cl.
CPC ............ *A01N 37/46* (2013.01); *A01N 65/03* (2013.01); *C12P 19/04* (2013.01)

(58) Field of Classification Search
None
See application file for complete search history.

(56) References Cited

U.S. PATENT DOCUMENTS

| 10,517,303 B2* | 12/2019 | Shinde ............ A01N 65/03 |
| 2004/0049062 A1 | 3/2004 | Bijl |
| 2019/0008157 A1* | 1/2019 | Shinde ............ A01N 63/00 |
| 2019/0289857 A1* | 9/2019 | Shinde ............ A01N 65/03 |
| 2020/0060283 A1* | 2/2020 | Shinde ............ A01N 65/03 |

OTHER PUBLICATIONS

Wuang, S. et al. Use of Spriulina Biomass Produced from Treatment of Aquaculture Wastewater as Agricultural Fertilizers. Algal Research 15:59-64, 2016. (Year: 2016).*
Uysal O. et al. Evaluation of Microalgae as Microbial Fertilizer. European J of Sustainable Development 4(2)77-82, 2015. (Year: 2015).*
Bileva, "Influence of Green Algae Chlorella Bulgaris on Infested with Xiphinema Index Grape Seedinglins". J Earth Sci Climate Change, Apr. 30, 2013 (Apr. 30, 2013), vol. 4(2) p. 1, col. 2 Para [2]; p. 1, col. 2, para [3]; p. 2, col. 1 full para [5]; pag 2, col. 2 Table 2: Fig 1; p. 3, col. 1, bullespoint 1-3.
Garia-Gonzalez, et al. "Biofertilizer and Biostimulant properties of the microalga Acutodesmus dimorphus". J Aply Pycol; May 29, 2015, vol. 28, p. 1051-1061, p. 1051, col. 1, Abstract; p. 1052, col. 2, full para [4] p. 1053, col. 3, full para [3]; p. 1052, col. 2, para [2].
Hernandez-Herrera et al. "Effect of liquid seaweed extracts on growth of tomato seedings (Solanum lycopersicum L)". J Apply Phycol, Jul. 17, 2013, vol. 26 (1), p. 1. col. 1 Abstract; p. 2, col. 2, full para [1]; p. 3, col. 2, full page [2], p. 3, col. 2, full para [4]; p. 6, col. 2 full para [3].
Batacharyya et al. "Seaweed extracts as Biostimulants in Horticulture", Sci Hortic, Nov. 30, 2015, vol. 196, p. 39-48, (p. 1, Abstract).
International Search Report for PCT/US2017/37880 dated Sep. 12, 2017.

* cited by examiner

*Primary Examiner* — Ralph J Gitomer
(74) *Attorney, Agent, or Firm* — Heliae Development, LLC; Adam Lunceford; Veronica-Adele R. Cao

(57) ABSTRACT

The invention relates to methods of plant enhancement comprising administration of a composition comprising microalgae biomass to improve seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot,-fruit quality, flowering, or sunburn.

18 Claims, 6 Drawing Sheets

METHODS OF PLANT ENHANCEMENT WITH MICROALGAE BIOMASS

CROSS REFERENCE TO RELATED APPLICATIONS

The present application is a U.S. National Stage entry under 35 U.S.C. § 371 of International Application No. PCT/2017/37880, filed on Jun. 16, 2017, designating the United States of America and published in English on Mar. 22, 2018, which in turn claims priority to U.S. Provisional Application No. 62/395,178, filed Sep. 15, 2016, entitled Microalgae Based Composition for Benefiting Plants and Methods of Application; U.S. Provisional Application No. 62/410,931, filed Oct. 21, 2016, entitled Microalgae Based Compositions for Benefiting Plants and Methods of Application and U.S. Provisional Application No. 62/462,654, filed Feb. 23, 2017, entitled Microalgae Based Compositions for Benefiting Plants and Methods of Application. The entire contents of all of the foregoing are hereby incorporated by reference herein.

BACKGROUND

Seed emergence occurs as an immature plant breaks out of its seed coat, typically followed by the rising of a stem out of the soil. The first leaves that appear on many seedlings are the so-called seed leaves, or cotyledons, which often bear little resemblance to the later leaves. Shortly after the first true leaves, which are more or less typical of the plant, appear, the cotyledons will drop off. Germination of seeds is a complex physiological process triggered by imbibition of water after possible dormancy mechanisms have been released by appropriate triggers. Under favorable conditions rapid expansion growth of the embryo culminates in rupture of the covering layers and emergence of the radicle. A number of agents have been proposed as modulators of seed emergence. Temperature and moisture modulation are common methods of affecting seed emergence. Addition of nutrients to the soil has also been proposed to promote emergence of seeds of certain plants.

Additionally, whether at a commercial or home garden scale, growers are constantly striving to optimize the yield and quality of a crop to ensure a high return on the investment made in every growth season. As the population increases and the demand for raw plant materials goes up for the food and renewable technologies markets, the importance of efficient agricultural production intensifies. The influence of the environment on a plant's health and production has resulted in a need for strategies during the growth season which allow the plants to compensate for the influence of the environment and maximize production. Addition of nutrients to the soil or application to the foliage has been proposed to promote yield and quality in certain plants. The effectiveness can be attributable to the ingredients or the method of preparing the product. Increasing the effectiveness of a product can reduce the amount of the product needed and increase efficiency of the agricultural process. Therefore, there is a need in the art for methods of enhancing the yield and quality of a plant.

SUMMARY

Compositions and methods are described herein improving at least one plant characteristic. The compositions can include cells (i.e., biomass) or extracts from the microalgae in various states, such as but not limited to, cells with reduced protein content, whole cells, lysed cells, dried cells, excreted products (e.g., excreted polysaccharides [EPS]), extracted oil, extracted protein, cells that have been subjected to an oil or protein extraction process, and combinations thereof. The composition can include microalgae derived products as the primary or sole active ingredient, or in combination with other active ingredients such as, but not limited to, extracts or biomass from macroalgae. The compositions can be in the form of a liquid or dry form (powder, or the like). The compositions can be stabilized through the addition of stabilizers suitable for plants, pasteurization, and combinations thereof. The methods can include applying the compositions to plants or seeds in a variety of methods, such as but not limited to, soil application, foliar application, seed treatments (such as seed coating), and/or hydroponic application. The methods can include single or multiple applications of the compositions, and can also include low concentrations of microalgae cells (i.e., biomass), excreted products, or extracts.

In one non-limiting embodiment, a method of plant enhancement can include administering to a plant, seedling, or seed a composition treatment comprising 0.001-0.1% by weight of microalgae biomass to enhance at least one plant characteristic, which in some embodiments is whole microalgae biomass. "Whole microalgae biomass" means a composition wherein substantially all of the components of the microalgae cells produced in the composition during culturing/growth remain present (e.g., in certain aspects of the invention at least about 90% of the cellular components, at least about 95% of the cellular components, or at least about 99% of the cellular components produced during growth/culturing remain present). This kind of composition ("whole microalge biomass") is distinct from, for example, a composition formed from an extract taken from a microalgae composition, which might be composed primarily or entirely of one or more microalgae-derived oils or proteins.

"Microalgae biomass" means any composition wherein a majority of the cellular components of the whole microalgae biomass are maintained in the composition (by number of components, but not necessarily by weight). Thus, for example, a collection of microalgae cells that is subjected to an oil extraction would be considered microalgae biomass, but not be considered whole microalgae biomass. A microalgae biomass subjected to processing to remove one or more of its cellular components also may be referred to as a "post-extracton microalgae biomass".

In some embodiments, the composition can be applied when the plant is under at least one of salt stress and temperature stress conditions. In some embodiments, the microalgae biomass can have been subjected to a protein extraction process. In some embodiments, the microalgae biomass can have been subjected to an oil extraction process. In some embodiments, the microalgae can include at least one from the group consisting of *Botryococcus, Scenedesmus, Pavlova, Phaeodactylum, Nannochloropsis, Spirulina, Galdieria, Haematococcus, Isochrysis, Porphyridium, Schizochytrium*, and *Tetraselmis*.

In another non-limiting embodiment, a composition can include microalgae biomass, in a concentration in the range of 0.001-0.1% by weight.

In another non-limiting embodiment, a method of preparing a composition can include diluting the concentration of microalgae biomass to a concentration in the range of 0.001-0.1% by weight.

In another non-limiting embodiment, a method of preparing a composition can include: subjecting microalgae cells to an oil extraction process; separating the extracted oil from the extracted biomass; and diluting the concentration of extracted biomass to a concentration in the range of 0.001-0.1% by weight.

In one non-limiting embodiment, a method of plant enhancement can include administering to a plant, seedling, or seed a composition treatment comprising 0.0001-0.01% by weight of extracted microalgae oil to enhance at least one plant characteristic. In some embodiments, the composition can be applied when the plant is under at least one of salt stress and temperature stress conditions. In some embodiments, the microalgae cells can have a low protein content. In some embodiments, the microalgae can include at least one from the group consisting of *Botryococcus, Scenedesmus, Pavlova, Phaeodactylum, Spirulina, Galdieria, Chlorella, Haematococcus, Isochrysis, Nannochloropsis, Porphyridium, Schizochytrium*, and *Tetraselmis*.

In another non-limiting embodiment, a composition can include extracted microalgae oil, in a concentration in the range of 0.0001-0.01% by weight.

In another non-limiting embodiment, a method of preparing a composition can include: subjecting microalgae cells to an oil extraction process; separating the extracted oil from the extracted biomass; and diluting the concentration of extracted oil to a concentration in the range of 0.0001-0.01% by weight.

In one non-limiting embodiment, a method of plant enhancement can include administering to a plant, seedling, or seed a composition treatment comprising 0.001-0.1% by weight of extracted microalgae protein from at least one from the group consisting of *Galdieria, Porphyridium*, and *Spirulina*.to enhance at least one plant characteristic. In some embodiments, the composition can be applied when the plant is under at least one of salt stress and temperature stress conditions.

In another non-limiting embodiment, a composition can include extracted microalgae protein, in a concentration in the range of 0.001-0.1% by weight.

In another non-limiting embodiment, a method of preparing a composition can include: subjecting microalgae cells to a protein extraction process; separating the extracted protein fraction; and diluting the concentration of extracted protein fraction to a concentration in the range of 0.001-0.1% by weight.

In one non-limiting embodiment, a method of plant enhancement can include administering to a plant, seedling, or seed a composition treatment comprising 0.001-0.1% by weight of EPS from *Porphyridium* to enhance at least one plant characteristic. In some embodiments, the composition can be applied when the plant is under at least one of salt stress and temperature stress conditions.

In another non-limiting embodiment, a composition can include EPS from *Porphyridium*, in a concentration in the range of 0.001-0.1% by weight.

In another non-limiting embodiment, a method of preparing a composition can include: isolating EPS from a culture of *Porphyridium*; and diluting the concentration of isolated EPS to a concentration in the range of 0.001-0.1% by weight.

In another non-limiting embodiment, a method of plant enhancement can include administering to a plant, seedling, or a seed a composition treatment comprising 10% by weigh of microalgae biomass to soil at an application rate in the range of 2-20 liters per acre to enhance at least one plant characteristic. In some embodiments, the application rate can be in the range of 3.7 to 15 liters per acre. In some embodiments, the microalgae can include at least one from the group consisting of *Aurantiochytrium, Spirulina, Isochrysis*, and *Scenedesmus*.

DETAILED DESCRIPTION

Figure 1:
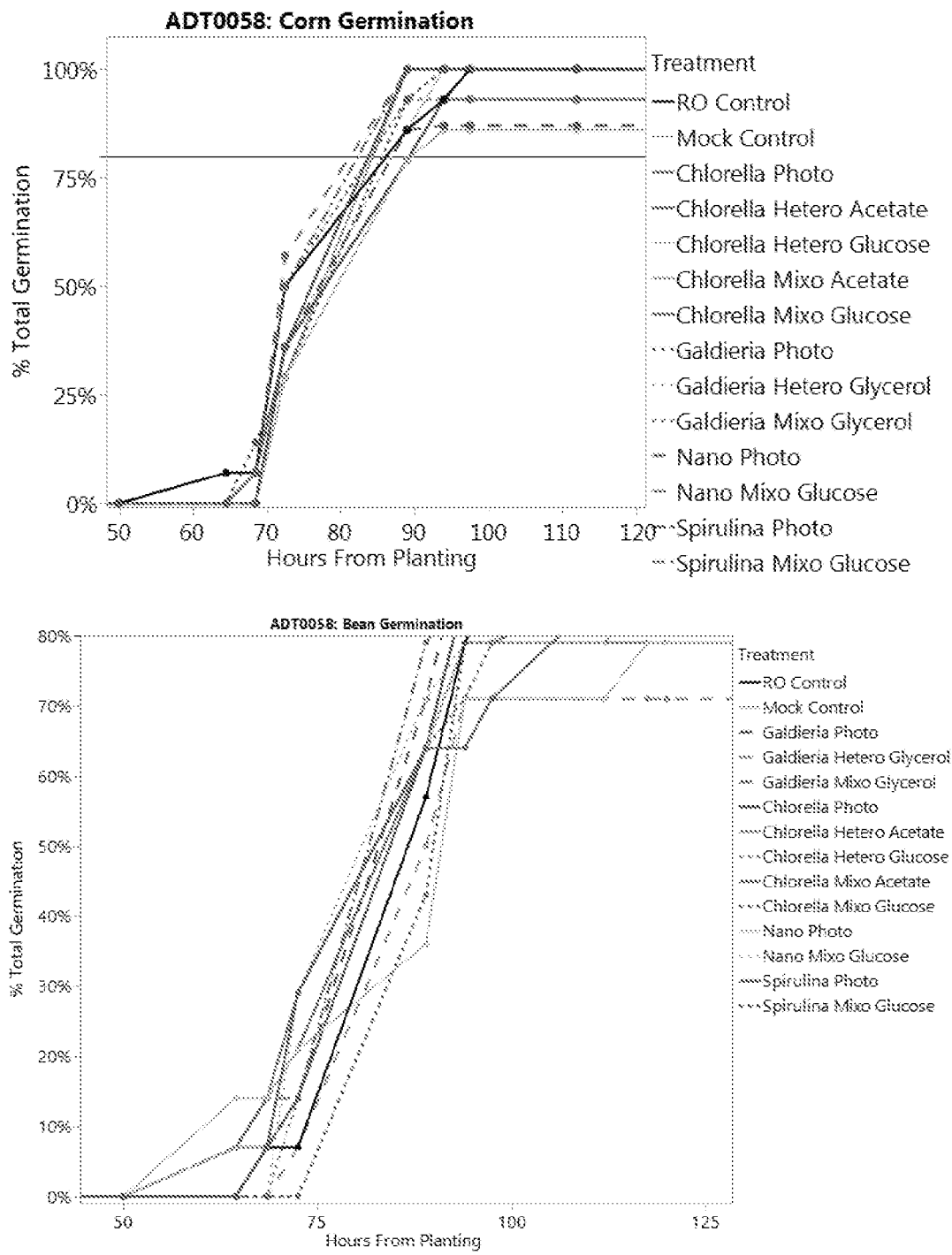
FIG. 1 depicts results of experiments involving microalgae-based compositions on corn, bean and pepper seed germination.
Figure 1:
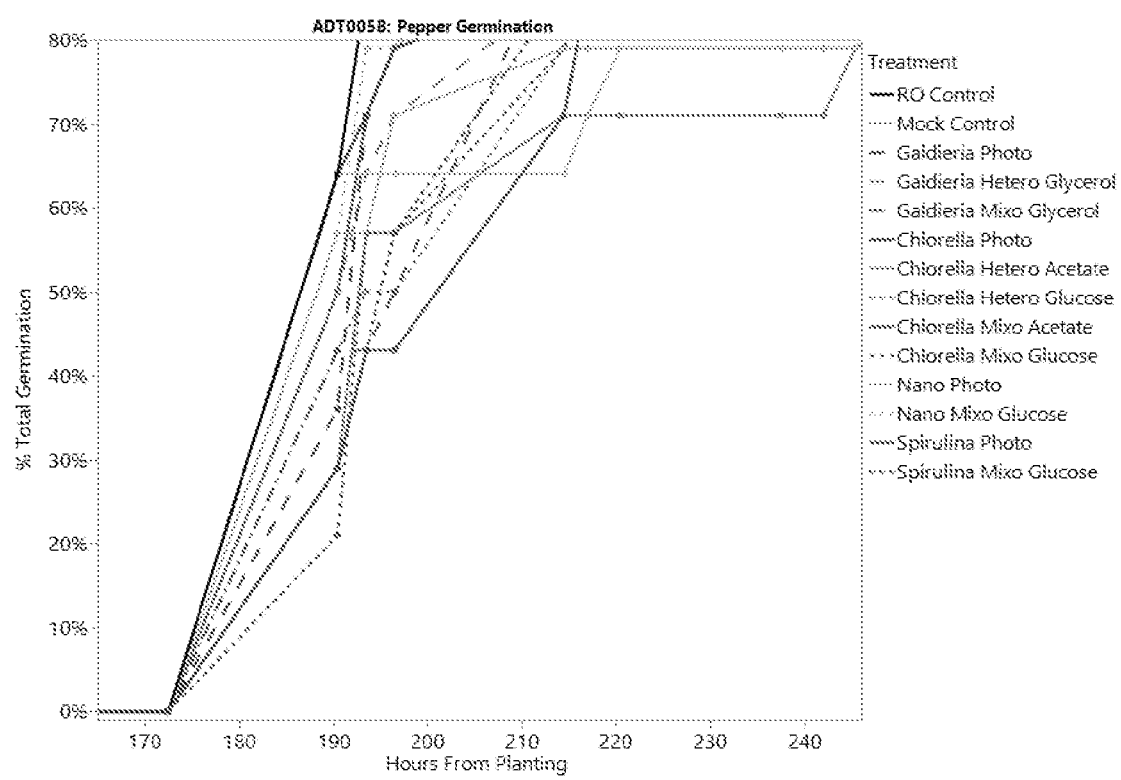

Many plants can benefit from the application of liquid compositions that provide a bio-stimulatory effect. Non-limiting examples of plant families that can benefit from such compositions include plants from the following: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Piperaceae, and Proteaceae.

The Solanaceae plant family includes a large number of agricultural crops, medicinal plants, spices, and ornamentals in it's over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding *Antarctica*, and thus have a widespread importance in agriculture across the globe.

The Fabaceae plant family (also known as the Leguminosae) comprises the third largest plant family with over 18,000 species, including a number of important agricultural and food plants. Taxonomically classified in the Plantae kingdom, Tracheobionta (subkingdom), Spermatophyta (superdivision), Magnoliophyta (division), Manoliopsida (class), Rosidae (subclass), and Fabales (order), the Fabaceae family includes, but is not limited to, soybeans, beans, green beans, peas, chickpeas, alfalfa, peanuts, sweet peas, carob, and liquorice. Plants in the Fabaceae family can range in size and type, including but not limited to, trees, small annual herbs, shrubs, and vines, and typically develop legumes. Plants in the Fabaceae family can be found on all the continents, excluding *Antarctica*, and thus have a widespread importance in agriculture across the globe. Besides food, plants in the Fabaceae family can be used to produce natural gums, dyes, and ornamentals.

The Poaceae plant family supplies food, building materials, and feedstock for fuel processing. Taxonomically classified in the Plantae kingdom, Tracheobionta (subkingdom), Spermatophyta (superdivision), Magnoliophyta (division), Liliopsida (class), Commelinidae (subclass), and Cyperales (order), the Poaceae family includes, but is not limited to, flowering plants, grasses, and cereal crops such as barely, corn, lemongrass, millet, oat, rye, rice, wheat, sugarcane, and sorghum. Types of turf grass found in Arizona include, but are not limited to, hybrid Bermuda grasses (e.g., 328 tifgrn, 419 tifway, tif sport).

The Rosaceae plant family includes flowering plants, herbs, shrubs, and trees. Taxonomically classified in the Plantae kingdom, Tracheobionta (subkingdom), Spermatophyta (superdivision), Magnoliophyta (division), Magnoliopsida (class), Rosidae (subclass), and Rosales (order), the Rosaceae family includes, but is not limited to, almond, apple, apricot, blackberry, cherry, nectarine, peach, plum, raspberry, strawberry, and quince.

The Vitaceae plant family includes flowering plants and vines. Taxonomically classified in the Plantae kingdom, Tracheobionta (subkingdom), Spermatophyta (superdivision), Magnoliophyta (division), Magnoliopsida (class), Rosidae (subclass), and Rhammales (order), the Vitaceae family includes, but is not limited to, grapes.

Particularly important in the production of fruit from plants is the beginning stage of growth where the plant emerges and matures into establishment. A method of treating a seed, seedling, or plant to directly improve the germination, emergence, and maturation of the plant; or to indirectly enhance the microbial soil community surrounding the seed or seedling is therefore valuable starting the plant on the path to marketable production. The standard typically used for assessing emergence is the achievement of the hypocotyl stage, where a stem is visibly protruding from the soil. The standard typically used for assessing maturation is the achievement of the cotyledon stage, where two leaves visibly form on the emerged stem.

Also important in the production of fruit from plants is the yield and quality of fruit, which can be quantified as the number, weight, color, firmness, ripeness, moisture, degree of insect infestation, degree of disease or rot, and degree of sunburn of the fruit. A method of treating a plant to directly improve the characteristics of the plant, or to indirectly enhance the chlorophyll level of the plant for photosynthetic capabilities and health of the plant's leaves, roots, and shoot to enable robust production of fruit is therefore valuable in increasing the efficiency of marketable production. Marketable and unmarketable designations can apply to both the plant and fruit, and can be defined differently based on the end use of the product, such as but not limited to, fresh market produce and processing for inclusion as an ingredient in a composition. The marketable determination can assess such qualities as, but not limited to, color, insect damage, blossom end rot, softness, and sunburn. The term total production can incorporate both marketable and unmarketable plants and fruit. The ratio of marketable plants or fruit to unmarketable plants or fruit can be referred to as utilization and expressed as a percentage. The utilization can be used as an indicator of the efficiency of the agricultural process as it shows the successful production of marketable plants or fruit, which will be obtain the highest financial return for the grower, whereas total production will not provide such an indication.

To achieve such improvements in emergence, maturation, and yield of plants, a method to treat such seeds and plants, and soil with a low concentration microalgae based composition, in a dried or liquid solution form was developed. Microalgae can be grown in heterotrophic, mixotrophic, and phototrophic conditions. Culturing microalgae in heterotrophic conditions comprises supplying organic carbon (e.g., acetic acid, acetate, glucose) to cells in an aqueous culture medium comprising trace metals and nutrients (e.g., nitrogen, phosphorus). Culturing microalgae in mixotrophic conditions comprises supplying light and organic carbon (e.g., acetic acid, acetate, glucose) to cells in an aqueous culture medium comprising trace metals and nutrients (e.g., nitrogen, phosphorus). Culturing microalgae in phototrophic conditions comprises supplying light and inorganic carbon (e.g., carbon dioxide) to cells in an aqueous culture medium comprising trace metals and nutrients (e.g., nitrogen, phosphorus).

In some embodiments, the microalgae cells can be harvested from a culture and used as whole cells in a liquid composition for application to seeds and plants, while in other embodiments the harvested microalgae cells can be subjected to downstream processing and the resulting biomass or extract can be used in a dried composition (e.g., powder, pellet) or a liquid composition (e.g., suspension, solution) for application to plants, soil, or a combination thereof. Non-limiting examples of downstream processing comprise: drying the cells, lysing the cells, and subjecting the harvested cells to a solvent or supercritical carbon dioxide extraction process to isolate an oil or protein. In some embodiments, the extracted (i.e., residual) biomass remaining from an extraction process can be used alone or in combination with other microalgae or extracts in a liquid composition for application to plants, soil, or a combination thereof. By subjecting the microalgae to an extraction process the resulting biomass is transformed from a natural whole state to a lysed condition where the cell is missing a significant amount of the natural components, thus differentiating the extracted microalgae biomass from that which is found in nature. Excreted products from the microalgae can also be isolated from a microalgae culture using downstream processing methods.

In some embodiments, microalgae can be the dominate active ingredient source in the composition. In some embodiments, the microalgae population of the composition can include whole biomass, substantially extracted biomass, excreted products (e.g., EPS), extracted protein, or extracted oil. In some embodiments, microalgae include at least 99% of the active ingredient sources of the composition. In some embodiments, microalgae include at least 95% of the active ingredient sources of the composition. In some embodiments, microalgae include at least 90% of the active ingredient sources of the composition. In some embodiments, microalgae include at least 80% of the active ingredient sources of the composition. In some embodiments, microalgae include at least 70% of the active ingredient sources of the composition. In some embodiments, microalgae include at least 60% of the active ingredient sources of the composition. In some embodiments, microalgae include at least 50% of the active ingredient sources of the composition. In some embodiments, microalgae include at least 40% of the active ingredient sources of the composition. In some embodiments, microalgae include at least 30% of the active ingredient sources of the composition. In some embodiments, microalgae include at least 20% of the active ingredient sources of the composition. In some embodiments, microalgae include at least 10% of the active ingredient sources of the composition. In some embodiments, microalgae include at least 5% of the active ingredient sources of the composition. In some embodiments, microalgae include at least 1% of the active ingredient sources of the composition. In some embodiments, the composition lacks any detectable amount of any other active ingredient source other than microalgae.

In some embodiments, microalgae biomass, excreted products, or extracts can also be mixed with biomass or extracts from other plants, microalgae, macroalgae, seaweeds, and kelp. In some embodiments, microalgae biomass, excreted products, or extracts can also be mixed with fish oil. Non-limiting examples of other plants, macroalgae, seaweeds, and kelp fractions that can be combined with microalgae cells can include species of *Lemna, Gracilaria, Kappaphycus, Ascophyllum, Macrocystis, Fucus, Laminaria, Sargassum, Turbinaria*, and *Durvilea*. In further embodiments, the extracts can comprise, but are not limited to, liquid extract from a species of *Kappaphycus*. In some embodiments, the extracts can include 50% or less by volume of the composition. In some embodiments, the extracts can include 40% or less by volume of the composition. In some embodiments, the extracts can include 30% or less by volume of the composition. In some embodiments, the extracts can include 20% or less by volume of the composition. In some embodiments, the extracts can include 10% or less by volume of the composition. In some embodiments, the extracts can include 5% or less by volume of the composition. In some embodiments, the extracts can include 4% or less by volume of the composition. In some embodiments, the extracts can include 3% or less by volume of the composition. In some embodiments, the extracts can include 2% or less by volume of the composition. In some embodiments, the extracts can include 1% or less by volume of the composition.

The term "microalgae" refers to microscopic single cell organisms such as microalgae, cyanobacteria, algae, diatoms, dinoflagelattes, freshwater organisms, marine organisms, or other similar single cell organisms capable of growth in phototrophic, mixotrophic, or heterotrophic culture conditions.

In some embodiments, microalgae biomass, excreted product, or extracts can also be sourced from multiple types of microalgae, to make a composition that is beneficial when applied to plants or soil. Non-limiting examples of microalgae that can be used in the compositions and methods of the present invention include microalgae in the classes: Eustigmatophyceae, Chlorophyceae, Prasinophyceae, Haptophyceae, Cyanidiophyceae, Prymnesiophyceae, Porphyridiophyceae, Labyrinthulomycetes, Trebouxiophyceae, Bacillariophyceae, and Cyanophyceae. The class Cyanidiophyceae includes species of *Galdieria*. The class Chlorophyceae includes species of *Haematococcus, Scenedesmus, Chlamydomonas*, and *Micractinium*. The class Prymnesiophyceae includes species of *Isochrysis* and *Pavlova*. The class Eustigmatophyceae includes species of *Nannochloropsis*. The class Porphyridiophyceae includes species of *Porphyridium*. The class Labyrinthulomycetes includes species of *Schizochytrium* and *Aurantiochytrium*. The class Prasinophyceae includes species of *Tetraselmis*. The class Trebouxiophyceae includes species of *Chlorella* and *Botryococcus*. The class Bacillariophyceae includes species of *Phaeodactylum*. The class Cyanophyceae includes species of *Spirulina*.

Non-limiting examples of microalgae genus and species that can be used in the compositions and methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Aurantiochytrium* sp., *Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomonas* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Galdieria* sp., *Gleocapsa* sp., *Gloeothamnion* sp., *Haematococcus pluvialis, Hymenomonas* sp., *Isochrysis aff galbana, Isochrysis galbana, Lepocinclis, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis camerae, Pleurochrysis dentate, Pleurochrysis* sp., *Porphyridium* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta,*

*Tagetes patula, Tetraedron, Tetraselmis* sp., *Tetraselmis suecica, Thalassiosira weissflogii,* and *Viridiella fridericiana.*

Analysis of the DNA sequence of the strain of *Chlorella* sp. described in the specification was done in the NCBI 18s rDNA reference database at the Culture Collection of Algae at the University of Cologne (CCAC) showed substantial similarity (i.e., greater than 95%) with multiple known strains of *Chlorella* and *Micractinium*. Those of skill in the art will recognize that *Chlorella* and *Micractinium* appear closely related in many taxonomic classification trees for microalgae, and strains and species may be re-classified from time to time. Thus for references throughout the instant specification for *Chlorella* sp., it is recognized that microalgae strains in related taxonomic classifications with similar characteristics to the reference *Chlorella* sp. strain would reasonably be expected to produce similar results.

Additionally, taxonomic classification has also been in flux for organisms in the genus *Schizochytrium*. Some organisms previously classified as *Schizochytrium* have been reclassified as *Aurantiochytrium, Thraustochytrium*, or *Oblongichytrium*. See Yokoyama et al. Taxonomic rearrangement of the genus *Schizochytrium* sensu lato based on morphology, chemotaxonomic characteristics, and 18S rRNA gene phylogeny (Thrausochytriaceae, Labyrinthulomycetes): emendation for *Schizochytrium* and erection of *Aurantiochytrium* and *Oblongichytrium* gen. nov. *Mycoscience* (2007) 48:199-211. Those of skill in the art will recognize that *Schizochytrium, Aurantiochytrium, Thraustochytrium*, and *Oblongichytrium* appear closely related in many taxonomic classification trees for microalgae, and strains and species may be re-classified from time to time. Thus for references throughout the instant specification for *Schizochytrium*, it is recognized that microalgae strains in related taxonomic classifications with similar characteristics to *Schizochytrium* would reasonably be expected to produce similar results.

By artificially controlling aspects of the microalgae culturing process such as the organic carbon feed (e.g., acetic acid, acetate), oxygen levels, pH, and light, the culturing process differs from the culturing process that microalgae experiences in nature. In addition to controlling various aspects of the culturing process, intervention by human operators or automated systems occurs during the non-axenic mixotrophic culturing of microalgae through contamination control methods to prevent the microalgae from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus through artificial control of aspects of the culturing process and intervening in the culturing process with contamination control methods, the microalgae culture produced as a whole and used in the described inventive compositions differs from the culture that results from a microalgae culturing process that occurs in nature.

During the mixotrophic culturing process the microalgae culture canalso include cell debris and compounds excreted from the microalgae cells into the culture medium. The output of the microalgae mixotrophic culturing process provides the active ingredient for composition that is applied to plants for improving yield and quality without separate addition to or supplementation of the composition with other active ingredients not found in the mixotrophic microalgae whole cells and accompanying culture medium from the mixotrophic culturing process such as, but not limited to: microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber).

In some embodiments, the microalgae can be previously frozen and thawed before inclusion in the liquid composition. In some embodiments, the microalgae may not have been subjected to a previous freezing or thawing process. In some embodiments, the microalgae whole cells have not been subjected to a drying process. The cell walls of the microalgae of the composition have not been lysed or disrupted, and the microalgae cells have not been subjected to an extraction process or process that pulverizes the cells. The microalgae whole cells are not subjected to a purification process for isolating the microalgae whole cells from the accompanying constituents of the culturing process (e.g., trace nutrients, residual organic carbon, bacteria, cell debris, cell excretions), and thus the whole output from the microalgae culturing process comprising whole microalgae cells, culture medium, cell excretions, cell debris, bacteria, residual organic carbon, and trace nutrients, is used in the liquid composition for application to plants. In some embodiments, the microalgae whole cells and the accompanying constituents of the culturing process are concentrated in the composition. In some embodiments, the microalgae whole cells and the accompanying constituents of the culturing process are diluted in the composition to a low concentration. The microalgae whole cells of the composition are not fossilized. In some embodiments, the microalgae whole cells are not maintained in a viable state in the composition for continued growth after the method of using the composition in a soil or foliar application. In some embodiments, the microalgae base composition can be biologically inactive after the composition is prepared. In some embodiments, the microalgae base composition can be substantially biologically inactive after the composition is prepared. In some embodiments, the microalgae base composition can increase in biological activity after the prepared composition is exposed to air.

In some embodiments, a liquid composition can include low concentrations of bacteria contributing to the solids percentage of the composition in addition to the microalgae cells. Examples of bacteria found in non-axenic mixotrophic conditions can be found in WO2014/074769A2 (Ganuza, et al.), hereby incorporated by reference. A live bacteria count can be determined using methods known in the art such as plate counts, plates counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture can range from $10^4$ to $10^9$ CFU/mL, and can depend on contamination control measures taken during the culturing of the microalgae. The level of bacteria in the composition can be determined by an aerobic plate count which quantifies aerobic colony forming units (CFU) in a designated volume. In some embodiments, the composition includes an aerobic plate count of 40,000-400,000 CFU/mL. In some embodiments, the composition includes an aerobic plate count of 40,000-100,000 CFU/mL. In some embodiments, the composition includes an aerobic plate count of 100,000-200,000 CFU/mL. In some embodiments, the composition includes an aerobic plate count of 200,000-300,000 CFU/mL. In some embodiments, the composition includes an aerobic plate count of 300,000-400,000 CFU/mL.

In some embodiments, the microalgae based composition can be supplemented with a supplemental nutrient such as nitrogen, phosphorus, or potassium to increase the levels within the composition to at least 1% of the total composition (i.e., addition of N, P, or K to increase levels at least 1-0-0, 0-1-0, 0-0-1, or combinations thereof). In some embodiments, the microalgae composition can be supplemented with nutrients such as, but not limited to, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium. In some embodiments, the supplemented nutrient is not uptaken, chelated, or absorbed by the microalgae. In some embodiments, the concentration of the supplemental nutrient can include 1-50 g per 100 g of the composition.

A liquid composition comprising microalgae can be stabilized by heating and cooling in a pasteurization process. As shown in the Examples, the inventors found that the active ingredients of the microalgae based composition maintained effectiveness in at least one characteristic of a plant after being subjected to the heating and cooling of a pasteurization process. In other embodiments, liquid compositions with whole cells or processed cells (e.g., dried, lysed, extracted) of microalgae cells may not need to be stabilized by pasteurization. For example, microalgae cells that have been processed, such as by drying, lysing, and extraction, or extracts can include such low levels of bacteria that a liquid composition can remain stable without being subjected to the heating and cooling of a pasteurization process.

In some embodiments, the composition can be heated to a temperature in the range of 50–70° C. In some embodiments, the composition can be heated to a temperature in the range of 55–65° C. In some embodiments, the composition can be heated to a temperature in the range of 58–62° C. In some embodiments, the composition can be heated to a temperature in the range of 50–60° C. In some embodiments, the composition can be heated to a temperature in the range of 60–70° C.

In some embodiments, the composition can be heated for a time period in the range of 90-150 minutes. In some embodiments, the composition can be heated for a time period in the range of 110-130 minutes. In some embodiments, the composition can be heated for a time period in the range of 90-100 minutes. In some embodiments, the composition can be heated for a time period in the range of 100-110 minutes. In some embodiments, the composition can be heated for a time period in the range of 110-120 minutes. In some embodiments, the composition can be heated for a time period in the range of 120-130 minutes. In some embodiments, the composition can be heated for a time period in the range of 130-140 minutes. In some embodiments, the composition can be heated for a time period in the range of 140-150 minutes.

After the step of heating or subjecting the liquid composition to high temperatures is complete, the compositions can be cooled at any rate to a temperature that is safe to work with. In one non-limiting embodiment, the composition can be cooled to a temperature in the range of 35-45° C. In some embodiments, the composition can be cooled to a temperature in the range of 36-44° C. In some embodiments, the composition can be cooled to a temperature in the range of 37-43° C. In some embodiments, the composition can be cooled to a temperature in the range of 38-42° C. In some embodiments, the composition can be cooled to a temperature in the range of 39-41° C. In further embodiments, the pasteurization process can be part of a continuous production process that also involves packaging, and thus the liquid composition can be packaged (e.g., bottled) directly after the heating or high temperature stage without a cooling step.

In some embodiments, the composition can include 5-30% solids by weight of microalgae cells (i.e., 5-30 g of microalgae cells/100 mL of the liquid composition). In some embodiments, the composition can include 5-20% solids by weight of microalgae cells. In some embodiments, the composition can include 5-15% solids by weight of microalgae cells. In some embodiments, the composition can include 5-10% solids by weight of microalgae cells. In some embodiments, the composition can include 10-20% solids by weight of microalgae cells. In some embodiments, the composition can include 10-20% solids by weight of microalgae cells. In some embodiments, the composition can include 20-30% solids by weight of microalgae cells. In some embodiments, further dilution of the microalgae cells percent solids by weight can occur before application for low concentration applications of the composition.

In some embodiments, the composition can include less than 1% by weight of microalgae biomass or extracts (i.e., less than 1 g of microalgae derived product/100 mL of the liquid composition). In some embodiments, the composition can include less than 0.9% by weight of microalgae biomass or extracts. In some embodiments, the composition can include less than 0.8% by weight of microalgae biomass or extracts. In some embodiments, the composition can include less than 0.7% by weight of microalgae biomass or extracts. In some embodiments, the composition can include less than 0.6% by weight of microalgae biomass or extracts. In some embodiments, the composition can include less than 0.5% by weight of microalgae biomass or extracts. In some embodiments, the composition can include less than 0.4% by weight of microalgae biomass or extracts. In some embodiments, the composition can include less than 0.3% by weight of microalgae biomass or extracts. In some embodiments, the composition can include less than 0.2% by weight of microalgae biomass or extracts. In some embodiments, the composition can include less than 0.1% by weight of microalgae biomass or extracts. In some embodiments, the composition can include at least 0.0001% by weight of microalgae biomass or extracts. In some embodiments, the composition can include at least 0.001% by weight of microalgae biomass or extracts. In some embodiments, the composition can include at least 0.01% by weight of microalgae biomass or extracts. In some embodiments, the composition can include at least 0.1% by weight of microalgae biomass or extracts. In some embodiments, the composition can include 0.0001-1% by weight of microalgae biomass or extracts. In some embodiments, the composition can include 0.0001-0.001% by weight of microalgae biomass or extracts. In some embodiments, the composition can include 0.001-0.01% by weight of microalgae biomass or extracts. In some embodiments, the composition can include 0.01-0.1% by weight of microalgae biomass or extracts. In some embodiments, the composition can include 0.1-1% by weight of microalgae biomass or extracts.

In some embodiments, an application concentration of 0.1% of microalgae biomass or extract equates to 0.04 g of microalgae biomass or extract in 40 mL of a composition. While the desired application concentration to a plant can be 0.1% of microalgae biomass or extract, the composition can be packaged as a 10% concentration (0.4 mL in 40 mL of a composition). Thus a desired application concentration of 0.1% would require 6,000 mL of the 10% microalgae biomass or extract in the 100 gallons of water applied to the assumption of 15,000 plants in an acre, which is equivalent to an application rate of about 1.585 gallons per acre. In some embodiments, a desired application concentration of 0.01% of microalgae biomass or extract using a 10% concentration composition equates to an application rate of about 0.159 gallons per acre. In some embodiments, a desired application concentration of 0.001% of microalgae biomass or extract using a 10% concentration composition equates to an application rate of about 0.016 gallons per acre. In some embodiments, a desired application concentration of 0.0001% of microalgae biomass or extract using a 10% concentration composition equates to an application rate of about 0.002 gallons per acre.

In another non-limiting embodiment, correlating the application of the microalgae biomass or extract on a per plant basis using the assumption of 15,000 plants per acre, the composition application rate of 1 gallon per acre is equal to about 0.25 mL per plant=0.025 g per plant=25 mg of microalgae biomass or extract per plant. The water requirement assumption of 100 gallons per acre is equal to about 35 mL of water per plant. Therefore, 0.025 g of microalgae biomass or extract in 35 mL of water is equal to about 0.071 g of microalgae biomass or extract per 100 mL of composition equates to about a 0.07% application concentration. In some embodiments, the microalgae biomass or extract based composition can be applied at a rate in a range as low as about 0.001-10 gallons per acre, or as high as up to 150 gallons per acre.

In some embodiments, stabilizing means that are not active regarding the improvement of plant germination, emergence, maturation, quality, and yield, but instead aid in stabilizing the composition can be added to prevent the proliferation of unwanted microorganisms (e.g., yeast, mold) and prolong shelf life. Such inactive but stabilizing means can include an acid, such as but not limited to phosphoric acid or citric acid, and a yeast and mold inhibitor, such as but not limited to potassium sorbate. In some embodiments, the stabilizing means are suitable for plants and do not inhibit the growth or health of the plant. In the alternative, the stabilizing means can contribute to nutritional properties of the liquid composition, such as but not limited to, the levels of nitrogen, phosphorus, or potassium.

In some embodiments, the composition can include less than 0.3% phosphoric acid. In some embodiments, the composition can include 0.01-0.3% phosphoric acid. In some embodiments, the composition can include 0.05-0.25% phosphoric acid. In some embodiments, the composition can include 0.01-0.1% phosphoric acid. In some embodiments, the composition can include 0.1-0.2% phosphoric acid. In some embodiments, the composition can include 0.2-0.3% phosphoric acid. In some embodiments, the composition can include less than 0.3% citric acid. In some embodiments, the composition can include 0.01-0.3% citric acid. In some embodiments, the composition can include 0.05-0.25% citric acid. In some embodiments, the composition can include 0.01-0.1% citric acid. In some embodiments, the composition can include 0.1-0.2% citric acid. In some embodiments, the composition can include 0.2-0.3% citric acid.

In some embodiments, the composition can include less than 0.5% potassium sorbate. In some embodiments, the composition can include 0.01-0.5% potassium sorbate. In some embodiments, the composition can include 0.05-0.4% potassium sorbate. In some embodiments, the composition can include 0.01-0.1% potassium sorbate. In some embodiments, the composition can include 0.1-0.2% potassium sorbate. In some embodiments, the composition can include 0.2-0.3% potassium sorbate. In some embodiments, the composition can include 0.3-0.4% potassium sorbate. In some embodiments, the composition can include 0.4-0.5% potassium sorbate.

In some embodiments, the composition is a liquid and substantially includes of water. In some embodiments, the composition can include 70-99% water. In some embodiments, the composition can include 85-95% water. In some embodiments, the composition can include 70-75% water. In some embodiments, the composition can include 75-80% water. In some embodiments, the composition can include 80-85% water. In some embodiments, the composition can include 85-90% water. In some embodiments, the composition can include 90-95% water. In some embodiments, the composition can include 95-99% water. The liquid nature and high water content of the composition facilitates administration of the composition in a variety of manners, such as but not limit to: flowing through an irrigation system, flowing through an above ground drip irrigation system, flowing through a buried drip irrigation system, flowing through a central pivot irrigation system, sprayers, sprinklers, and water cans.

In some embodiments, the liquid composition can be used immediately after formulation, or can be stored in containers for later use. In some embodiments, the composition can be stored out of direct sunlight. In some embodiments, the composition can be refrigerated. In some embodiments, the composition can be stored at 1-10° C. In some embodiments, the composition can be stored at 1-3° C. In some embodiments, the composition can be stored at 3-5° C. In some embodiments, the composition can be stored at 5-8° C. In some embodiments, the composition can be stored at 8-10° C.

In some embodiments, administration of the liquid composition to a seed or plant can be in an amount effective to produce an enhanced characteristic in plants compared to a substantially identical population of untreated seeds or plants. Such enhanced characteristics can include accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased fruit yield, increased fruit growth, and increased fruit quality. Non-limiting examples of such enhanced characteristics can include accelerated achievement of the hypocotyl stage, accelerated protrusion of a stem from the soil, accelerated achievement of the cotyledon stage, accelerated leaf formation, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased shoot weight (indicator of plant health), increased plant height, increased thatch height, increased resistance to salt stress, increased plant resistance to heat stress (temperature stress), increased plant resistance to heavy metal stress, increased plant resistance to drought, increased plant resistance to disease, improved color, reduced insect damage, reduced blossom end rot, and reduced sun burn. Such enhanced characteristics can occur individually in a plant, or in combinations of multiple enhanced characteristics.

In some embodiments, after harvest of the microalgae from the culturing vessel, the microalgae biomass can be dried or dehydrated to form a composition of dried microalgae biomass (i.e., reduced moisture content). The microalgae biomass can be dried by at least one method selected from the group consisting of: freeze drying (or lypohilization), drum (or rotary) drying, spray drying, crossflow air drying, solar drying, vacuum shelf drying, pulse combustion drying, flash drying, furnace drying, belt conveyor drying, and refractance window drying. In some embodiments, the microalgae cells can be dried by a combination of two or more methods, such as in a process with multiple drying methods in series. The process of drying the microalgae biomass can reduce the percent moisture (on a wet basis) to the range of about 1-15% and result in a cake, flakes, or a powder, which is more uniform and more stable than the wet culture of microalgae. In some embodiments, the dried microalgae cells can be intact. In some embodiments, the dried microalgae cells can be lysed or disrupted. In some embodiments, the microalgae cells can be lysed or disrupted prior to or after drying by mechanical, electrical, acoustic, or chemical means. In some embodiments, drying the microalgae cells achieves an acceptable product stability for storage, with the reduction or elimination of chemical stabilizers. The composition can be stored in any suitable container such as, but not limited to, a bag, bucket, jug, tote, or bottle.

In some embodiments, the dried microalgae biomass can have a moisture content of 1-15% on a wet basis. In some embodiments, the dried microalgae biomass can have a moisture content of 1-2% on a wet basis. In some embodiments, the dried microalgae biomass can have a moisture content of 2-3% on a wet basis. In some embodiments, the dried microalgae biomass can have a moisture content of 3-5% on a wet basis. In some embodiments, the dried microalgae biomass can have a moisture content of 5-7% on a wet basis. In some embodiments, the dried microalgae biomass can have a moisture content of 7-10% on a wet basis. In some embodiments, the dried microalgae biomass can have a moisture content of 10-12% on a wet basis. In some embodiments, the dried microalgae biomass can have a moisture content of 12-15% on a wet basis. In some embodiments, the dried microalgae biomass can have a moisture content of 1-8% on a wet basis. In some embodiments, the dried microalgae biomass can have a moisture content of 8-15% on a wet basis.

The various drying processes can have different capabilities such as, but not limited to, the amount of moisture that can be removed, the preservation of metabolites (e.g., proteins, lipids, pigments, carbohydrates, polysaccharides, soluble nitrogen, phytohormones), and the effect on the cell wall or membrane. For example, loss of protein in *Spirulina* biomass has been found to increase proportionally as the drying temperature increases. Additionally, drying at high temperatures has been shown to alter polymer chains, alter interactions between polysaccharide and glycoprotein, and increase bound water content of polysaccharides. Pigments and fatty acids are also known to oxidize and de-stabilize to different degrees in different drying processes. The effectiveness of each drying method can also vary based on the microalgae species due to different physical characteristics of the microalgae (e.g., sheer sensitivity, cell size, cell wall thickness and composition). The method of drying and drying method parameters can also result in a structural change to the microalgae cell such as, but not limited to, increased porosity in the cell wall, changes in the cell wall make up or bonds, and measurable changes in cell characteristics (e.g., elasticity, viscosity, digestibility); as wells as functional differences when applied to plants that can be measured in changes in plant performance or plant characteristics. Drying microalgae with a combination of methods in series can also result in structural and functional changes, minimize structural and functional changes, or increase the effectiveness for a particular type of microalgae.

Drum drying includes the use of sloped, rotating cylinders which use gravity to move the microalgal biomass from one end to the other. Drum drying can be conducted with direct contact between a hot gas and the microalgal biomass, or indirect heating in which the gas and microalgal biomass is separated by a barrier such as a steel shell. A non-limiting example of a drum drying process for *Scenedesmus* can include 10 seconds of heating at 120° C. Possible effects to the microalga biomass in a drum drying process include sterilization of the biomass, and breaking of the cell wall. Microalgal biomass that is drum dried can have higher digestibility than microalgal biomass that is spray dried.

Freeze drying includes freezing the microalgal biomass and then transferring the frozen biomass to a vacuum chamber with reduced pressure (e.g., 4.6 Torr). The ice in the microalgal biomass changes to vapor through sublimation which is collected on an extremely cold condenser and removed from the vacuum chamber. Freeze drying typically minimizes the degradation of unsaturated fatty acids and pigments (e.g., carotenoids) through oxidation, which preserves the nutritional value of the microalgal biomass. Although the targeted removal of water in the freeze drying process is beneficial, the process is very costly and time consuming which makes freeze drying impractical for many commercial applications. In some embodiments, microalgae dried by freeze drying can include 2-6% moisture (on a wet basis). A non-limiting example of a freeze drying process for *Scenedesmus* can include 24 hours at −84° C. Freeze drying is known to maintain the integrity of the microalgal cell, but is also known been known in some cases to disrupt the cell or increase the pore size in the cell wall. In *Scenedesmus*, freeze drying was found to decrease rigidity, increase surface area by 165%, and increase pore size by 19% of the cells (see eSEM images below). In *Phaeodactylum ricornutum*, freeze drying had no effect on the total lipid content, made the cells more susceptible to lipolysis (i.e., breakdown of lipids, hydrolysis of triglycerides into glycerol and free fatty acids) upon storage than spray dried cells, and made the cells less susceptible to oxidation than spray dried cells.

Spray drying includes atomizing an aqueous microalgae culture into droplets sprayed downwardly in a vertical tower through which hot gases pass downward. The gas stream can be exhausted through a cyclonic separator. The process of spray drying is expensive, but slightly cheaper than freeze drying. Spray drying has become the method of choice for high value products (>$1,000/ton). With the proper type of burner, oxygen can be virtually eliminated from the recycled drying gas, which prevents the oxidation of oxygen sensitive products (e.g., carotenoids). In some embodiments, microalgae dried by spray drying can include 1-7% moisture (on a wet basis). Examples of spray drying systems include: box dryers, tall-form spray dryers, fluidized bed dryers, and moving fluidized bed dryers (e.g., FilterMat spray dryer GEA Process Engineering Inc.). An open cycle spray dryer with a particular direct fired air heater can operate at elevated temperatures (e.g., 60-93° C.) and high oxygen concentrations (e.g., 19-20%). The possible effects of spray drying on microalgal biomass include rupturing the cells walls, reduction of protein content by 10-15%, significant deterioration of pigments (depending on the oxygen concentration), and a lower digestibility than drum drying. In *Phyaeodactylum ricornutum*, spray drying had no effect on the total lipid content, made the cells less susceptible to lipolysis than freeze drying, and made the cells more susceptible to oxidation than freeze drying (possibly due to the breakdown of protective carotenoids).

Crossflow air drying uses movement of heated air across a layer of microalgae on a tray, which is a modification of indirect solar and convection oven driers. Crossflow air drying is faster than solar drying, cheaper than drum drying, and is known to typically not break the microalgal cell wall. In some embodiments, microalgae dried by crossflow air drying can include 8-12% moisture (on a wet basis). Non-limiting examples of crossflow air drying for *Spirulina* can include: 1) a temperature of 62° C. for 14 hours, 2) a temperature of 50-60° C., a relative humidity of 7-10%, an air velocity of 1.5 m/s, and a duration of 150-220 minutes, 3) a temperature of 40-60° C. and an air velocity of 1.9-3.8 m/s, and 4) temperatures of 50-70° C. for layers of 3-7 mm in a perforated tray with parallel air flow. Crossflow air drying of *Spirulina* has shown a loss in protein of about 17% and a loss in phycocyanin of 37-50%. Particularly, degradation of phycocyanin was found to occur above 60° C., but there was no significant change in the fatty acid composition in the crossflow air drying methods.

Non-limiting examples of crossflow air drying of *Chlorella kessleri* and *Chlamydomonas reinhardtii* can include a temperature of 55° C. for more than 5 hours. Crossflow air drying of *Chlorella kessleri* and *Chlamydomonas reinhardtii* has produced a reduction of chlorophyll relative to the dry cell weight, an increase of total fatty acid content relative to the dry cell, a decrease of polar lipids relative to the dry cell weight, and a decrease in the availability of nutritional salts (e.g., S, N). A cell's sensitivity to air drying stress (as measured through the change in chlorophyll) can be correlated to the properties of the cell wall. For example, the crossflow air dried *Chlamydomonas reinhardtii* (hydroxyproline-rich glucoprotein based cell walls) had a larger decrease in chlorophyll than the *Chlorella kessleri* (sugar based cell walls), which can be associated with the cell wall's ability to restructure in S and N deficient conditions. In a non-limiting example of drying 5-7 mm thick layers of *Aphanothece microscopia Nageli* at temperatures of 40-60° C. with parallel air flow of 1.5 m/s, it was found that drying conditions influenced the concentrations of protein, carbohydrates, and lipids in the biomass.

Solar drying methods can include the use of direct solar radiation to dry microalgae on sand or a plastic sheet, or the indirect use of solar radiation to heat air that is circulated around microalgae in a dryer. Direct solar drying is strongly weather dependent, slow, and can require a short duration of high heat (e.g., 120° C.) to increase the biological value of the microalgal biomass. A non-limiting example of a direct solar drying process for *Scenedesmus* can include a 1,500 micron thickness white plastic drying bed liner, a temperature of 25-30° C., and a duration of 72 hours. The possible effects of direct solar drying on microalgal biomass include chlorophyll degradation, overheating of the biomass, and creation of an unpleasant odor. Indirect solar drying prevents overheating, has a higher drying rate than direct solar drying, but produces a less attractive profile in the final product. An indirect solar drying method for microalgae can include temperature of 65-70° C. for 0.5-6 hours.

Drying of a thin film of microalgal biomass in a convection oven is a fairly common practice performed in scientific literature to test the biomass going through further processing, but may be less practical for many commercial applications. Thin film convection oven drying has been demonstrated in the literature with species of *Chlorella, Chlamydomonas*, and *Scenedesmus*. In some embodiments, microalgae dried by oven drying can include 6-10% moisture (on a wet basis). Thin film convection oven drying methods can include temperatures of 30-90° C., and durations of 4-12 hours. Thin film convection oven dried microalgal biomass showed no significant change in the fatty acid profile and a slight decrease in the degree of unsaturation of fatty acids at higher temperature for ruptured cells (likely due to oxidation causing cleavage of unsaturated bonds).

Microalgae can be dried in thin layers with heat at a reduced pressure. Non-limiting examples of drying of *Spirulina* in layers within a vacuum can include temperatures of 50-65° C. and a pressure of 0.05-0.06 atm. Possible effects on the microalgae that may result from vacuum shelf drying include development of a hygroscopic property (i.e., ability to attract and hold water particles from the surrounding environment by absorption or adsorption) and development of a porous structure.

Pulse combustion drying uses a blast of controlled heat to flash dry the microalgae. Air is pumped into a combustion chamber, mixed with a fuel and ignited to created pressurized hot gas (e.g., at 3 psi). The dryer can automatically blast the heated gas with quench air to control the temperature of the heated gas before coming into contact with the microalgae. The process is then repeated multiple times to provide the pulses of heated gas. Pulse combustion heating is known to dry microalgae at a low heat which preserves the integrity and nutritional value of the microalgae. Flash drying includes spraying or injecting a mixture of dried and undried material into a hot gas stream, and is commonly used in wastewater sludge drying.

Drying of microalgae using an incinerator or furnace can include heating the biomass to a high temperature (e.g., 100° C.) to evaporate the water. The heating can be performed at a level below the temperature at which the microalgae will burn and can include using hot gases that proceed downwardly with the biomass in parallel flow. Microalgae that are dewatered to an appropriate solids level can be dried indirectly by heating elements lining the pathway of a belt conveyor. Refractance window drying is a dehydration method that uses infra-red light, rather than high direct temperature, to remove moisture from microalgae. Wet microalgae biomass can be translated through an evaporation chamber by a belt disposed above a circulating hot water reservoir to dry the microalgae with infra-red energy in a refractance window drying. In some embodiments, microalgae dried by refractance window drying can include 3-8% moisture (on a wet basis).

In some embodiments, the dry composition can be mixed with water and stabilized by heating and cooling in a pasteurization process, adjustment of pH, the addition of an inhibitor of yeast and mold growth, or combinations thereof. In one non-limiting example of preparing the dried microalgae composition for application to plants, the microalgae harvested from the culturing system is first held in a harvest tank before centrifuging the culture. Once the microalgae is centrifuged, the centrifuge discharges the fraction rich in microalgae whole cell solids, but also containing the accompanying constituents from the culture medium, into a container at a temperature of about 30° C. The microalgae composition is then dried.

Surprisingly, the inventors found that administration of the described composition in low concentration applications was effective in producing enhanced characteristics in plants. In some embodiments, a liquid composition can be administered before the seed is planted. In some embodiments, a liquid composition can be administered at the time the seed is planted. In some embodiments, a liquid composition can be administered after the seed is planted. In some embodiments, a liquid composition can be administered to plants that have emerged from the ground. In some embodiments, a dried composition can be applied to the soil before, during, or after the planting of a seed. In some embodiments, a dried composition can be applied to the soil before or after a plant emerges from the soil.

In some embodiments, the volume or mass of the microalgae based composition applied to a seed, seedling, or plant may not increase or decrease during the growth cycle of the plant (i.e., the amount of the microalgae composition applied to the plant will not change as the plant grows larger). In some embodiments, the volume or mass of the microalgae based composition applied to a seed, seedling, or plant can increase during the growth cycle of the plant (i.e., applied on a mass or volume per plant mass basis to provide more of the microalgae composition as the plant grows larger). In some embodiments, the volume or mass of the microalgae based composition applied to a seed, seedling, or plant can decrease during the growth cycle of the plant (i.e., applied on a mass or volume per plant mass basis to provide more of the microalgae composition as the plant grows larger).

Seed Soak Application

In one non-limiting embodiment, the administration of the liquid composition can include soaking the seed in an effective amount of the liquid composition before planting the seed. In some embodiments, the administration of the liquid composition further includes removing the seed from the liquid composition after soaking, and drying the seed before planting. In some embodiments, the seed can be soaked in the liquid composition for a time period in the range of 90-150 minutes. In some embodiments, the seed can be soaked in the liquid composition for a time period in the range of 110-130 minutes. In some embodiments, the seed can be soaked in the liquid composition for a time period in the range of 90-100 minutes. In some embodiments, the seed can be soaked in the liquid composition for a time period in the range of 100-110 minutes. In some embodiments, the seed can be soaked in the liquid composition for a time period in the range of 110-120 minutes. In some embodiments, the seed can be soaked in the liquid composition for a time period in the range of 120-130 minutes. In some embodiments, the seed can be soaked in the liquid composition for a time period in the range of 130-140 minutes. In some embodiments, the seed can be soaked in the liquid composition for a time period in the range of 140-150 minutes.

The composition can be diluted to a lower concentration for an effective amount in a seed soak application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae source components in the diluted composition can be calculated by the multiplying the original grams of microalgae sourced components per 100 mL by the ratio of the volume of the composition to the volume of water.

Soil Application—Seed

In another non-limiting embodiment, the administration of the composition can include contacting the soil in the immediate vicinity of the planted seed with an effective amount of the composition. In some embodiments, the liquid composition can be supplied to the soil by injection into a low volume irrigation system, such as but not limited to a drip irrigation system supplying water beneath the soil through perforated conduits or at the soil level by fluid conduits hanging above the ground or protruding from the ground. In some embodiments, the liquid composition can be supplied to the soil by a soil drench method wherein the liquid composition is poured on the soil.

The composition can be diluted to a lower concentration for an effective amount in a soil application by mixing a volume of the composition in a volume of water. The percent solids of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a soil application can include a rate in the range of 50-150 gallons/acre. In some embodiments, the rate of application of the liquid composition in a soil application can include a rate in the range of 75-125 gallons/acre. In some embodiments, the rate of application of the liquid composition in a soil application can include a rate in the range of 50-75 gallons/acre. In some embodiments, the rate of application of the liquid composition in a soil application can include a rate in the range of 75-100 gallons/acre. In some embodiments, the rate of application of the liquid composition in a soil application can include a rate in the range of 100-125 gallons/acre. In some embodiments, the rate of application of the liquid composition in a soil application can include a rate in the range of 125-150 gallons/acre.

In some embodiments, the rate of application of the liquid composition in a soil application can include a rate in the range of 10-50 gallons/acre. In some embodiments, the rate of application of the liquid composition in a soil application can include a rate in the range of 10-20 gallons/acre. In some embodiments, the rate of application of the liquid composition in a soil application can include a rate in the range of 20-30 gallons/acre. In some embodiments, the rate of application of the liquid composition in a soil application can include a rate in the range of 30-40 gallons/acre. In some embodiments, the rate of application of the liquid composition in a soil application can include a rate in the range of 40-50 gallons/acre.

In some embodiments, the rate of application of the liquid composition in a soil application can include a rate in the range of 0.01-10 gallons/acre. In some embodiments, the rate of application of the liquid composition in a soil application can include a rate in the range of 0.01-0.1 gallons/acre. In some embodiments, the rate of application of the liquid composition in a soil application can include a rate in the range of 0.1-1.0 gallons/acre. In some embodiments, the rate of application of the liquid composition in a soil application can include a rate in the range of 1-2 gallons/acre. In some embodiments, the rate of application of the liquid composition in a soil application can include a rate in the range of 2-3 gallons/acre. In some embodiments, the rate of application of the liquid composition in a soil application can include a rate in the range of 3-4 gallons/acre. In some embodiments, the rate of application of the liquid composition in a soil application can include a rate in the range of 4-5 gallons/acre. In some embodiments, the rate of application of the liquid composition in a soil application can include a rate in the range of 5-10 gallons/acre.

In some embodiments, the rate of application of the liquid composition in a soil application can include a rate in the range of 2-20 liters/acre. In some embodiments, the rate of application of the liquid composition in a soil application can include a rate in the range of 3.7-15 liters/acre. In some embodiments, the rate of application of the liquid composition in a soil application can include a rate in the range of 2-5 liters/acre. In some embodiments, the rate of application of the liquid composition in a soil application can include a rate in the range of 5-10 liters/acre. In some embodiments, the rate of application of the liquid composition in a soil application can include a rate in the range of 10-15 liters/acre. In some embodiments, the rate of application of the liquid composition in a soil application can include a rate in the range of 15-20 liters/acre.

Capillary Action Application

In another non-limiting embodiment, the administration of the liquid composition can include first soaking the seed in water, removing the seed from the water, drying the seed, applying an effective amount of the liquid composition below the seed planting level in the soil, and planting the seed, wherein the liquid composition supplied to the seed from below by capillary action. In some embodiments, the seed can be soaked in water for a time period in the range of 90-150 minutes. In some embodiments, the seed can be soaked in water for a time period in the range of 110-130 minutes. In some embodiments, the seed can be soaked in water for a time period in the range of 90-100 minutes. In some embodiments, the seed can be soaked in water for a time period in the range of 100-110 minutes. In some embodiments, the seed can be soaked in water for a time period in the range of 110-120 minutes. In some embodiments, the seed can be soaked in water for a time period in the range of 120-130 minutes. In some embodiments, the seed can be soaked in water for a time period in the range of 130-140 minutes. In some embodiments, the seed can be soaked in water for a time period in the range of 140-150 minutes.

The composition can be diluted to a lower concentration for an effective amount in a capillary action application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

Hydroponic Application

In another non-limiting embodiment, the administration of the liquid composition to a seed or plant can include applying the microalga based composition in combination with a nutrient medium to seeds disposed in and plants growing in a hydroponic growth medium or an inert growth medium (e.g., coconut husks). The liquid composition can be applied multiple times per day, per week, or per growing season.

Foliar Application

In one non-limiting embodiment, the administration of the composition can include contacting the foliage of the plant with an effective amount of the composition. In some embodiments, the liquid composition can be sprayed on the foliage by a hand sprayer, a sprayer on an agriculture implement, or a sprinkler.

The composition can be diluted to a lower concentration for an effective amount in a foliar application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a foliar application can include a rate in the range of 10-50 gallons/acre. In some embodiments, the rate of application of the liquid composition in a foliar application can include a rate in the range of 10-15 gallons/acre. In some embodiments, the rate of application of the liquid composition in a foliar application can include a rate in the range of 15-20 gallons/acre. In some embodiments, the rate of application of the liquid composition in a foliar application can include a rate in the range of 20-25 gallons/acre. In some embodiments, the rate of application of the liquid composition in a foliar application can include a rate in the range of 25-30 gallons/acre. In some embodiments, the rate of application of the liquid composition in a foliar application can include a rate in the range of 30-35 gallons/acre. In some embodiments, the rate of application of the liquid composition in a foliar application can include a rate in the range of 35-40 gallons/acre. In some embodiments, the rate of application of the liquid composition in a foliar application can include a rate in the range of 40-45 gallons/acre. In some embodiments, the rate of application of the liquid composition in a foliar application can include a rate in the range of 45-50 gallons/acre.

In some embodiments, the rate of application of the liquid composition in a foliar application can include a rate in the range of 0.01-10 gallons/acre. In some embodiments, the rate of application of the liquid composition in a foliar application can include a rate in the range of 0.01-0.1 gallons/acre. In some embodiments, the rate of application of the liquid composition in a foliar application can include a rate in the range of 0.1-1.0 gallons/acre. In some embodiments, the rate of application of the liquid composition in a foliar application can include a rate in the range of 1-2 gallons/acre. In some embodiments, the rate of application of the liquid composition in a foliar application can include a rate in the range of 2-3 gallons/acre. In some embodiments, the rate of application of the liquid composition in a foliar application can include a rate in the range of 3-4 gallons/ acre. In some embodiments, the rate of application of the liquid composition in a foliar application can include a rate in the range of 4-5 gallons/acre. In some embodiments, the rate of application of the liquid composition in a foliar application can include a rate in the range of 5-10 gallons/acre.

The frequency of the application of the composition can be expressed as the number of applications per period of time (e.g., two applications per month), or by the period of time between applications (e.g., one application every 21 days). In some embodiments, the plant can be contacted by the composition in a foliar application every 3-28 days. In some embodiments, the plant can be contacted by the composition in a foliar application every 4-10 days. In some embodiments, the plant can be contacted by the composition in a foliar application every 18-24 days. In some embodiments, the plant can be contacted by the composition in a foliar application every 3-7 days. In some embodiments, the plant can be contacted by the composition in a foliar application every 7-14 days. In some embodiments, the plant can be contacted by the composition in a foliar application every 14-21 days. In some embodiments, the plant can be contacted by the composition in a foliar application every 21-28 days.

Foliar application(s) of the composition generally begin after the plant has become established, but can begin before establishment, at defined time period after planting, or at a defined time period after emergence form the soil in some embodiments. In some embodiments, the plant can be first contacted by the composition in a foliar application 5-14 days after the plant emerges from the soil. In some embodiments, the plant can be first contacted by the composition in a foliar application 5-7 days after the plant emerges from the soil. In some embodiments, the plant can be first contacted by the composition in a foliar application 7-10 days after the plant emerges from the soil. In some embodiments, the plant can be first contacted by the composition in a foliar application 10-12 days after the plant emerges from the soil. In some embodiments, the plant can be first contacted by the composition in a foliar application 12-14 days after the plant emerges from the soil.

Soil Application—Plant

In another non-limiting embodiment, the administration of the composition can include contacting the soil in the immediate vicinity of the plant with an effective amount of the composition. In some embodiments, the liquid composition can be supplied to the soil by injection into to a low volume irrigation system, such as but not limited to a drip irrigation system supplying water beneath the soil through perforated conduits or at the soil level by fluid conduits hanging above the ground or protruding from the ground. In some embodiments, the liquid composition can be supplied to the soil by a soil drench method wherein the liquid composition is poured on the soil.

The composition can be diluted to a lower concentration for an effective amount in a soil application by mixing a volume of the composition in a volume of water. The concentration of microalgae sourced components resulting in the diluted composition can be calculated by the multiplying the original concentration of microalgae sourced components in the composition by the ratio of the volume of the composition to the volume of water. Alternatively, the grams of microalgae cells in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a soil application can include a rate in the range of 50-150 gallons/acre. In some embodiments, the rate of application of the liquid composition in a soil application can include a rate in the range of 75-125 gallons/acre. In some embodiments, the rate of application of the liquid composition in a soil application can include a rate in the range of 50-75 gallons/acre. In some embodiments, the rate of application of the liquid composition in a soil application can include a rate in the range of 75-100 gallons/acre. In some embodiments, the rate of application of the liquid composition in a soil application can include a rate in the range of 100-125 gallons/acre. In some embodiments, the rate of application of the liquid composition in a soil application can include a rate in the range of 125-150 gallons/acre.

In some embodiments, the rate of application of the liquid composition in a soil application can include a rate in the range of 10-50 gallons/acre. In some embodiments, the rate of application of the liquid composition in a soil application can include a rate in the range of 10-20 gallons/acre. In some embodiments, the rate of application of the liquid composition in a soil application can include a rate in the range of 20-30 gallons/acre. In some embodiments, the rate of application of the liquid composition in a soil application can include a rate in the range of 30-40 gallons/acre. In some embodiments, the rate of application of the liquid composition in a soil application can include a rate in the range of 40-50 gallons/acre.

In some embodiments, the rate of application of the liquid composition in a soil application can include a rate in the range of 0.01-10 gallons/acre. In some embodiments, the rate of application of the liquid composition in a soil application can include a rate in the range of 0.01-0.1 gallons/acre. In some embodiments, the rate of application of the liquid composition in a soil application can include a rate in the range of 0.1-1.0 gallons/acre. In some embodiments, the rate of application of the liquid composition in a soil application can include a rate in the range of 1-2 gallons/acre. In some embodiments, the rate of application of the liquid composition in a soil application can include a rate in the range of 2-3 gallons/acre. In some embodiments, the rate of application of the liquid composition in a soil application can include a rate in the range of 3-4 gallons/acre. In some embodiments, the rate of application of the liquid composition in a soil application can include a rate in the range of 4-5 gallons/acre. In some embodiments, the rate of application of the liquid composition in a soil application can include a rate in the range of 5-10 gallons/acre.

In some embodiments, the rate of application of the liquid composition in a soil application can include a rate in the range of 2-20 liters/acre. In some embodiments, the rate of application of the liquid composition in a soil application can include a rate in the range of 3.7-15 liters/acre. In some embodiments, the rate of application of the liquid composition in a soil application can include a rate in the range of 2-5 liters/acre. In some embodiments, the rate of application of the liquid composition in a soil application can include a rate in the range of 5-10 liters/acre. In some embodiments, the rate of application of the liquid composition in a soil application can include a rate in the range of 10-15 liters/acre. In some embodiments, the rate of application of the liquid composition in a soil application can include a rate in the range of 15-20 liters/acre.

The frequency of the application of the composition can be expressed as the number of applications per period of time (e.g., two applications per month), or by the period of time between applications (e.g., one application every 21 days). In some embodiments, the plant can be contacted by the composition in a soil application every 3-28 days. In some embodiments, the plant can be contacted by the composition in a soil application every 4-10 days. In some embodiments, the plant can be contacted by the liquid composition in a soil application every 18-24 days. In some embodiments, the plant can be contacted by the composition in a soil application every 3-7 days. In some embodiments, the plant can be contacted by the composition in a soil application every 7-14 days. In some embodiments, the plant can be contacted by the composition in a soil application every 14-21 days. In some embodiments, the plant can be contacted by the composition in a soil application every 21-28 days.

Soil application(s) of the composition generally begin after the plant has become established, but can begin before establishment, at defined time period after planting, or at a defined time period after emergence form the soil in some embodiments. In some embodiments, the plant can be first contacted by the composition in a soil application 5-14 days after the plant emerges from the soil. In some embodiments, the plant can be first contacted by the composition in a soil application 5-7 days after the plant emerges from the soil. In some embodiments, the plant can be first contacted by the liquid composition in a soil application 7-10 days after the plant emerges from the soil. In some embodiments, the plant can be first contacted by the composition in a soil application 10-12 days after the plant emerges from the soil. In some embodiments, the plant can be first contacted by the composition in a soil application 12-14 days after the plant emerges from the soil.

Whether in a seed soak, soil, capillary action, foliar, or hydroponic application the method of use includes relatively low concentrations of the composition. Even at such low concentrations, the described composition has been shown to be effective at producing an enhanced characteristic in plants. The ability to use low concentrations allows for a reduced impact on the environment that may result from over application and an increased efficiency in the method of use of the composition by requiring a small amount of material to produce the desired effect. In some embodiments, the use of the liquid composition with a low volume irrigation system in soil applications allows the low concentration of the liquid composition to remain effective and not be diluted to a point where the composition is no longer in at a concentration capable of producing the desired effect on the plants while also increasing the grower's water use efficiency.

In conjunction with the low concentrations of microalgae cells in the composition necessary to be effective for enhancing the described characteristics of plants, the composition does not have be to administered continuously or at a high frequency (e.g., multiple times per day, daily). The ability of the composition to be effective at low concentrations and a low frequency of application was an unexpected result, due to the traditional thinking that as the concentration of active ingredients decreases the frequency of application should increase to provide adequate amounts of the active ingredients. Effectiveness at low concentration and application frequency increases the material usage efficiency of the method of using the composition while also increasing the yield efficiency of the agricultural process.

Administration of a dry composition treatment to the soil, seed, or plant can be in an amount effective to produce an enhanced characteristic in the plant compared to a substantially identical population of untreated plant. Such enhanced characteristics can include accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased flowering, increased fruit yield, increased fruit growth, and increased fruit quality. Non-limiting examples of such enhanced characteristics can include accelerated achievement of the hypocotyl stage, accelerated protrusion of a stem from the soil, accelerated achievement of the cotyledon stage, accelerated leaf formation, increased leaf size, increased leaf area index, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased root mass (indicator of plant health), increased shoot weight (indicator of plant health), increased plant height, increased thatch height, increased resistance to salt stress, increased plant resistance to heat stress (temperature stress), increased plant resistance to heavy metal stress, increased plant resistance to drought, increased plant resistance to disease improved color, reduced insect damage, reduced blossom end rot, and reduced sun burn. Such enhanced characteristics can occur individually in a plant, or in combinations of multiple enhanced characteristics. The characteristic of flowering has is important for not only the ornamental market, but also for fruiting plants where an increase in flowering can correlate to an increase in fruit production.

Seed Coating

In one non-limiting embodiment, the administration of the dried microalgae composition treatment can include coating a seed. In some embodiments, a seed can be coated by passing through a slurry comprising microalgae and then dried. In some embodiments, the seed can be coated with the dried microalgae composition and other components such as, but not limited to, binders and fillers known in the art to be suitable for coating seeds. The fillers can include suitable inorganic particles such as, but not limited to, silicate particles, carbonate particles, and sulphate particles, quartz, zeolites, pumice, perlite, diatomaceous earth, pyrogene silica, $Sb_2O_3$, $TiO_2$, lithopone, ZnO, and hydrated aluminum oxide. The binders can include, but are not limited to, water-soluble polymers, polyvinyl acetate, polyvinyl alcohol, polyvinyl pyrrolidone, polyurethane, methyl cellulose, carboxymethyl cellulose, hydroxylpropyl cellulose, sodium alginate, polyacrylate, casein, gelatin, pullulan, polyacrylamide, polyethylene oxide, polystyrene, styrene acrylic copolymers, styrene butadiene polymers, poly (N-vinylacetamide), waxes, canauba wax, paraffin wax, polyethylene wax, bees wax, polypropylene wax, and ethylene vinyl acetate. In some embodiments, the seed coating can include a wetting and dispersing additive such as, but not limited to polyacrylates, organo-modified polyacrylates, sodium polyacrylates, polyurethanes, phosphoric acid esters, star polymers, and modified polyethers.

In some embodiments, the seed coating can include other components such as, but not limited to, a solvent, thickener, coloring agent, anti-foaming agent, biocide, surfactant, and pigment. In some embodiments, the seed coating can include a hydrogel or film coating materials. In some embodiments, the concentration of dried microalgae in the seed coating can include 0.001-20% solids. In some embodiments, the concentration of microalgae in the seed coating can include less than 0.1% solids. In some embodiments, the concentration of dried microalgae in the seed coating can include 0.001-0.01% solids. In some embodiments, the concentration of dried microalgae in the seed coating can include 0.01-0.1% solids. In some embodiments, the concentration of dried microalgae in the seed coating can include 0.1-1% solids. In some embodiments, the concentration of dried microalgae in the seed coating can include 1-2% solids. In some embodiments, the concentration of dried microalgae in the seed coating can include 2-3% solids. In some embodiments, the concentration of dried microalgae in the seed coating can include 3-5% solids. In some embodiments, the concentration of dried microalgae in the seed coating can include 5-10% solids. In some embodiments, the concentration of dried microalgae in the seed coating can include 10-15% solids. In some embodiments, the concentration of dried microalgae in the seed coating can include 15-20% solids. In some embodiments, the seed can be coated in a single step. In some embodiments, the seed can be coated in multiple steps. Conventional or otherwise suitable coating equipment or techniques can be used to coat the seeds. Suitable equipment can include drum coaters, fluidized beds, rotary coaters, side vended pan, tumble mixers, and spouted beds. Suitable techniques can include mixing in a container, tumbling, spraying, or immersion. After coating, the seeds can be dried or partially dried.

Soil Application

In another non-limiting embodiment, the administration of the dried microalgae composition treatment can include mixing an effective amount of the composition with a solid growth medium, such as soil, potting mix, compost, or inert hydroponic material, prior to planting a seed, seedling, or plant in the solid growth medium. The dried microalgae composition can be mixed in the solid growth medium at an inclusion level of 0.001-20% by volume. In some embodiments, the effective amount in a mixed solid growth medium application of the dried microalgae composition can include a concentration in the range of 0.001-0.01% solids. In some embodiments, the effective amount in a mixed solid growth medium application of the dried microalgae composition can include a concentration in the range of 0.01-0.1% solids. In some embodiments, the effective amount in a mixed solid growth medium application of the dried microalgae composition can include a concentration in the range of 0.1-1% solids. In some embodiments, the effective amount in a mixed solid growth medium application of the dried microalgae composition can include a concentration in the range of 1-3%% solids. In some embodiments, the effective amount in a mixed solid growth medium application of the dried microalgae composition can include a concentration in the range of 3-5% solids. In some embodiments, the effective amount in a mixed solid growth medium application of the dried microalgae composition can include a concentration in the range of 5-10% solids. In some embodiments, the effective amount in a mixed solid growth medium application of the dried microalgae composition can include a concentration in the range of 10-20% solids.

In another non-limiting embodiment, the administration of the dried microalgae composition treatment can include inclusion in a solid growth medium during in-furrow plants or broadcast application to the ground. The dried microalgae composition can be applied at a rate of 50-500 grams/acre. In some embodiments, the application rate of the dried microalgae composition can include 50-100 grams/acre. In some embodiments, the application rate of the dried microalgae composition can include 100-150 grams/acre. In some embodiments, the application rate of the dried microalgae composition can include 150-200 grams/acre. In some embodiments, the application rate of the dried microalgae composition can include 200-250 grams/acre. In some embodiments, the application rate of the dried microalgae composition can include 250-300 grams/acre. In some embodiments, the application rate of the dried microalgae composition can include 300-350 grams/acre. In some embodiments, the application rate of the dried microalgae composition can include 350-400 grams/acre. In some embodiments, the application rate of the dried microalgae composition can include 400-450 grams/acre. In some embodiments, the application rate of the dried microalgae composition can include 450-500 grams/acre.

The dried microalgae composition can be applied at a rate of 10-50 grams/acre. In some embodiments, the application rate of the dried microalgae composition can include 10-20 grams/acre. In some embodiments, the application rate of the dried microalgae composition can include 20-30 grams/acre. In some embodiments, the application rate of the dried microalgae composition can include 30-40 grams/acre. In some embodiments, the application rate of the dried microalgae composition can include 40-50 grams/acre.

The dried microalgae composition can be applied at a rate of 0.001-10 grams/acre. In some embodiments, the application rate of the dried microalgae composition can include 0.001-0.01 grams/acre. In some embodiments, the application rate of the dried microalgae composition can include 0.01-0.1 grams/acre. In some embodiments, the application rate of the dried microalgae composition can include 0.1-1.0 grams/acre. In some embodiments, the application rate of the dried microalgae composition can include 1-2 grams/acre. In some embodiments, the application rate of the dried microalgae composition can include 2-3 grams/acre. In some embodiments, the application rate of the dried microalgae composition can include 3-4 grams/acre. In some embodiments, the application rate of the dried microalgae composition can include 4-5 grams/acre. In some embodiments, the application rate of the dried microalgae composition can include 5-10 grams/acre.

EXAMPLES

Embodiments of the invention are exemplified and additional embodiments are disclosed in further detail in the following Examples, which are not in any way intended to limit the scope of any aspect of the invention described herein. The strain of microalgae identified as *Aurantiochytrium* sp. in some of the following examples was isolated from marine field samples (Mangrove, Fla. —Biscayne Bay) and sequenced for 18S. The sequences were compared with existing sequences on the National Center for Biotechnology Information (NCBI) GenBank database via Basic Local Alignment Search Tool (BLAST). The results of the sequence comparison showed strain's sequence is positioned between two species of the genus *Aurantiochytrium* (*Schizochytrium*), with the closest BLAST hits having a 98.8% similarity to *Aurantiochytrium* (*Schizochytrium*) *limacinum* SR21 (accession number AB973564.1). Therefore, this isolated microalgae strain is referred to in the examples as *Aurantiochytrium* sp.

Example 1—Fabaceae (Leguminosae)

Experiments are conducted to test effects of application of a microalgae based composition to crop plants of the family Fabaceae (Leguminosae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 2—Poaceae

Experiments are conducted to test effects of application of a microalgae based composition to crop plants of the family Poaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 3—Roasaceae

Experiments are conducted to test effects of application of a microalgae based composition to crop plants of the family Roasaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 4—Vitaceae

Experiments are conducted to test effects of application of a microalgae based composition to crop plants of the family Vitaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 5—Brassicaeae (Cruciferae)

Experiments are conducted to test effects of application of a microalgae based composition to crop plants of the family Brassicaeae (Cruciferae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including:

seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 6—Caricaceae

Experiments are conducted to test effects of application of a microalgae based composition to crop plants of the family Caricaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 7—Malvaceae

Experiments are conducted to test effects of application of a microalgae based composition to crop plants of the family Malvaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 8—Sapindaceae

Experiments are conducted to test effects of application of a microalgae based composition to crop plants of the family Sapindaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 9—Anacardiaceae

Experiments are conducted to test effects of application of a microalgae based composition to crop plants of the family Anacardiaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 10

An experiment was performed to determine the effect of treating *Arabidopsis thaliana* with a variety of treatments made from microalgae under normal growth conditions and under salt stressed conditions. The bioassay was initiated using four day old plantlets grown on half strength Murashige and Skoog (MS) medium, supplemented with 1% (w/v) sucrose, and solidified with 0.4% (w/v) Phytagel in square petri plates. Plates were vertically stacked in the growth chamber set at 22° C. with 16-h light/8-h dark cycle, with light intensity of 100 µmol/m$^{-2}$s$^{-1}$. Each plate contained five replicate plantlets. Plantlets were transferred onto medium supplemented with concentrations of 0.1% (0.1 mL/L), 0.01% (0.01 mL/L), or 0.001% (0.001 mL/L) of non-oil treatments, or 0.01% (0.01 mL/L), 0.001% (0.001 mL/L), or 0.0001% (0.0001 mL/L) of oil treatments listed in the table and compared to an untreated control. Each concentration of each treatment was tested in triplicate.

The organic carbon uses for culturing the *Chlorella* sp. biomass is specified in the tables below. All microalgae whole biomass treatments were prepared by lysing and freeze drying the biomass. For extracted biomass and extracted oil treatments (except for *Haematococcus*), the microalgal biomass (600 g) was mixed with a solvent (ethanol, hexane, or acetone) (3,000 mL) and heated at reflux for 2 hours. The reaction mixture was then filtered while hot and the biomass was extracted again with a solvent (ethanol, hexane, or acetone) twice (2 times at 3,000 mL). The combined organic extracts from the process were concentrated to yield the extracted oil, and the resulting extracted biomass was free dried. For *Haematococcus*, the extracted oil treatment was obtained by subjecting the biomass to a super critical carbon dioxide extraction. For the high lipid *Nannochloropsis* treatments, the cells were harvested during the oil or stationary phase when the metabolic activity was primarily lipid accumulation and not cell growth (e.g., cell division). In one treatment of *Aurantiochytrium*, the oil was extracted without using a solvent (i.e., mechanical separation of the oil from the biomass).

For the *Galdieria* protein fraction treatment, *Galdieria* biomass (100 g) was added to 1,000 mL of water and was heated to 50° C. for 4 hours. The reaction mixture was cooled and centrifuged at 6,000 rpm for 15 minutes at 4° C. The crude pellet was isolated and freeze dried to form the low protein whole biomass treatment. Next ammonium sulfate was added to the supernatant (30% saturation). The resulting solution was stirred at room temperature for 2 hours and centrifuged at 6,000 rpm for 30 minutes. The supernatant solution was then saturated with ammonium sulfate a second time (30% saturation). The results solution was stirred at room temperature for 2 hours and centrifuged at 6,000 rpm for 30 minutes. The pellet obtained was isolated and diluted water (about 200 mL) and purified by ultrafiltration to remove soluble salts. The resulting solution was collected and freeze dried to produce the protein fraction. The resulting *Galdieria* biomass that was subjected to the protein extraction had less than 15% protein. The low protein whole biomass was subjected to the oil extraction method described above using ethanol to produce the low protein extracted oil and low protein extracted biomass treatments. The resulting *Galdieria* biomass that was subjected to the protein extraction and oil extraction had less than 20% protein.

For the *Porphyridium* EPS treatments, first the *Porphyridium* culture broth was centrifuged to remove the microalgae biomass. Next the supernatant was diluted with isopropanol (3 to 5 times v/v) to precipitate the EPS. The precipitated EPS was then separated from the supernatant by filtration. The "PE rich fraction" *Porphyridium* treatment was produced by lysing the biomass and subjecting the lysed biomass at a concentration of 10% solids (w/v) to a water based extraction at 50° C. for 4 hours. The resulting solution was then diluted with water (10×) and centrifuged to produce the "PE rich fraction" liquid fraction and the "PEG 1 Lipid+EPS fraction". The "PE rich fraction" was purified using tangential flow filtration and freeze dried, resulting in a final concentration of 20-25% phycoerythrin. The "PEG 1 Lipid+EPS fraction" *Porphyridium* treatment contained primarily lipids, EPS, and water insoluble (non-extractable) protein. To produce the "LEB2+EPS" *Porphyridium* treatment, the "PEG 1 Lipid+EPS fraction" was refluxed in hexane and the lipids were extracted. The remaining solid fraction primarily comprised of EPS and protein.

The "Biomass—EPS" *Porphyridium* treatment was produced by centrifuging the culture to separate the EPS from the biomass, diluting the concentrated biomass with water (10-20×) and centrifuging a second time to remove additional EPS and salt (about 90-95%) from the resulting biomass used as the treatment. To produce the "PEB2 Lipid+PS fraction" *Porphyridium* treatment, "Biomass—EPS" fraction at a concentration of 5% solids (w/v) was subjected to a water based extraction at 50° C. for 4 hours. The resulting solution was centrifuged, and the supernatant was separated from the sediment. The supernatant was then brought to 25% saturation using ammonium sulfate to precipitate proteins that were then removed by centrifugation. The supernatant was then brought to 50% saturating using ammonium sulfate to precipitate the phycoerythrin. The precipitated phycoerythrin was collected by centrifugation, purified via dialysis using a 30 kDa filter, and freeze dried to produce the final form of the "PEB2 Lipid+PS fraction" *Porphyridium* treatment which contained 20-25% phycoerythrin.

For the *Spirulina* low protein and protein fraction treatments, the aqueous extract method as described above for *Galdieria* was performed. The resulting *Spirulina* biomass that was subjected to a protein extraction had less than 15% protein. The *Spirulina* lyzed whole biomass treatment was formed by mechanically disrupted the cells but then performing no further separations with or without solvents.

The salt stressed plantlets were also supplemented with 100 mM of NaCl. Seven days after the plantlets were treated plant dry weight, root length, amount of chlorotic leaves, and the amount of plants with chlorosis were measured. The results are shown in Tables 1-3, which display the results for each tested concentration with respect to the untreated control. For chlorosis metric, the reduction in the effect of chlorosis with respect to the control (i.e., improvement over the control) is represented as a negative (−) value.

TABLE 1

| Growth (No Salt Stress) | | | | |
| --- | --- | --- | --- | --- |
| Genus | Treatment | Concentration | Dry Weight % Difference vs. Control | Root Length % Difference vs. Control |
| Galdieria | Whole Biomass | 0.1% | −38.2 | −81.0 |
| | | 0.01% | −30.0 | −6.4 |
| | | 0.001% | −40.6 | +4.0 |
| Galdieria | Extracted Biomass | 0.1% | −52.1 | −27.0 |
| | | 0.01% | −20.6 | −4.7 |
| | | 0.001% | −37.0 | −3.2 |
| Galdieria | Extracted Oil | 0.01% | −57.0 | −77.8 |
| | | 0.001% | −24.7 | −29.6 |
| | | 0.0001% | −45.2 | +6.9 |

TABLE 1-continued

Growth (No Salt Stress)

| Genus | Treatment | Concentration | Dry Weight % Difference vs. Control | Root Length % Difference vs. Control |
|---|---|---|---|---|
| Galdieria | Low Protein Whole Biomass | 0.1% 0.01% 0.001% | −23.6 −8.5 +7.3 | −63.6 +9.7 −11.0 |
| Galdieria | Low Protein Extracted Biomass | 0.1% 0.01% 0.001% | −73.9 −46.7 −41.8 | −62.0 −31.8 −10.6 |
| Galdieria | Low Protein Extracted Oil | 0.01% 0.001% 0.0001% | −58.1 +38.7 +21.5 | −97.2 −37.8 −3.9 |
| Galdieria | Protein Fraction | 0.1% 0.01% 0.001% | −37.6 −26.1 −9.7 | −30.3 −14.6 −5.3 |
| Chlorella sp. (acetate) | Whole Biomass | 0.1% 0.01% 0.001% | −27.3 +40.0 +21.8 | −100.0 +3.0 −6.0 |
| Chlorella sp. (acetate) | Extracted Biomass | 0.1% 0.01% 0.001% | +9.1 +32.7 +36.4 | −99.6 −20.0 −30.8 |
| Chlorella sp. (acetate) | Extracted Oil | 0.01% 0.001% 0.0001% | −32.4 −23.8 −4.8 | −63.4 −7.7 +23.7 |
| Haematococcus | Whole Biomass | 0.1% 0.01% 0.001% | −49.1 −23.6 −40.0 | −98.8 −8.4 +11.5 |
| Haematococcus | Extracted Biomass | 0.1% 0.01% 0.001% | −3.6 +50.9 +27.3 | −82.9 +1.9 +9.6 |
| Haematococcus | Extracted Oil | 0.01% 0.001% 0.0001% | −22.6 −10.8 −2.2 | −71.9 −24.9 −13.8 |
| Isochrysis | Whole Biomass | 0.1% 0.01% 0.001% | −52.1 −14.5 −30.2 | −99.4 +1.3 +6.1 |
| Isochrysis | Extracted Biomass | 0.1% 0.01% 0.001% | −43.6 +41.8 +94.5 | −100.0 +14.9 +12.0 |
| Isochrysis | Extracted Oil | 0.01% 0.001% 0.0001% | −33.3 +9.5 −16.2 | −17.9 +17.3 +0.2 |
| Nannochloropsis | Extracted Biomass | 0.1% 0.01% 0.001% | +16.4 +41.8 +69.1 | −12.3 +21.4 +7.9 |
| Nannochloropsis | Extracted Oil | 0.01% 0.001% 0.0001% | −9.5 +1.9 −29.4 | −57.6 −10.7 +22.1 |
| Porphyridium | Whole Biomass | 0.1% 0.01% 0.001% | −38.8 −14.5 −20.6 | −39.4 −5.0 −3.2 |
| Porphyridium | Extracted Biomass | 0.1% 0.01% 0.001% | −47.3 −30.3 −21.8 | −78.9 −10.3 −4.3 |
| Porphyridium | Extracted Oil | 0.01% 0.001% 0.0001% | −16.1 +1.1 −16.1 | −15.8 −21.7 +2.1 |
| Porphyridium | EPS | 0.1% 0.01% 0.001% | — +27.3 +41.8 | — −87.2 +14.3 |
| Schizochytrium | Whole Biomass | 0.1% 0.01% 0.001% | −61.2 −37.6 −38.2 | −99.8 −78.5 −16.5 |
| Schizochytrium | Extracted Biomass | 0.1% 0.01% 0.001% | +27.3 +63.6 +40.0 | −88.9 +5.2 +15.2 |
| Schizochytrium | Extracted Oil | 0.01% 0.001% 0.0001% | +3.2 −6.7 −19.0 | −10.8 +2.6 +31.7 |
| Tetraselmis | Whole Biomass | 0.1% 0.01% 0.001% | −53.3 −29.1 −15.8 | −100.0 −17.9 +4.8 |
| Tetraselmis | Extracted Biomass | 0.1% 0.01% 0.001% | −67.9 −18.8 −12.7 | −100.0 −1.4 +15.7 |
| Tetraselmis | Extracted Oil | 0.01% 0.001% 0.0001% | −32.3 −14.0 −2.2 | −89.0 −33.9 −24.7 |
| Pavlova | Whole Biomass | 0.1% 0.01% 0.001% | −63.4 −44.7 −31.7 | −100.0 −61.4 −48.7 |
| Pavlova | Extracted Biomass | 0.1% 0.01% 0.001% | +73.9 +131.5 +118 | — +159.0 +175.3 |
| Pavlova | Extracted Oil | 0.01% 0.001% 0.0001% | +18.1 +18.7 +26.3 | +10.6 +11.3 +10.9 |
| Phaeodactylum | Whole Biomass | 0.1% 0.01% 0.001% | −38.9 −29.5 +42.1 | −90.6 +1.0 +26.9 |
| Phaeodactylum | Extracted Biomass | 0.1% 0.01% 0.001% | — +70.3 +148.6 | — +21.9 +57.6 |
| Phaeodactylum | Extracted Oil | 0.01% 0.001% 0.0001% | −46.5 −48.5 −46.5 | −3.9 −11.1 −0.6 |
| Nannochloropsis | High Lipid Whole Biomass | 0.1% 0.01% 0.001% | −31.9 −22.5 −22.1 | −95.6 −26.1 −26.0 |
| Nannochloropsis | High Lipid Extracted Biomass | 0.1% 0.01% 0.001% | −54.0 −30.5 −9.1 | +46.6 +28.4 +0.4 |
| Nannochloropsis | High Lipid Extracted Oil | 0.01% 0.001% 0.0001% | −15.8 −13.7 −22.1 | +5.1 +1.0 +7.3 |
| Porphyridium | PE rich fraction | 0.1% 0.01% 0.001% | −67.4 −56.3 −46.3 | −47.9 +40.0 +46.8 |
| Porphyridium | PEB 1 lipid + EPS fraction | 0.1% 0.01% 0.001% | −59.1 −36.3 −23.4 | −33.2 +0.6 +0.7 |
| Porphyridium | Extracted Oil | 0.01% 0.001% 0.0001% | — — — | −100.0 −15.8 +2.3 |
| Porphyridium | LEB2 + EPS | 0.1% 0.01% 0.001% | −69.7 −52.9 −17.3 | −78.7 +0.3 −2.2 |
| Porphyridium | Biomass − EPS | 0.1% 0.01% 0.001% | −45.9 −27.6 −26.3 | −6.1 +5.8 +0.7 |
| Porphyridium | PE rich fraction from biomass − EPS | 0.1% 0.01% 0.001% | −41.5 −33.9 −7.6 | −93.2 −1.5 +5.0 |
| Porphyridium | PEB 2 Lipid + PS fraction | 0.1% 0.01% 0.001% | −59.1 −11.7 −15.8 | −100.0 −5.7 +13.1 |
| Aurantiochytrium sp. | Whole Biomass | 0.1% 0.01% 0.001% | −44.4 −8.9 −4.8 | −90.7 −8.8 −0.6 |
| Aurantiochytrium sp. | Extracted Biomass (hexane) | 0.1% 0.01% 0.001% | −61.8 −44.4 +2.2 | −14.2 +15.1 +17.6 |
| Aurantiochytrium sp. | Extracted Oil (hexane) | 0.01% 0.001% 0.0001% | −15.9 +3.0 −3.0 | +8.0 −6.7 +16.1 |
| Aurantiochytrium sp. | Extracted Biomass (ethanol) | 0.1% 0.01% 0.001% | −46.2 −6.2 −0.9 | −83.4 −2.6 −0.4 |
| Aurantiochytrium sp. | Extracted Oil (ethanol) | 0.01% 0.001% 0.0001% | −18.3 −43.3 −23.3 | +8.0 −6.7 +16.1 |
| Aurantiochytrium sp. | Extracted Oil (mechanical) | 0.01% 0.001% 0.0001% | −11.1 −0.4 −28.9 | +10.6 −4.0 +6.8 |
| Spirulina | Extracted Biomass (hexane) | 0.1% 0.01% 0.001% | −35.1 −46.7 +4.7 | −93.6 +1.6 +2.2 |

TABLE 1-continued

Growth (No Salt Stress)

| Genus | Treatment | Concentration | Dry Weight % Difference vs. Control | Root Length % Difference vs. Control |
|---|---|---|---|---|
| Spirulina | Extracted Oil (hexane) | 0.01% | −7.0 | −58.0 |
|  |  | 0.001% | +13.7 | −9.9 |
|  |  | 0.0001% | +32.8 | +4.1 |
| Spirulina | Extracted Biomass (acetone) | 0.1% | −77.8 | −100.0 |
|  |  | 0.01% | −17.3 | +18.7 |
|  |  | 0.001% | −22.7 | −2.2 |
| Spirulina | Extracted Oil (acetone) | 0.1% | −37.4 | −77.4 |
|  |  | 0.001% | −13.0 | +3.1 |
|  |  | 0.0001% | +22.6 | +14.7 |
| Spirulina | Low Protein Whole Biomass | 0.1% | −79.1 | −88.2 |
|  |  | 0.01% | −56.4 | −18.9 |
|  |  | 0.001% | −29.3 | +1.2 |
| Spirulina | Protein Fraction | 0.1% | +36.4 | +13.8 |
|  |  | 0.01% | −4.9 | +10.8 |
|  |  | 0.001% | −18.7 | +7.7 |
| Spirulina | Lyzed Whole Biomass | 0.1% | −15.2 | −20.6 |
|  |  | 0.01% | +6.3 | +36.5 |
|  |  | 0.001% | −9.6 | +15.6 |
| Scenedesmus | Whole Biomass | 0.1% | −58.2 |  |
|  |  | 0.01% | −37.7 |  |
|  |  | 0.001% | −21.8 |  |
| Scenedesmus | Extracted Biomass | 0.1% | −32.8 |  |
|  |  | 0.01% | −28.1 |  |
|  |  | 0.001% | −25.8 |  |
| Scenedesmus | Extracted Oil | 0.01% | −58.7 |  |
|  |  | 0.001% | −35.8 |  |
|  |  | 0.0001% | −32.3 |  |
| T-Isochrysis | Whole Biomass | 0.1% | −58.9 |  |
|  |  | 0.01% | −31.6 |  |
|  |  | 0.001% | −10.2 |  |
| T-Isochrysis | Extracted Biomass (ethanol) | 0.1% | −55.2 |  |
|  |  | 0.01% | +7.8 |  |
|  |  | 0.001% | +23.5 |  |
| T-Isochrysis | Extracted Oil (ethanol) | 0.1% | −42.1 |  |
|  |  | 0.001% | −6.0 |  |
|  |  | 0.0001% | +9.9 |  |
| Chlorella zofingiensis | Whole Biomass | 0.1% | −54.0 |  |
|  |  | 0.01% | −30.0 |  |
|  |  | 0.001% | −1.8 |  |
| Chlorella zofingiensis | Extracted Biomass (ethanol) | 0.1% | −36.5 |  |
|  |  | 0.01% | −6.2 |  |
|  |  | 0.001% | −3.6 |  |
| Chlorella zofingiensis | Extracted Oil (ethanol) | 0.01% | −34.7 |  |
|  |  | 0.001% | −12.0 |  |
|  |  | 0.0001% | −6.4 |  |
| Chlorella sp. (glucose) | Whole Biomass | 0.1% | −43.5 |  |
|  |  | 0.01% | −5.5 |  |
|  |  | 0.001% | +21.1 |  |
| Chlorella sp. (glucose) | Extracted Biomass (ethanol) | 0.1% | +11.6 |  |
|  |  | 0.01% | +13.6 |  |
|  |  | 0.001% | +42.9 |  |
| Chlorella sp. (glucose) | Extracted Oil (ethanol) | 0.01% | −42.7 |  |
|  |  | 0.001% | −28.7 |  |
|  |  | 0.0001% | −10.2 |  |
| Aurantiochytrium sp. | Whole Biomass (Medium Lipid) | 0.1% | −80.0 |  |
|  |  | 0.01% | −66.6 |  |
|  |  | 0.001% | −33.5 |  |
| Aurantiochytrium sp. | Extracted Biomass (High Lipid) (Mechanical Extraction) | 0.1% | −69.9 |  |
|  |  | 0.01% | −24.5 |  |
|  |  | 0.001% | +7.1 |  |
| Aurantiochytrium sp. | Extracted Oil (High Lipid) (Hexane) | 0.01% | −37.7 |  |
|  |  | 0.001% | −15.3 |  |
|  |  | 0.0001% | −38.0 |  |
| Aurantiochytrium sp. | Extracted Oil (High Lipid) (Ethanol) | 0.01% | +1.7 |  |
|  |  | 0.001% | −4.0 |  |
|  |  | 0.0001% | −10.8 |  |
| Aurantiochytrium sp. | Extracted Oil (High Lipid) (Mechanical Extraction) | 0.01% | −27.7 |  |
|  |  | 0.001% | −21.2 |  |
|  |  | 0.0001% | −31.6 |  |
| Aurantiochytrium sp. | Extracted Oil (Medium Lipid) (Hexane) | 0.01% | −40.2 |  |
|  |  | 0.001% | −38.5 |  |
|  |  | 0.0001% | −39.7 |  |
| Aurantiochytrium sp. | Extracted Oil (Medium Lipid) (Ethanol) | 0.01% | −52.2 |  |
|  |  | 0.001% | −25.7 |  |
|  |  | 0.0001% | −32.5 |  |
| Aurantiochytrium sp. | Extracted Biomass (Medium Lipid) (Hexane) | 0.1% | −55.7 |  |
|  |  | 0.01% | −16.1 |  |
|  |  | 0.001% | −14.1 |  |
| Aurantiochytrium sp. | Extracted Biomass (Medium Lipid) (Ethanol) | 0.1% | −25.4 |  |
|  |  | 0.01% | −24.4 |  |
|  |  | 0.001% | −11.4 |  |
| Aurantiochytrium sp. | Whole Biomass (High Lipid) | 0.1% | −65.5 |  |
|  |  | 0.01% | −13.1 |  |
|  |  | 0.001% | +0.4 |  |
| Aurantiochytrium sp. | Extracted Biomass (High Lipid) (Ethanol) | 0.1% | −36.2 |  |
|  |  | 0.01% | −10.1 |  |
|  |  | 0.001% | +1.4 |  |
| Aurantiochytrium sp. | Extracted Biomass (High Lipid) (Hexane) | 0.1% | −54.9 |  |
|  |  | 0.01% | −29.1 |  |
|  |  | 0.001% | +32.0 |  |
| Botryococcus | Lyzed Whole Biomass | 0.1% | −55.7 |  |
|  |  | 0.01% | −31.5 |  |
|  |  | 0.001% | −24.0 |  |
| Botryococcus | Extracted Oil | 0.01% | −44.1 |  |
|  |  | 0.001% | −22.2 |  |
|  |  | 0.0001% | −11.2 |  |
| Botryococcus | Extracted Biomass | 0.1% | −45.2 |  |
|  |  | 0.01% | −31.7 |  |
|  |  | 0.001% | −28.6 |  |

TABLE 2

Salt Stress

| Genus | Treatment | Concentration | Dry Weight % Difference vs. Control | Root Length % Difference vs. Control |
|---|---|---|---|---|
| Galdieria | Whole Biomass | 0.1% | −25.0 | −100.0 |
|  |  | 0.01% | −38.2 | −15.6 |
|  |  | 0.001% | −43.1 | −22.0 |
| Galdieria | Extracted Biomass | 0.1% | −20.6 | −35.2 |
|  |  | 0.01% | −13.7 | −3.0 |
|  |  | 0.001% | −50.0 | −20.7 |
| Galdieria | Extracted Oil | 0.1% | −41.7 | −48.1 |
|  |  | 0.01% | −38.3 | −37.4 |
|  |  | 0.0001% | −34.5 | −11.8 |
| Galdieria | Low Protein Whole Biomass | 0.1% | −35.3 | −98.3 |
|  |  | 0.01% | −51.0 | −26.6 |
|  |  | 0.001% | −36.3 | −10.9 |
| Galdieria | Low Protein Extracted Biomass | 0.1% | −32.4 | −35.4 |
|  |  | 0.01% | −20.6 | −17.5 |
|  |  | 0.001% | −28.4 | −9.0 |
| Galdieria | Low Protein Extracted Oil | 0.01% | −63.3 | −96.9 |
|  |  | 0.001% | −45.0 | −21.1 |
|  |  | 0.0001% | −21.7 | −56.5 |
| Galdieria | Protein Fraction | 0.1% | −8.8 | −33.4 |
|  |  | 0.01% | −29.4 | −22.6 |
|  |  | 0.001% | −22.5 | −22.9 |
| Chlorella sp. (acetate) | Whole Biomass | 0.1% | −22.4 | −96.3 |
|  |  | 0.01% | +47.1 | −33.7 |
|  |  | 0.001% | +47.1 | +17.7 |

TABLE 2-continued

Salt Stress

| Genus | Treatment | Concentration | Dry Weight % Difference vs. Control | Root Length % Difference vs. Control |
|---|---|---|---|---|
| Chlorella sp. (acetate) | Extracted Biomass | 0.1% | −11.8 | −100.0 |
| | | 0.01% | +26.5 | −80.9 |
| | | 0.001% | −20.6 | +15.3 |
| Chlorella sp. (acetate) | Extracted Oil | 0.01% | −9.6 | −42.8 |
| | | 0.001% | −22.8 | +0.5 |
| | | 0.0001% | −2.1 | +31.7 |
| Haematococcus | Whole Biomass | 0.1% | −81.7 | +0.6 |
| | | 0.01% | −75.0 | −23.0 |
| | | 0.001% | −35.0 | +2.6 |
| Haematococcus | Extracted Biomass | 0.1% | +8.8 | −96.4 |
| | | 0.01% | −2.9 | +2.8 |
| | | 0.001% | −20.6 | +26.7 |
| Haematococcus | Extracted Oil | 0.01% | −28.4 | −100.0 |
| | | 0.001% | −30.4 | −15.5 |
| | | 0.0001% | −5.9 | +8.4 |
| Isochrysis | Whole Biomass | 0.1% | — | −99.8 |
| | | 0.01% | −19.6 | −56.4 |
| | | 0.001% | −30.4 | −12.8 |
| Isochrysis | Extracted Biomass | 0.1% | −11.8 | −91.5 |
| | | 0.01% | +29.4 | −61.2 |
| | | 0.001% | +26.5 | +5.1 |
| Isochrysis | Extracted Oil | 0.01% | −28.4 | −63.5 |
| | | 0.001% | −19.0 | +15.8 |
| | | 0.0001% | −15.3 | +58.2 |
| Nannochloropsis | Extracted Biomass | 0.1% | +44.1 | −87.1 |
| | | 0.01% | +50.0 | +5.3 |
| | | 0.001% | +32.4 | +36.8 |
| Nannochloropsis | Extracted Oil | 0.01% | +31.8 | −30.3 |
| | | 0.001% | +9.2 | +37.3 |
| | | 0.0001% | +28.1 | +55.0 |
| Porphyridium | Whole Biomass | 0.1% | −34.3 | −87.2 |
| | | 0.01% | −9.8 | −3.6 |
| | | 0.001% | −28.4 | −3.8 |
| Porphyridium | Extracted Biomass | 0.1% | −26.5 | −55.6 |
| | | 0.01% | −20.6 | −26.5 |
| | | 0.001% | −14.7 | −16.4 |
| Porphyridium | Extracted Oil | 0.01% | −55.0 | −90.9 |
| | | 0.001% | −31.7 | −6.0 |
| | | 0.0001% | −55.0 | −5.2 |
| Porphyridium | EPS | 0.1% | — | — |
| | | 0.01% | +32.4 | −67.8 |
| | | 0.001% | +8.8 | +35.7 |
| Schizochytrium | Whole Biomass | 0.1% | −45.1 | −100.0 |
| | | 0.01% | −50.0 | −92.0 |
| | | 0.001% | −48.0 | −35.0 |
| Schizochytrium | Extracted Biomass | 0.1% | +38.2 | −100.0 |
| | | 0.01% | +8.8 | −2.6 |
| | | 0.001% | −2.9 | +10.9 |
| Schizochytrium | Extracted Oil | 0.01% | +46.9 | −17.1 |
| | | 0.001% | +49.7 | +6.3 |
| | | 0.0001% | +24.3 | +25.8 |
| Tetraselmis | Whole Biomass | 0.1% | −39.7 | −96.2 |
| | | 0.01% | −32.2 | −68.1 |
| | | 0.001% | −31.2 | −17.4 |
| Tetraselmis | Extracted Biomass | 0.1% | −55.9 | −95.7 |
| | | 0.01% | −20.6 | −68.0 |
| | | 0.001% | −16.7 | −8.9 |
| Tetraselmis | Extracted Oil | 0.01% | −81.7 | −83.3 |
| | | 0.001% | −16.7 | +1.6 |
| | | 0.0001% | −1.7 | −40.7 |
| Pavlova | Whole Biomass | 0.1% | −66.7 | −100.0 |
| | | 0.01% | −55.6 | −95.3 |
| | | 0.001% | −53.3 | −64.7 |
| Pavlova | Extracted Biomass | 0.1% | 0.0 | −98.5 |
| | | 0.01% | −27.1 | −71.7 |
| | | 0.001% | +34.4 | +6.0 |
| Pavlova | Extracted Oil | 0.01% | +15.2 | −5.5 |
| | | 0.001% | +5.1 | +6.2 |
| | | 0.0001% | −16.2 | −2.9 |
| Phaeodactylum | Whole Biomass | 0.1% | +26.3 | −100.0 |
| | | 0.01% | −30.0 | −41.7 |
| | | 0.001% | +1.3 | +12.4 |
| Phaeodactylum | Extracted Biomass | 0.1% | — | — |
| | | 0.01% | +129.2 | −73.8 |
| | | 0.001% | +175.0 | +37.0 |
| Phaeodactylum | Extracted Oil | 0.01% | −90.9 | −12.8 |
| | | 0.001% | −75.8 | +12.7 |
| | | 0.0001% | −53.5 | +38.3 |
| Nannochloropsis | High Lipid Whole Biomass | 0.1% | −37.5 | −94.1 |
| | | 0.01% | −52.5 | −16.2 |
| | | 0.001% | −25.0 | +53.8 |
| Nannochloropsis | High Lipid Extracted Biomass | 0.1% | −5.0 | +53.8 |
| | | 0.01% | −46.7 | +59.1 |
| | | 0.001% | −25.8 | +98.8 |
| Nannochloropsis | High Lipid Extracted Oil | 0.1% | +20.2 | +25.6 |
| | | 0.001% | −14.1 | −6.3 |
| | | 0.0001% | −2.0 | +6.7 |
| Porphyridium | PE rich fraction | 0.1% | −12.1 | −25.1 |
| | | 0.01% | −1.7 | +6.3 |
| | | 0.001% | −48.3 | −4.2 |
| Porphyridium | PEB 1 lipid + EPS fraction | 0.1% | −8.1 | −59.9 |
| | | 0.01% | +11.1 | +7.8 |
| | | 0.001% | −11.1 | +22.5 |
| Porphyridium | Extracted Oil | 0.01% | — | −78.9 |
| | | 0.001% | — | +4.2 |
| | | 0.0001% | — | +23.7 |
| Porphyridium | LEB2 + EPS | 0.1% | −14.1 | −91.5 |
| | | 0.01% | −25.3 | −1.7 |
| | | 0.001% | −41.4 | +16.0 |
| Porphyridium | Biomass − EPS | 0.1% | −63.6 | +17.1 |
| | | 0.01% | −70.7 | +24.5 |
| | | 0.001% | −49.5 | +24.5 |
| Porphyridium | PE rich fraction from biomass − EPS | 0.1% | −43.4 | −100.0 |
| | | 0.01% | −47.5 | +24.9 |
| | | 0.001% | −59.6 | +8.3 |
| Porphyridium | PEB 2 Lipid + PS fraction | 0.1% | −24.2 | −100.0 |
| | | 0.01% | −48.5 | −33.7 |
| | | 0.001% | −33.7 | +2.4 |
| Aurantiochytrium sp. | Whole Biomass | 0.1% | −21.1 | −96.8 |
| | | 0.01% | −29.4 | −4.0 |
| | | 0.001% | +12.2 | +29.0 |
| Aurantiochytrium sp. | Extracted Biomass (hexane) | 0.1% | +46.7 | +19.0 |
| | | 0.01% | +20.0 | +4.0 |
| | | 0.001% | +61.7 | +39.7 |
| Aurantiochytrium sp. | Extracted Oil (hexane) | 0.01% | −1.1 | −6.8 |
| | | 0.001% | −11.1 | −6.9 |
| | | 0.0001% | −4.4 | +9.6 |
| Aurantiochytrium sp. | Extracted Biomass (ethanol) | 0.1% | +13.3 | −100.0 |
| | | 0.01% | −30.0 | −25.8 |
| | | 0.001% | +18.3 | −1.8 |
| Aurantiochytrium sp. | Extracted Oil (ethanol) | 0.01% | +3.3 | −6.8 |
| | | 0.001% | −24.4 | −6.9 |
| | | 0.0001% | −12.1 | +9.6 |
| Aurantiochytrium sp. | Extracted Oil (mechanical) | 0.01% | −63.3 | +11.0 |
| | | 0.001% | −23.3 | +28.3 |
| | | 0.0001% | −42.8 | +15.3 |
| Spirulina | Extracted Biomass (hexane) | 0.1% | −16.7 | −100.0 |
| | | 0.01% | +27.5 | −23.2 |
| | | 0.001% | −13.3 | −19.5 |
| Spirulina | Extracted Oil (hexane) | 0.01% | −41.1 | −100.0 |
| | | 0.001% | +2.2 | −84.1 |
| | | 0.0001% | +31.7 | −47.8 |
| Spirulina | Extracted Biomass (acetone) | 0.1% | +1.7 | −92.9 |
| | | 0.01% | +16.7 | +5.3 |
| | | 0.001% | +50.0 | +23.3 |
| Spirulina | Extracted Oil (acetone) | 0.01% | −36.7 | −100.0 |
| | | 0.001% | −7.8 | −35.1 |
| | | 0.0001% | −23.3 | −17.9 |
| Spirulina | Low Protein Whole Biomass | 0.1% | −13.3 | −88.9 |
| | | 0.01% | −25.0 | −61.9 |
| | | 0.001% | −45.0 | −8.8 |
| Spirulina | Protein Fraction | 0.1% | −8.3 | +20.3 |
| | | 0.01% | +16.7 | +30.5 |
| | | 0.001% | +42.5 | +11.4 |

TABLE 2-continued

Salt Stress

| Genus | Treatment | Concentration | Dry Weight % Difference vs. Control | Root Length % Difference vs. Control |
|---|---|---|---|---|
| Spirulina | Lyzed Whole Biomass | 0.1% 0.01% 0.001% | −17.8 −33.3 −15.6 | −73.3 +7.0 +0.6 |
| Scenedesmus | Whole Biomass | 0.1% 0.01% 0.001% | +41.2 −26.6 −1.1 | |
| Scenedesmus | Extracted Biomass | 0.1% 0.01% 0.001% | +168.4 +1.7 −35.0 | |
| Scenedesmus | Extracted Oil | 0.01% 0.001% 0.0001% | +4.5 +35.6 −40.7 | |
| T-Isochrysis | Whole Biomass | 0.1% 0.01% 0.001% | +188.1 +137.3 +168.4 | |
| T-Isochrysis | Extracted Biomass (ethanol) | 0.1% 0.01% 0.001% | +66.7 +126.0 +29.9 | |
| T-Isochrysis | Extracted Oil (ethanol) | 0.01% 0.001% 0.0001% | +29.9 −1.1 +18.6 | |
| Chlorella zofingiensis | Whole Biomass | 0.1% 0.01% 0.001% | +111.9 −6.8 +10.2 | |
| Chlorella zofingiensis | Extracted Biomass (ethanol) | 0.1% 0.01% 0.001% | +92.1 +15.8 +15.8 | |
| Chlorella zofingiensis | Extracted Oil (ethanol) | 0.01% 0.001% 0.0001% | +21.5 +27.1 +89.3 | |
| Chlorella sp. (glucose) | Whole Biomass | 0.1% 0.01% 0.001% | −106.2 +75.1 +13.0 | |
| Chlorella sp. (glucose) | Extracted Biomass (ethanol) | 0.1% 0.01% 0.001% | +99.7 +59.7 +28.5 | |
| Chlorella sp. (glucose) | Extracted Oil (ethanol) | 0.01% 0.001% 0.0001% | +51.0 +2.4 +9.4 | |
| Aurantiochytrium sp. | Whole Biomass (Medium Lipid) | 0.1% 0.01% 0.001% | −84.4 −25.3 −9.7 | |
| Aurantiochytrium sp. | Extracted Biomass (High Lipid) (Mechanical Extraction) | 0.1% 0.01% 0.001% | −67.0 −27.1 +25.0 | |
| Aurantiochytrium sp. | Extracted Oil (High Lipid) (Hexane) | 0.01% 0.001% 0.0001% | +33.7 −9.7 +0.7 | |
| Aurantiochytrium sp. | Extracted Oil (High Lipid) (Ethanol) | 0.01% 0.001% 0.0001% | −4.5 −41.0 −61.8 | |
| Aurantiochytrium sp. | Extracted Oil (High Lipid) (Mechanical Extraction) | 0.01% 0.001% 0.0001% | −29.8 −50.9 −31.6 | |
| Aurantiochytrium sp. | Extracted Oil (Medium Lipid) (Hexane) | 0.01% 0.001% 0.0001% | −18.2 +5.1 −17.2 | |
| Aurantiochytrium sp. | Extracted Oil (Medium Lipid) (Ethanol) | 0.01% 0.001% 0.0001% | +6.1 −5.1 +5.1 | |
| Aurantiochytrium sp. | Extracted Biomass (Medium Lipid) (Hexane) | 0.1% 0.01% 0.001% | +20.2 +49.5 +30.3 | |
| Aurantiochytrium sp. | Extracted Biomass (Medium Lipid) (Ethanol) | 0.1% 0.01% 0.001% | +29.3 −1.0 +3.0 | |
| Aurantiochytrium sp. | Whole Biomass (High Lipid) | 0.1% 0.01% 0.001% | −49.5 −17.2 −19.2 | |
| Aurantiochytrium sp. | Extracted Biomass (High Lipid) (Ethanol) | 0.1% 0.01% 0.001% | +3.0 +20.2 +37.4 | |
| Aurantiochytrium sp. | Extracted Biomass (High Lipid) (Hexane) | 0.1% 0.01% 0.001% | −17.2 +20.2 +8.1 | |
| Botryococcus | Lyzed Whole Biomass | 0.1% 0.01% 0.001% | −9.4 −28.1 −28.8 | |
| Botryococcus | Extracted Oil | 0.01% 0.001% 0.0001% | −32.9 −35.0 −37.8 | |
| Botryococcus | Extracted Biomass | 0.1% 0.01% 0.001% | +15.5 −12.2 −7.3 | |

TABLE 3

Chlorosis

| Genus | Treatment | Concentration | Chlorotic leaves % Difference vs. Control | Plants with Chlorosis % Difference vs. Control |
|---|---|---|---|---|
| Galdieria | Whole Biomass | 0.1% 0.01% 0.001% | −0.5 −78.2 −26.4 | +25.8 −68.6 −21.4 |
| Galdieria | Extracted Biomass | 0.1% 0.01% 0.001% | +6.0 −48.6 −69.0 | +25.8 −26.6 −52.8 |
| Galdieria | Extracted Oil | 0.01% 0.001% 0.0001% | −11.1 0.0 +33.3 | −29.4 0.0 +35.3 |
| Galdieria | Low Protein Whole Biomass | 0.1% 0.01% 0.001% | +97.7 +31.9 +128.7 | +57.2 +41.5 +39.9 |
| Galdieria | Low Protein Extracted Biomass | 0.1% 0.01% 0.001% | −84.7 −44.0 −46.3 | −68.6 −26.6 −21.4 |
| Galdieria | Low Protein Extracted Oil | 0.01% 0.001% 0.0001% | −11.1 0.0 −33.3 | 0.0 −23.5 +58.8 |
| Galdieria | Protein Fraction | 0.1% 0.01% 0.001% | +7.9 −8.3 +39.4 | +25.8 −5.7 +36.3 |
| Chlorella sp. (acetate) | Whole Biomass | 0.1% 0.01% 0.001% | +47.2 −38.4 +14.4 | +46.7 +4.9 +25.8 |
| Chlorella sp. (acetate) | Extracted Biomass | 0.1% 0.01% 0.001% | +123.1 +51.9 +13.0 | +57.2 +46.7 +46.7 |
| Chlorella sp. (acetate) | Extracted Oil | 0.01% 0.001% 0.0001% | +55.6 +33.3 0.0 | +35.3 +17.6 −17.7 |
| Haematococcus | Whole Biomass | 0.1% 0.01% 0.001% | −8.8 −69.0 −27.8 | +15.3 −47.6 −16.2 |
| Haematococcus | Extracted Biomass | 0.1% 0.01% 0.001% | −59.8 −10.6 +34.7 | −39.1 +15.3 +57.2 |

TABLE 3-continued

Chlorosis

| Genus | Treatment | Concentration | Chlorotic leaves % Difference vs. Control | Plants with Chlorosis % Difference vs. Control |
|---|---|---|---|---|
| Haematococcus | Extracted Oil | 0.01% | +22.2 | −17.7 |
| | | 0.001% | +11.1 | −41.2 |
| | | 0.0001% | +44.4 | +58.8 |
| Isochrysis | Whole Biomass | 0.1% | +279.6 | +57.2 |
| | | 0.01% | −27.3 | +25.8 |
| | | 0.001% | −40.7 | −37.1 |
| Isochrysis | Extracted Biomass | 0.1% | +85.2 | +57.2 |
| | | 0.01% | +54.2 | +57.2 |
| | | 0.001% | +108.8 | +57.2 |
| Isochrysis | Extracted Oil | 0.01% | +44.4 | +64.7 |
| | | 0.001% | +55.6 | +29.4 |
| | | 0.0001% | +66.7 | +64.7 |
| Nannochloropsis | Extracted Biomass | 0.1% | +31.2 | +57.2 |
| | | 0.01% | +49.2 | +57.2 |
| | | 0.001% | +54.2 | +57.2 |
| Nannochloropsis | Extracted Oil | 0.01% | +66.7 | +29.4 |
| | | 0.001% | +33.3 | +11.8 |
| | | 0.0001% | +33.3 | +35.3 |
| Porphyridium | Whole Biomass | 0.1% | +13.0 | −16.2 |
| | | 0.01% | −17.6 | −5.7 |
| | | 0.001% | +15.7 | +57.2 |
| Porphyridium | Extracted Biomass | 0.1% | +59.3 | +46.7 |
| | | 0.01% | 0.0 | +36.3 |
| | | 0.001% | +33.8 | +57.2 |
| Porphyridium | Extracted Oil | 0.01% | +55.6 | +35.3 |
| | | 0.001% | +33.3 | +47.1 |
| | | 0.0001% | +22.2 | +41.2 |
| Porphyridium | EPS | 0.1% | — | — |
| | | 0.01% | +35.6 | +36.3 |
| | | 0.001% | +25.9 | +46.7 |
| Schizochytrium | Whole Biomass | 0.1% | +34.7 | +46.7 |
| | | 0.01% | +6.5 | +36.3 |
| | | 0.001% | −4.6 | +4.9 |
| Schizochytrium | Extracted Biomass | 0.1% | −25.5 | +15.3 |
| | | 0.01% | −33.3 | +16.2 |
| | | 0.001% | +2.3 | +15.3 |
| Schizochytrium | Extracted Oil | 0.01% | +44.4 | +52.9 |
| | | 0.001% | +33.3 | +29.4 |
| | | 0.0001% | −11.8 | −11.8 |
| Tetraselmis | Whole Biomass | 0.1% | +314.8 | +57.2 |
| | | 0.01% | +53.7 | −26.6 |
| | | 0.001% | −21.3 | +15.3 |
| Tetraselmis | Extracted Biomass | 0.1% | +223.6 | +44.2 |
| | | 0.01% | −2.3 | +15.3 |
| | | 0.001% | −65.3 | −58.0 |
| Tetraselmis | Extracted Oil | 0.01% | +22.2 | 0.0 |
| | | 0.001% | 0.0 | +23.5 |
| | | 0.0001% | +22.2 | −23.5 |
| Pavlova | Whole Biomass | 0.1% | +72.8 | +19.0 |
| | | 0.01% | +60.5 | +3.2 |
| | | 0.001% | +57.4 | +11.1 |
| Pavlova | Extracted Biomass | 0.1% | +44.6 | +33.3 |
| | | 0.01% | +8.4 | +6.7 |
| | | 0.001% | −8.4 | −2.3 |
| Pavlova | Extracted Oil | 0.01% | +50.3 | +45.8 |
| | | 0.001% | +30.3 | +56.3 |
| | | 0.0001% | +115.2 | +56.3 |
| Phaeodactylum | Whole Biomass | 0.1% | −42.5 | −41.7 |
| | | 0.01% | −29.9 | −25.0 |
| | | 0.001% | +11.5 | 0.0 |
| Phaeodactylum | Extracted Biomass | 0.1% | — | — |
| | | 0.01% | −44.6 | −20.0 |
| | | 0.001% | −61.1 | −46.7 |
| Phaeodactylum | Extracted Oil | 0.01% | +58.3 | +9.4 |
| | | 0.001% | +61.5 | +25.0 |
| | | 0.0001% | +37.4 | +14.6 |
| Nannochloropsis | High Lipid Whole Biomass | 0.1% | −40.2 | 0.0 |
| | | 0.01% | −77.0 | −75.0 |
| | | 0.001% | +1.1 | −25.0 |
| Nannochloropsis | High Lipid Extracted Biomass | 0.1% | −42.5 | −33.3 |
| | | 0.01% | +1.1 | 0.0 |
| | | 0.001% | −34.5 | −33.3 |
| Nannochloropsis | High Lipid Extracted Oil | 0.01% | −1.3 | +35.4 |
| | | 0.001% | +66.2 | +25.0 |
| | | 0.0001% | +9.4 | −16.7 |
| Porphyridium | PE rich fraction | 0.1% | −94.8 | −88.1 |
| | | 0.01% | −18.0 | −16.7 |
| | | 0.001% | −29.7 | −16.7 |
| Porphyridium | PEB 1 lipid + EPS fraction | 0.1% | −18.8 | −37.5 |
| | | 0.01% | +9.0 | −16.7 |
| | | 0.001% | −42.3 | −16.7 |
| Porphyridium | LEB2 + EPS | 0.1% | −92.5 | −79.2 |
| | | 0.01% | −10.9 | −37.5 |
| | | 0.001% | +9.0 | +14.6 |
| Porphyridium | Biomass − EPS | 0.1% | −10.9 | −6.2 |
| | | 0.01% | +13.7 | +25.0 |
| | | 0.001% | +88.0 | +4.2 |
| Porphyridium | PE rich fraction from biomass − EPS | 0.1% | +4.3 | −6.2 |
| | | 0.01% | +44.0 | +56.3 |
| | | 0.001% | −4.7 | +35.4 |
| Porphyridium | PEB 2 Lipid + PS fraction | 0.1% | −79.9 | −58.3 |
| | | 0.01% | −42.3 | −37.5 |
| | | 0.001% | +29.9 | +4.2 |
| Aurantiochytrium sp. | Whole Biomass | 0.1% | +44.5 | +22.2 |
| | | 0.01% | +57.5 | +66.7 |
| | | 0.001% | +39.9 | +31.0 |
| Aurantiochytrium sp. | Extracted Biomass (hexane) | 0.1% | +15.7 | +25.0 |
| | | 0.01% | +8.3 | −16.7 |
| | | 0.001% | −25.7 | 0.0 |
| Aurantiochytrium sp. | Extracted Oil (hexane) | 0.01% | −26.7 | −22.2 |
| | | 0.001% | −25.3 | −33.3 |
| | | 0.0001% | +9.6 | +44.4 |
| Aurantiochytrium sp. | Extracted Biomass (ethanol) | 0.1% | −33.9 | −8.3 |
| | | 0.01% | +17.9 | 0.0 |
| | | 0.001% | −6.8 | −8.3 |
| Aurantiochytrium sp. | Extracted Oil (ethanol) | 0.01% | −34.9 | +33.3 |
| | | 0.001% | −58.0 | −48.7 |
| | | 0.0001% | −10.3 | −22.2 |
| Aurantiochytrium sp. | Extracted Oil (mechanical) | 0.01% | −50.2 | −22.2 |
| | | 0.001% | −3.3 | +22.2 |
| | | 0.0001% | −52.7 | −11.1 |
| Spirulina | Extracted Biomass (hexane) | 0.1% | +63.7 | +55.6 |
| | | 0.01% | −6.0 | +11.1 |
| | | 0.001% | +74.0 | +66.7 |
| Spirulina | Extracted Oil (hexane) | 0.01% | +94.3 | +22.2 |
| | | 0.001% | +55.0 | +33.3 |
| | | 0.0001% | +28.8 | +22.2 |
| Spirulina | Extracted Biomass (acetone) | 0.1% | −0.6 | 0.0 |
| | | 0.01% | +21.9 | +8.3 |
| | | 0.001% | −23.4 | −8.3 |
| Spirulina | Extracted Oil (acetone) | 0.01% | +81.4 | +55.6 |
| | | 0.001% | −22.8 | −11.1 |
| | | 0.0001% | +39.5 | +11.1 |
| Spirulina | Low Protein Whole Biomass | 0.1% | −21.1 | −16.7 |
| | | 0.01% | −6.8 | −8.3 |
| | | 0.001% | −12.3 | 0.0 |
| Spirulina | Protein Fraction | 0.1% | −48.1 | −16.7 |
| | | 0.01% | −35.3 | −16.7 |
| | | 0.001% | +51.7 | +8.3 |
| Spirulina | Lyzed Whole Biomass | 0.1% | +122.3 | +66.7 |
| | | 0.01% | +41.3 | +33.3 |
| | | 0.001% | +56.1 | +54.8 |
| Scenedesmus | Whole Biomass | 0.1% | −24.1 | −5.8 |
| | | 0.01% | −4.6 | +8.7 |
| | | 0.001% | −27.0 | −5.8 |
| Scenedesmus | Extracted Biomass | 0.1% | −31.9 | −5.8 |
| | | 0.01% | +6.9 | +8.7 |
| | | 0.001% | +28.2 | +8.7 |
| Scenedesmus | Extracted Oil | 0.01% | −2.4 | −5.8 |
| | | 0.001% | +4.7 | +8.7 |
| | | 0.0001% | +34.2 | +8.7 |
| T-Isochrysis | Whole Biomass | 0.1% | −79.1 | −34.8 |
| | | 0.01% | −54.5 | −27.5 |
| | | 0.001% | −41.3 | −20.3 |

TABLE 3-continued

Chlorosis

| Genus | Treatment | Concentration | Chlorotic leaves % Difference vs. Control | Plants with Chlorosis % Difference vs. Control |
|---|---|---|---|---|
| T-*Isochrysis* | Extracted Biomass (ethanol) | 0.1% | −25.5 | +8.7 |
| | | 0.01% | −32.8 | +8.7 |
| | | 0.001% | +11.8 | +8.7 |
| T-*Isochrysis* | Extracted Oil (ethanol) | 0.01% | −21.0 | +1.4 |
| | | 0.001% | +17.8 | +8.7 |
| | | 0.0001% | +12.9 | +1.4 |
| *Chlorella zofingiensis* | Whole Biomass | 0.1% | −43.4 | −5.8 |
| | | 0.01% | +17.6 | +8.7 |
| | | 0.001% | +17.0 | +8.7 |
| *Chlorella zofingiensis* | Extracted Biomass (ethanol) | 0.1% | −23.7 | −5.8 |
| | | 0.01% | +2.1 | +1.4 |
| | | 0.001% | +13.3 | +8.7 |
| *Chlorella zofingiensis* | Extracted Oil (ethanol) | 0.01% | +14.0 | +8.7 |
| | | 0.001% | +23.7 | +8.7 |
| | | 0.0001% | −30.7 | −27.5 |
| *Chlorella* sp. (glucose) | Whole Biomass | 0.1% | −20.2 | −13.0 |
| | | 0.01% | +2.4 | −5.8 |
| | | 0.001% | +13.3 | +1.4 |
| *Chlorella* sp. (glucose) | Extracted Biomass (ethanol) | 0.1% | −49.2 | 0.0 |
| | | 0.01% | −48.2 | −8.3 |
| | | 0.001% | −22.8 | −8.3 |
| *Chlorella* sp. (glucose) | Extracted Oil (ethanol) | 0.01% | −39.0 | +16.7 |
| | | 0.001% | −13.6 | 0.0 |
| | | 0.0001% | −12.6 | −8.3 |
| *Aurantiochytrium* sp. | Whole Biomass (Medium Lipid) | 0.1% | +41.3 | +16.7 |
| | | 0.01% | −43.1 | +8.3 |
| | | 0.001% | −13.6 | +25.0 |
| *Aurantiochytrium* sp. | Extracted Biomass (High Lipid) (Mechanical Extraction) | 0.1% | −33.9 | 0.0 |
| | | 0.01% | −10.6 | +8.3 |
| | | 0.001% | −81.7 | −33.3 |
| *Aurantiochytrium* sp. | Extracted Oil (High Lipid) (Hexane) | 0.01% | −59.3 | −8.3 |
| | | 0.001% | −43.1 | +16.7 |
| | | 0.0001% | −41.7 | +8.3 |
| *Aurantiochytrium* sp. | Extracted Oil (High Lipid) (Ethanol) | 0.01% | −16.7 | 0.0 |
| | | 0.001% | +7.7 | +16.7 |
| | | 0.0001% | +28.0 | +16.7 |
| *Aurantiochytrium* sp. | Extracted Oil (High Lipid) (Mechanical Extraction) | 0.01% | +52.9 | 0.0 |
| | | 0.001% | +67.9 | 0.0 |
| | | 0.0001% | +40.8 | 0.0 |
| *Aurantiochytrium* sp. | Extracted Oil (Medium Lipid) (Hexane) | 0.01% | −11.2 | −16.7 |
| | | 0.001% | −28.8 | −9.7 |
| | | 0.0001% | −15.2 | −2.8 |
| *Aurantiochytrium* sp. | Extracted Oil (Medium Lipid) (Ethanol) | 0.01% | −42.6 | −23.6 |
| | | 0.001% | −20.4 | −9.7 |
| | | 0.0001% | −8.1 | −2.8 |
| *Aurantiochytrium* sp. | Extracted Biomass (Medium Lipid) (Hexane) | 0.1% | −61.7 | −9.7 |
| | | 0.01% | −68.1 | −37.5 |
| | | 0.001% | −64.9 | −44.3 |
| *Aurantiochytrium* sp. | Extracted Biomass (Medium Lipid) (Ethanol) | 0.1% | +2.8 | −2.8 |
| | | 0.01% | +30.2 | +4.2 |
| | | 0.001% | −9.1 | −2.8 |
| *Aurantiochytrium* sp. | Whole Biomass (High Lipid) | 0.1% | +61.7 | +4.2 |
| | | 0.01% | +8.2 | −2.8 |
| | | 0.001% | +5.4 | −2.8 |
| *Aurantiochytrium* sp. | Extracted Biomass (High Lipid) (Ethanol) | 0.1% | −46.4 | −2.8 |
| | | 0.01% | −33.2 | −9.7 |
| | | 0.001% | −24.3 | −2.8 |
| *Aurantiochytrium* sp. | Extracted Biomass (High Lipid) (Hexane) | 0.1% | −3.8 | +4.2 |
| | | 0.01% | −37.7 | −16.7 |
| | | 0.001% | −10.7 | +4.2 |
| *Botryococcus* | Lyzed Whole Biomass | 0.1% | −52.9 | −20.0 |
| | | 0.01% | −11.6 | 0.0 |
| | | 0.001% | −8.8 | −6.7 |
| *Botryococcus* | Extracted Oil | 0.01% | −35.6 | −6.7 |
| | | 0.001% | −0.7 | 0.0 |
| | | 0.0001% | −1.9 | 0.0 |
| *Botryococcus* | Extracted Biomass | 0.1% | −60.1 | −26.7 |
| | | 0.01% | −61.2 | −26.7 |
| | | 0.001% | −36.9 | 0.0 |

Example 11

An experiment was performed to determine the effect of treating *Arabidopsis thaliana* with a variety of microalgae based treatments under normal growth conditions and under salt stressed conditions. The bioassay was initiated using two week old *Arabidopsis* plants grown on Jiffy pellets (peat moss pellets). Five replicates of each plant were performed for the treatments. Plants on Jiffy pellets were placed on trays with concentrations of 0.1% (0.1 mL/L), 0.01% (0.01 mL/L), or 0.001% (0.001 mL/L) of non-oil treatments, or 0.01% (0.01 mL/L), 0.001% (0.001 mL/L), or 0.0001% (0.0001 mL/L) microalgae oil at 40 mL/plant and compared to an untreated control. The treatments were prepared as described in Example 10. The salt stressed plantlets were also supplemented with 150 mM of NaCl. Five days after the first treatment the microalgae based treatment was repeated, but additional salt was not added. Ten days after the first treatment the plant dry weight was measured. The results are shown in Tables 4-5, which display the results for each tested concentration with respect to the untreated control.

TABLE 4

Growth (No Salt Stress)

| Genus | Treatment | Concentration | Dry Weight % Difference vs. Control |
|---|---|---|---|
| *Galdieria* | Low Protein Extracted Biomass | 0.1% | +3.0 |
| | | 0.01% | +15.1 |
| | | 0.001% | +4.2 |
| *Galdieria* | Low Protein Extracted Oil | 0.01% | −12.6 |
| | | 0.001% | +7.8 |
| | | 0.0001% | +21.9 |
| *Galdieria* | Protein Fraction | 0.1% | −28.4 |
| | | 0.01% | −28.9 |
| | | 0.001% | +1.3 |
| *Chlorella* sp. (acetate) | Whole Biomass | 0.1% | −21.6 |
| | | 0.01% | +13.9 |
| | | 0.001% | +15.5 |
| *Haematococcus* | Extracted Biomass | 0.1% | −17.9 |
| | | 0.01% | +13.1 |
| | | 0.001% | +35.9 |
| *Isochrysis* | Extracted Biomass | 0.1% | −59.3 |
| | | 0.01% | −30.2 |
| | | 0.001% | −38.0 |
| *Nannochloropsis* | Extracted Biomass | 0.1% | −28.4 |
| | | 0.01% | −11.1 |
| | | 0.001% | −47.4 |
| *Schizochytrium* | Extracted Biomass | 0.1% | +44.2 |
| | | 0.01% | +94.3 |
| | | 0.001% | +65.0 |

TABLE 4-continued

Growth (No Salt Stress)

| Genus | Treatment | Concentration | Dry Weight % Difference vs. Control |
|---|---|---|---|
| Schizochytrium | Extracted Oil | 0.01% | −7.7 |
| | | 0.001% | +9.6 |
| | | 0.0001% | +16.6 |
| T-Isochrysis | Whole Biomass | 0.1% | −16.4 |
| | | 0.01% | +11.9 |
| | | 0.001% | +10.3 |
| T-Isochrysis | Extracted Biomass (ethanol) | 0.1% | +9.0 |
| | | 0.01% | +10.9 |
| | | 0.001% | +18.0 |
| Chlorella zofingiensis | Extracted Oil (ethanol) | 0.01% | −44.8 |
| | | 0.001% | −16.1 |
| | | 0.0001% | −22.3 |
| Chlorella sp. (glucose) | Whole Biomass | 0.1% | −43.7 |
| | | 0.01% | −22.1 |
| | | 0.001% | −34.3 |
| Chlorella sp. (glucose) | Extracted Biomass (ethanol) | 0.1% | −10.9 |
| | | 0.01% | +30.8 |
| | | 0.001% | +23.7 |
| Aurantiochytrium sp. | Extracted Oil (High Lipid) (Hexane) | 0.01% | −15.7 |
| | | 0.001% | +40.7 |
| | | 0.0001% | +33.8 |
| Aurantiochytrium sp. | Extracted Biomass (Medium Lipid) (Hexane) | 0.1% | −9.1 |
| | | 0.01% | +33.5 |
| | | 0.001% | +29.6 |
| Aurantiochytrium sp. | Extracted Biomass (High Lipid) (Ethanol) | 0.1% | +7.1 |
| | | 0.01% | +30.4 |
| | | 0.001% | +19.9 |

TABLE 5

Salt Stress

| Genus | Treatment | Concentration | Dry Weight % Difference vs. Control |
|---|---|---|---|
| Galdieria | Low Protein Extracted Biomass | 0.1% | −35.2 |
| | | 0.01% | +24.3 |
| | | 0.001% | −18.3 |
| Galdieria | Low Protein Extracted Oil | 0.01% | — |
| | | 0.001% | — |
| | | 0.0001% | — |
| Galdieria | Protein Fraction | 0.1% | −40.2 |
| | | 0.01% | −9.7 |
| | | 0.001% | −24.0 |
| Chlorella sp. (acetate) | Whole Biomass | 0.1% | −27.0 |
| | | 0.01% | −3.9 |
| | | 0.001% | +6.4 |
| Haematococcus | Extracted Biomass | 0.1% | −18.3 |
| | | 0.01% | +27.3 |
| | | 0.001% | +30.5 |
| Isochrysis | Extracted Biomass | 0.1% | −60.5 |
| | | 0.01% | −24.6 |
| | | 0.001% | −25.0 |
| Nannochloropsis | Extracted Biomass | 0.1% | −28.8 |
| | | 0.01% | −21.1 |
| | | 0.001% | −33.3 |
| Schizochytrium | Extracted Biomass | 0.1% | — |
| | | 0.01% | — |
| | | 0.001% | — |
| Schizochytrium | Extracted Oil | 0.01% | −22.1 |
| | | 0.001% | +20.4 |
| | | 0.0001% | −3.0 |
| T-Isochrysis | Whole Biomass | 0.1% | −19.3 |
| | | 0.01% | +13.0 |
| | | 0.001% | +1.3 |
| T-Isochrysis | Extracted Biomass (ethanol) | 0.1% | −27.6 |
| | | 0.01% | +2.7 |
| | | 0.001% | −16.3 |

TABLE 5-continued

Salt Stress

| Genus | Treatment | Concentration | Dry Weight % Difference vs. Control |
|---|---|---|---|
| Chlorella zofingiensis | Extracted Oil (ethanol) | 0.01% | −55.0 |
| | | 0.001% | −34.5 |
| | | 0.0001% | −27.0 |
| Chlorella sp. (glucose) | Whole Biomass | 0.1% | −64.9 |
| | | 0.01% | −46.4 |
| | | 0.001% | −29.4 |
| Chlorella sp. (glucose) | Extracted Biomass (ethanol) | 0.1% | −43.4 |
| | | 0.01% | −20.3 |
| | | 0.001% | −23.8 |
| Aurantiochytrium sp. | Extracted Oil (High Lipid) (Hexane) | 0.01% | −26.9 |
| | | 0.001% | +23.7 |
| | | 0.0001% | +48.0 |
| Aurantiochytrium sp. | Extracted Biomass (Medium Lipid) (Hexane) | 0.1% | −11.4 |
| | | 0.01% | +4.1 |
| | | 0.001% | +19.6 |
| Aurantiochytrium sp. | Extracted Biomass (High Lipid) (Ethanol) | 0.1% | −25.3 |
| | | 0.01% | −16.9 |
| | | 0.001% | −5.8 |

Example 12

An experiment was performed to determine the effect of treating *Arabidopsis thaliana* with a variety of treatments made from microalgae under normal growth conditions and under temperature stressed conditions. The bioassay was initiated using four day old plantlets grown on half strength Murashige and Skoog (MS) medium, supplemented with 1% (w/v) sucrose and solidified with 0.7% (w/v) agar in square petri plates. Plates were vertically stacked in the growth chamber set at 22° C. with 16-h light/8-h dark cycle, with light intensity of 100 µmol/m$^{-2}$s$^{-1}$. Each plate contained five replicate plantlets. Plantlets were transferred onto medium supplemented with concentrations of 0.01% (0.01 mL/L) or 0.001% (0.001 mL/L) of non-oil treatments, or 0.001% (0.001 mL/L) or 0.0001% (0.0001 mL/L) of oil treatments listed in the table and compared to an untreated control. The treatments were prepared as described in Example 10.

After seven days, half of the plates were placed in a growth chamber and subjected to three days of continuous temperature stress (35° C.) while the other half were maintained at about 22° C. Following the temperature stress period, the plantlets were allowed to grow for seven additional days, and plant dry weight was measured at the end. The results are shown in Tables 6-7, which display the results for each tested concentration with respect to the untreated control.

TABLE 6

Growth (No temperature Stress)

| Genus | Treatment | Concentration | Dry Weight % Difference vs. Control |
|---|---|---|---|
| Galdieria | Whole Biomass | 0.01% | +3.5 |
| | | 0.001% | +15.9 |
| Galdieria | Extracted Biomass | 0.01% | −2.8 |
| | | 0.001% | −12.5 |
| Galdieria | Extracted Oil | 0.001% | −4.1 |
| | | 0.0001% | −6.3 |
| Galdieria | Low Protein Whole Biomass | 0.01% | −11.3 |
| | | 0.001% | −10.2 |

TABLE 6-continued

Growth (No temperature Stress)

| Genus | Treatment | Concentration | Dry Weight % Difference vs. Control |
|---|---|---|---|
| Galdieria | Low Protein Extracted Biomass | 0.01% 0.001% | +13.7 +43.6 |
| Galdieria | Low Protein Extracted Oil | 0.001% 0.0001% | −44.9 −51.4 |
| Galdieria | Protein Fraction | 0.01% 0.001% | +6.0 −2.2 |
| Chlorella sp. (acetate) | Whole Biomass | 0.01% 0.001% | +2.1 +11.8 |
| Chlorella sp. (acetate) | Extracted Biomass | 0.01% 0.001% | −8.1 −5.6 |
| Chlorella sp. (acetate) | Extracted oil | 0.001% 0.0001% | +3.9 −20.7 |
| Haematococcus | Whole Biomass | 0.01% 0.001% | −23.8 +10.8 |
| Haematococcus | Extracted Biomass | 0.01% 0.001% | +36.9 +19.2 |
| Haematococcus | Extracted Oil | 0.001% 0.0001% | −54.0 −18.2 |
| Isochrysis | Whole Biomass | 0.01% 0.001% | +1.0 −14.5 |
| Isochrysis | Extracted Biomass | 0.01% 0.001% | −5.9 −16.4 |
| Isochrysis | Extracted Oil | 0.001% 0.0001% | −21.3 +6.9 |
| Nannochloropsis | Whole Biomass | 0.01% 0.001% | −45.9 −39.0 |
| Nannochloropsis | Extracted Biomass | 0.01% 0.001% | −3.6 −37.8 |
| Nannochloropsis | Extracted Oil | 0.001% 0.0001% | +2.0 −8.8 |
| Porphyridium | Whole Biomass | 0.01% 0.001% | −6.0 −13.3 |
| Porphyridium | Extracted Biomass | 0.01% 0.001% | +16.5 +2.6 |
| Porphyridium | Extracted Oil | 0.001% 0.0001% | +29.6 −0.2 |
| Porphyridium | EPS | 0.01% 0.001% | −12.7 +28.8 |
| Schizochytrium | Whole Biomass | 0.01% 0.001% | −19.2 −24.8 |
| Schizochytrium | Extracted Biomass | 0.01% 0.001% | −3.4 −4.8 |
| Schizochytrium | Extracted Oil | 0.001% 0.0001% | −25.3 −61.4 |
| Tetraselmis | Whole Biomass | 0.01% 0.001% | — −3.1 |
| Tetraselmis | Extracted Biomass | 0.01% 0.001% | −32.6 −29.7 |
| Tetraselmis | Extracted Oil | 0.001% 0.0001% | −32.6 −12.2 |
| Pavlova | Whole Biomass | 0.01% 0.001% | +11.4 −1.3 |
| Pavlova | Extracted Biomass | 0.01% 0.001% | +12.4 +13.8 |
| Pavlova | Extracted Oil | 0.001% 0.0001% | −1.2 −1.1 |
| Phaeodactylum | Whole Biomass | 0.01% 0.001% | −1.0 −10.3 |
| Phaeodactylum | Extracted Biomass | 0.01% 0.001% | +23.7 −3.7 |
| Phaeodactylum | Extracted Oil | 0.001% 0.0001% | −4.2 −5.9 |
| Nannochloropsis | High Lipid Whole Biomass | 0.01% 0.001% | −21.2 −9.8 |
| Nannochloropsis | High Lipid Extracted Biomass | 0.01% 0.001% | −5.6 −5.3 |
| Nannochloropsis | High Lipid Extracted Oil | 0.001% 0.0001% | −7.1 −12.8 |
| Porphyridium | PE rich fraction | 0.01% 0.001% | +3.8 +1.4 |
| Porphyridium | PEB 1 lipid + EPS fraction | 0.01% 0.001% | +4.0 +4.4 |
| Porphyridium | Extracted Oil | 0.001% 0.0001% | +2.0 −5.8 |
| Porphyridium | LEB2 + EPS | 0.01% 0.001% | −8.9 −16.6 |
| Porphyridium | Biomass − EPS | 0.01% 0.001% | −15.4 −24.5 |
| Porphyridium | PE rich fraction from biomass − EPS | 0.01% 0.001% | +14.4 −17.8 |
| Porphyridium | PEB 2 Lipid + PS fraction | 0.01% 0.001% | −2.6 −12.9 |
| Aurantiochytrium sp. | Whole Biomass | 0.01% 0.001% | −15.8 −36.9 |
| Aurantiochytrium sp. | Extracted Biomass (hexane) | 0.01% 0.001% | +3.0 +3.3 |
| Aurantiochytrium sp. | Extracted Oil (hexane) | 0.001% 0.0001% | −24.3 +8.2 |
| Aurantiochytrium sp. | Extracted Biomass (ethanol) | 0.01% 0.001% | +17.1 +11.9 |
| Aurantiochytrium sp. | Extracted Oil (ethanol) | 0.001% 0.0001% | +5.3 +16.3 |
| Aurantiochytrium sp. | Extracted Oil (mechanical) | 0.001% 0.0001% | +5.3 +16.3 |
| Spirulina | Extracted Biomass (hexane) | 0.01% 0.001% | +5.3 +16.3 |
| Spirulina | Extracted Oil (hexane) | 0.001% 0.0001% | +21.8 +14.2 |
| Spirulina | Extracted Biomass (acetone) | 0.01% 0.001% | +5.3 +16.3 |
| Spirulina | Extracted Oil (acetone) | 0.001% 0.0001% | +21.1 +23.5 |
| Spirulina | Low Protein Whole Biomass | 0.01% 0.001% | −22.6 −8.1 |
| Spirulina | Protein Fraction | 0.01% 0.001% | +3.4 +1.7 |
| Spirulina | Lyzed Whole Biomass | 0.01% 0.001% | +5.0 +0.2 |
| Scenedesmus | Whole Biomass | 0.01% 0.001% | −27.6 −19.0 |
| Scenedesmus | Extracted Biomass | 0.01% 0.001% | +10.0 0.0 |
| Scenedesmus | Extracted Oil | 0.001% 0.0001% | −15.2 −2.1 |
| T-Isochrysis | Whole Biomass | 0.01% 0.001% | +27.4 +11.2 |
| T-Isochrysis | Extracted Biomass (ethanol) | 0.01% 0.001% | +21.7 +8.3 |
| T-Isochrysis | Extracted Oil (ethanol) | 0.001% 0.0001% | +6.4 +27.2 |
| Chlorella zofingiensis | Whole Biomass | 0.01% 0.001% | −9.1 +4.7 |
| Chlorella zofingiensis | Extracted Biomass (ethanol) | 0.01% 0.001% | +10.2 +11.4 |
| Chlorella zofingiensis | Extracted oil (ethanol) | 0.001% 0.0001% | +6.1 +2.5 |
| Chlorella sp. (glucose) | Whole Biomass | 0.01% 0.001% | −6.3 +13.6 |
| Chlorella sp. (glucose) | Extracted Biomass (ethanol) | 0.01% 0.001% | −13.0 −18.8 |
| Chlorella sp. (glucose) | Extracted oil (ethanol) | 0.001% 0.0001% | −7.6 −9.6 |
| Aurantiochytrium sp. | Whole Biomass (Medium Lipid) | 0.01% 0.001% | −21.1 −26.0 |

TABLE 6-continued

Growth (No temperature Stress)

| Genus | Treatment | Concentration | Dry Weight % Difference vs. Control |
|---|---|---|---|
| Aurantiochytrium sp. | Extracted Biomass (High Lipid) (Mechanical Extraction) | 0.01% 0.001% | −29.2 −21.7 |
| Aurantiochytrium sp. | Extracted Oil (High Lipid) (Hexane) | 0.001% 0.0001% | −11.7 +26.0 |
| Aurantiochytrium sp. | Extracted Oil (High Lipid) (Ethanol) | 0.001% 0.0001% | −7.0 −51.6 |
| Aurantiochytrium sp. | Extracted Oil (High Lipid) (Mechanical Extraction) | 0.001% 0.0001% 0.001% | −6.7 −13.2 −13.0 |
| Aurantiochytrium sp. | Extracted Oil (Medium Lipid) (Hexane) | 0.0001% | −14.4 |
| Aurantiochytrium sp. | Extracted Oil (Medium Lipid) (Hexane) | 0.001% 0.0001% | −0.5 −17.3 |
| Aurantiochytrium sp. | Extracted Biomass (Medium Lipid) (Hexane) | 0.01% 0.001% | −4.7 −2.1 |
| Aurantiochytrium sp. | Extracted Biomass (Medium Lipid) (Ethanol) | 0.01% 0.001% | −11.8 −0.1 |
| Aurantiochytrium sp. | Whole Biomass (High Lipid) | 0.01% 0.001% | −11.3 −7.2 |
| Aurantiochytrium sp. | Extracted Biomass (High Lipid) (Ethanol) | 0.01% 0.001% | −6.0 −8.4 |
| Aurantiochytrium sp. | Extracted Biomass (High Lipid) (Hexane) | 0.01% 0.001% | −17.0 −4.4 |
| Botryococcus | Lyzed Whole Biomass | 0.01% 0.001% | −14.0 −2.3 |
| Botryococcus | Extracted Oil | 0.001% 0.0001% | −14.4 −14.7 |
| Botryococcus | Extracted Biomass | 0.01% 0.001% | −23.3 −21.3 |

TABLE 7

Temperature Stress

| Genus | Treatment | Concentration | Dry Weight % Difference vs. Control |
|---|---|---|---|
| Galdieria | Whole Biomass | 0.01% 0.001% | −14.1 — |
| Galdieria | Extracted Biomass | 0.01% 0.001% | +1.1 — |
| Galdieria | Extracted Oil | 0.001% 0.0001% | −34.3 −29.7 |
| Galdieria | Low Protein Whole Biomass | 0.01% 0.001% | −15.7 +14.7 |
| Galdieria | Low Protein Extracted Biomass | 0.01% 0.001% | +8.9 +32.6 |
| Galdieria | Low Protein Extracted Oil | 0.001% 0.0001% | −44.4 −23.6 |
| Galdieria | Protein Fraction | 0.01% 0.001% | +6.2 −8.9 |
| Chlorella sp. (acetate) | Whole Biomass | 0.01% 0.001% | +42.0 +23.6 |
| Chlorella sp. (acetate) | Extracted Biomass | 0.01% 0.001% | −7.2 +4.8 |
| Chlorella sp. (acetate) | Extracted oil | 0.001% 0.0001% | −18.6 −9.7 |
| Haematococcus | Whole Biomass | 0.01% 0.001% | −38.0 −17.0 |
| Haematococcus | Extracted Biomass | 0.01% 0.001% | −0.7 +54.8 |
| Haematococcus | Extracted Oil | 0.001% 0.0001% | −46.0 +18.1 |
| Isochrysis | Whole Biomass | 0.01% 0.001% | — −5.1 |
| Isochrysis | Extracted Biomass | 0.01% 0.001% | −15.2 −38.4 |
| Isochrysis | Extracted Oil | 0.001% 0.0001% | −13.8 +3.1 |
| Nannochloropsis | Whole Biomass | 0.01% 0.001% | −40.6 −22.8 |
| Nannochloropsis | Extracted Biomass | 0.01% 0.001% | −29.0 −5.1 |
| Nannochloropsis | Extracted Oil | 0.001% 0.0001% | +28.3 +10.1 |
| Porphyridium | Whole Biomass | 0.01% 0.001% | +13.0 −9.4 |
| Porphyridium | Extracted Biomass | 0.01% 0.001% | +18.4 −2.4 |
| Porphyridium | Extracted Oil | 0.001% 0.0001% | +21.4 −15.0 |
| Porphyridium | EPS | 0.01% 0.001% | +8.7 +0.5 |
| Schizochytrium | Whole Biomass | 0.01% 0.001% | −51.4 +17.4 |
| Schizochytrium | Extracted Biomass | 0.01% 0.001% | −15.9 −17.0 |
| Schizochytrium | Extracted Oil | 0.001% 0.0001% | −56.5 −44.9 |
| Tetraselmis | Whole Biomass | 0.01% 0.001% | +6.8 0.0 |
| Tetraselmis | Extracted Biomass | 0.01% 0.001% | −42.4 −51.8 |
| Tetraselmis | Extracted Oil | 0.001% 0.0001% | −12.6 −5.8 |
| Pavlova | Whole Biomass | 0.01% 0.001% | +18.4 +28.8 |
| Pavlova | Extracted Biomass | 0.01% 0.001% | +40.8 +7.2 |
| Pavlova | Extracted Oil | 0.001% 0.0001% | +32.2 +19.8 |
| Phaeodactylum | Whole Biomass | 0.01% 0.001% | +31.0 +5.0 |
| Phaeodactylum | Extracted Biomass | 0.01% 0.001% | +8.3 +3.4 |
| Phaeodactylum | Extracted Oil | 0.001% 0.0001% | +11.4 +27.9 |
| Nannochloropsis | High Lipid Whole Biomass | 0.01% 0.001% | −21.7 −13.1 |
| Nannochloropsis | High Lipid Extracted Biomass | 0.01% 0.001% | +4.8 −18.3 |
| Nannochloropsis | High Lipid Extracted Oil | 0.001% 0.0001% | −14.3 −12.7 |
| Porphyridium | PE rich fraction | 0.01% 0.001% | −14.7 −7.8 |
| Porphyridium | PEB 1 lipid + EPS fraction | 0.01% 0.001% | +0.4 +20.7 |
| Porphyridium | Extracted Oil | 0.001% 0.0001% | −7.5 −13.4 |
| Porphyridium | LEB2 + EPS | 0.01% 0.001% | −43.4 +4.1 |
| Porphyridium | Biomass − EPS | 0.01% 0.001% | +1.7 −16.9 |
| Porphyridium | PE rich fraction from biomass − EPS | 0.01% 0.001% | −6.2 −10.0 |
| Porphyridium | PEB 2 Lipid + PS fraction | 0.01% 0.001% | −12.4 +2.7 |

TABLE 7-continued

Temperature Stress

| Genus | Treatment | Concentration | Dry Weight % Difference vs. Control |
|---|---|---|---|
| *Aurantiochytrium* sp. | Whole Biomass | 0.01% | −17.1 |
|  |  | 0.001% | −2.4 |
| *Aurantiochytrium* sp. | Extracted Biomass (hexane) | 0.01% | −22.0 |
|  |  | 0.001% | +5.2 |
| *Aurantiochytrium* sp. | Extracted Oil (hexane) | 0.001% | −15.5 |
|  |  | 0.0001% | −1.2 |
| *Aurantiochytrium* sp. | Extracted Biomass (ethanol) | 0.01% | +10.7 |
|  |  | 0.001% | +2.6 |
| *Aurantiochytrium* sp. | Extracted Oil (ethanol) | 0.001% | −13.5 |
|  |  | 0.0001% | −7.9 |
| *Aurantiochytrium* sp. | Extracted Oil (mechanical) | 0.001% | −11.3 |
|  |  | 0.0001% | +21.1 |
| *Spirulina* | Extracted Biomass (hexane) | 0.01% | −6.8 |
|  |  | 0.001% | +25.5 |
| *Spirulina* | Extracted Oil (hexane) | 0.001% | +28.3 |
|  |  | 0.0001% | +7.9 |
| *Spirulina* | Extracted Biomass (acetone) | 0.01% | +7.4 |
|  |  | 0.001% | +3.5 |
| *Spirulina* | Extracted Oil (acetone) | 0.001% | +13.5 |
|  |  | 0.0001% | +18.4 |
| *Spirulina* | Low Protein Whole Biomass | 0.01% | −39.4 |
|  |  | 0.001% | −16.9 |
| *Spirulina* | Protein Fraction | 0.01% | −27.7 |
|  |  | 0.001% | −26.9 |
| *Spirulina* | Lyzed Whole Biomass | 0.01% | −25.9 |
|  |  | 0.001% | −17.5 |
| *Scenedesmus* | Whole Biomass | 0.01% | −44.4 |
|  |  | 0.001% | −26.7 |
| *Scenedesmus* | Extracted Biomass | 0.01% | −35.4 |
|  |  | 0.001% | −25.9 |
| *Scenedesmus* | Extracted Oil | 0.001% | −35.1 |
|  |  | 0.0001% | −28.4 |
| *T-Isochrysis* | Whole Biomass | 0.01% | −11.4 |
|  |  | 0.001% | −12.8 |
| *T-Isochrysis* | Extracted Biomass (ethanol) | 0.01% | −15.3 |
|  |  | 0.001% | −4.0 |
| *T-Isochrysis* | Extracted Oil (ethanol) | 0.001% | −14.2 |
|  |  | 0.0001% | −4.2 |
| *Chlorella zofingiensis* | Whole Biomass | 0.01% | −38.0 |
|  |  | 0.001% | −11.7 |
| *Chlorella zofingiensis* | Extracted Biomass (ethanol) | 0.01% | +2.8 |
|  |  | 0.001% | −0.4 |
| *Chlorella zofingiensis* | Extracted oil (ethanol) | 0.001% | −13.3 |
|  |  | 0.0001% | −21.2 |
| *Chlorella* sp. (glucose) | Whole Biomass | 0.01% | −26.8 |
|  |  | 0.001% | −12.6 |
| *Chlorella* sp. (glucose) | Extracted Biomass (ethanol) | 0.01% | −15.1 |
|  |  | 0.001% | −18.7 |
| *Chlorella* sp. (glucose) | Extracted oil (ethanol) | 0.001% | +1.4 |
|  |  | 0.0001% | −25.1 |
| *Aurantiochytrium* sp. | Whole Biomass (Medium Lipid) | 0.01% | −73.8 |
|  |  | 0.001% | −40.4 |
| *Aurantiochytrium* sp. | Extracted Biomass (High Lipid) (Mechanical Extraction) | 0.01% | −11.0 |
|  |  | 0.001% | −2.3 |
| *Aurantiochytrium* sp. | Extracted Oil (High Lipid) (Hexane) | 0.001% | +9.6 |
|  |  | 0.0001% | +29.3 |
| *Aurantiochytrium* sp. | Extracted Oil (High Lipid) (Ethanol) | 0.001% | −0.9 |
|  |  | 0.0001% | −16.7 |
| *Aurantiochytrium* sp. | Extracted Oil (High Lipid) (Mechanical Extraction) | 0.001% | −17.6 |
|  |  | 0.0001% | −12.1 |
| *Aurantiochytrium* sp. | Extracted Oil (Medium Lipid) (Hexane) | 0.001% | −13.5 |
|  |  | 0.0001% | −16.9 |
| *Aurantiochytrium* sp. | Extracted Oil (Medium Lipid) (Hexane) | 0.001% | 1.2 |
|  |  | 0.0001% | −19.0 |
| *Aurantiochytrium* sp. | Extracted Biomass (Medium Lipid) (Hexane) | 0.01% | −3.7 |
|  |  | 0.001% | +16.6 |
| *Aurantiochytrium* sp. | Extracted Biomass (Medium Lipid) (Ethanol) | 0.01% | −0.5 |
|  |  | 0.001% | −9.6 |
| *Aurantiochytrium* sp. | Whole Biomass (High Lipid) | 0.01% | −28.6 |
|  |  | 0.001% | −5.1 |
| *Aurantiochytrium* sp. | Extracted Biomass (High Lipid) (Ethanol) | 0.01% | −14.0 |
|  |  | 0.001% | +7.5 |
| *Aurantiochytrium* sp. | Extracted Biomass (High Lipid) (Hexane) | 0.01% | −30.6 |
|  |  | 0.001% | −15.3 |
| *Botryococcus* | Lyzed Whole Biomass | 0.01% | −3.9 |
|  |  | 0.001% | +1.8 |
| *Botryococcus* | Extracted Oil | 0.001% | −10.1 |
|  |  | 0.0001% | +0.3 |
| *Botryococcus* | Extracted Biomass | 0.01% | −2.6 |
|  |  | 0.001% | +17.7 |

Example 13

The bioassay was initiated using cut mung bean seedlings which were grown in vials supplemented with concentrations of the same microalgae based treatments of 0.1% (0.1 mL/L), 0.01% (0.01 mL/L), or 0.001% (0.001 mL/L) non-oil treatments, or 0.01% (0.01 mL/L), 0.001% (0.001 mL/L), or 0.0001% (0.0001 mL/L) oil, and compared to an untreated control. The mung bean seedlings were initially grown on vermiculite for two weeks and then cut approximately 3 cm below the cotyledons. Cut seedlings were placed in glass scintillation vials to which 15 mL of water or treatments were added. The treatments were prepared as described in Example 10. Five seedlings were used for each treatment. The root growth parameters of distance of root growth from meristem, number of roots, and root length were measured after 7 days. The results are shown in Table 8, which display the results for each tested concentration with respect to the untreated control.

TABLE 8

| Genus | Treatment | Conc. | Distance of Root Growth from Meristem % Difference vs. Control | Number of Roots % Difference vs. Control | Root Length % Difference vs. Control |
|---|---|---|---|---|---|
| *Galdieria* | Whole Biomass | 0.1% | +18.9 | +45.3 | −57.3 |
| | | 0.01% | +54.1 | −15.6 | −32.0 |
| | | 0.001% | +2.7 | −4.7 | −43.3 |
| *Galdieria* | Extracted Biomass | 0.1% | +89.2 | +18.8 | −65.3 |
| | | 0.01% | +73.0 | +15.6 | −44.0 |
| | | 0.001% | +62.2 | +45.3 | −64.0 |
| *Galdieria* | Extracted Oil | 0.01% | −6.5 | −21.1 | +1.4 |
| | | 0.001% | −13.0 | −29.5 | +23.9 |
| | | 0.0001% | +6.5 | −31.6 | +54.9 |
| *Galdieria* | Low Protein Whole Biomass | 0.1% | +150.0 | +87.2 | −22.7 |
| | | 0.01% | +127.8 | +44.7 | +44.0 |
| | | 0.001% | −11.1 | −25.5 | −32.0 |
| *Galdieria* | Low Protein Extracted Biomass | 0.1% | 0.0 | +42.0 | +24.4 |
| | | 0.01% | −19.2 | +26.0 | −6.7 |
| | | 0.001% | −19.2 | +16.0 | +73.3 |
| *Galdieria* | Low Protein Extracted Oil | 0.01% | −41.3 | −53.7 | −8.5 |
| | | 0.001% | −17.4 | −28.4 | +105.6 |
| | | 0.0001% | 0.0 | −25.3 | +73.2 |
| *Galdieria* | Protein Fraction | 0.1% | +37.8 | −35.9 | −84.0 |
| | | 0.01% | −18.9 | 0.0 | −48.0 |
| | | 0.001% | +13.5 | +10.9 | −4.0 |
| *Chlorella* sp. (acetate) | Whole Biomass | 0.1% | +83.3 | 0.0 | −40.0 |
| | | 0.01% | +33.3 | +14.9 | −21.3 |
| | | 0.001% | +5.6 | −6.4 | +13.3 |
| *Chlorella* sp. (acetate) | Extracted Biomass | 0.1% | +72.2 | +23.4 | −5.3 |
| | | 0.01% | +100.0 | +6.4 | −44.0 |
| | | 0.001% | −27.8 | −17.0 | −42.7 |
| *Chlorella* sp. (acetate) | Extracted Oil | 0.01% | −26.1 | −29.5 | −47.9 |
| | | 0.001% | +50.0 | +34.7 | +4.2 |
| | | 0.0001% | −23.9 | −29.5 | +40.8 |
| *Haematococcus* | Whole Biomass | 0.1% | +218.9 | +162.5 | −53.3 |
| | | 0.01% | +29.7 | −63.4 | −50.7 |
| | | 0.001% | +2.7 | −1.6 | −24.0 |
| *Haematococcus* | Extracted Biomass | 0.1% | +7.7 | +32.0 | +35.6 |
| | | 0.01% | −15.4 | +26.0 | +15.6 |
| | | 0.001% | −23.1 | +22.0 | +88.9 |
| *Haematococcus* | Extracted Oil | 0.01% | −10.9 | −37.9 | +40.8 |
| | | 0.001% | −34.8 | −43.4 | +106.0 |
| | | 0.0001% | +19.6 | −24.2 | +53.5 |
| *Isochrysis* | Extracted Biomass | 0.1% | −46.2 | −44.0 | −87.8 |
| | | 0.01% | −26.9 | +16.0 | +53.3 |
| | | 0.001% | −3.8 | −2.0 | +8.9 |
| *Isochrysis* | Extracted Oil | 0.01% | +107.4 | +15.9 | +87.7 |
| | | 0.001% | +34.3 | −6.5 | +28.8 |
| | | 0.0001% | +63.0 | +36.4 | +30.8 |
| *Nannochloropsis* | Extracted Biomass | 0.1% | −30.8 | −8.0 | +35.6 |
| | | 0.01% | −19.2 | −8.0 | +13.3 |
| | | 0.001% | −46.2 | −67.0 | −20.0 |
| *Nannochloropsis* | Extracted Oil | 0.01% | +103.7 | −196 | +63.1 |
| | | 0.001% | +62.0 | −13.6 | +36.5 |
| | | 0.0001% | −7.4 | −2.8 | +10.8 |
| *Porphyridium* | Whole Biomass | 0.1% | −64.9 | −81.2 | −93.3 |
| | | 0.01% | −8.1 | −35.9 | −62.7 |
| | | 0.001% | −13.5 | −53.1 | −60.0 |
| *Porphyridium* | Extracted Biomass | 0.1% | +394.4 | +61.7 | +12.0 |
| | | 0.01% | +11.1 | 0.0 | −21.3 |
| | | 0.001% | +16.7 | 0.0 | −14.7 |
| *Porphyridium* | Extracted Oil | 0.01% | −10.9 | −25.3 | −43.7 |
| | | 0.001% | −63.0 | −63.2 | −26.8 |
| | | 0.0001% | −37.0 | −38.9 | −21.1 |
| *Porphyridium* | EPS | 0.1% | −61.1 | −74.5 | −88.0 |
| | | 0.01% | −50.0 | −42.6 | −49.3 |
| | | 0.001% | +5.6 | +10.6 | −28.0 |
| *Schizochytrium* | Whole Biomass | 0.1% | +218.9 | +128.1 | −84.0 |
| | | 0.01% | +173.0 | +84.4 | −60.0 |
| | | 0.001% | +100.0 | +21.9 | −48.0 |
| *Schizochytrium* | Extracted Biomass | 0.1% | +96.2 | +38.0 | −2.2 |
| | | 0.01% | −7.7 | +40.0 | +53.3 |
| | | 0.001% | 0.0 | +54.0 | +51.1 |
| *Schizochytrium* | Extracted Oil | 0.01% | +21.7 | −2.1 | +22.5 |
| | | 0.001% | −26.1 | −23.2 | −1.4 |
| | | 0.0001% | −10.9 | −27.4 | +62.0 |

TABLE 8-continued

| Genus | Treatment | Conc. | Distance of Root Growth from Meristem % Difference vs. Control | Number of Roots % Difference vs. Control | Root Length % Difference vs. Control |
|---|---|---|---|---|---|
| *Tetraselmis* | Whole Biomass | 0.1% | −5.6 | −38.3 | −50.7 |
| | | 0.01% | −5.6 | +29.8 | +1.3 |
| | | 0.001% | −16.7 | −12.8 | −13.3 |
| *Tetraselmis* | Extracted Biomass | 0.1% | −11.5 | +32.0 | +17.8 |
| | | 0.01% | −23.1 | −16.0 | +20.0 |
| | | 0.001% | −61.5 | −52.0 | −68.9 |
| *Tetraselmis* | Extracted Oil | 0.01% | +170.4 | −14.0 | +84.6 |
| | | 0.001% | +40.7 | −6.5 | +15.4 |
| | | 0.0001% | +66.7 | +14.0 | +49.2 |
| *Pavlova* | Whole Biomass | 0.1% | +202.9 | +229.1 | +13.8 |
| | | 0.01% | +57.1 | +105.5 | +96.3 |
| | | 0.001% | +60.7 | +81.8 | −40.0 |
| *Pavlova* | Extracted Biomass | 0.1% | +185.7 | +1655 | +43.8 |
| | | 0.01% | +28.6 | +74.5 | +95.0 |
| | | 0.001% | +2.9 | +41.8 | −11.2 |
| *Pavlova* | Extracted Oil | 0.01% | 0.0 | +28.9 | +6.9 |
| | | 0.001% | +13.3 | +46.7 | +18.1 |
| | | 0.0001% | −6.7 | +37.8 | +50.0 |
| *Phaeodactylum* | Whole Biomass | 0.1% | +171.4 | +167.3 | +83.8 |
| | | 0.01% | +82.1 | +115.9 | +46.9 |
| | | 0.001% | +60.0 | +45.5 | — |
| *Phaeodactylum* | Extracted Biomass | 0.1% | +100.0 | +85.5 | +82.5 |
| | | 0.01% | +96.4 | +168.2 | +60.9 |
| | | 0.001% | −2.9 | +27.3 | −6.2 |
| *Phaeodactylum* | Extracted Oil | 0.01% | +80.0 | +35.6 | +18.8 |
| | | 0.001% | +6.7 | +24.4 | +26.9 |
| | | 0.0001% | +26.7 | +26.7 | +26.3 |
| *Nannochloropsis* | High Lipid Whole Biomass | 0.1% | +13.3 | +60.0 | +15.6 |
| | | 0.01% | +33.3 | +44.4 | +18.8 |
| | | 0.001% | +6.7 | +62.2 | +25.0 |
| *Nannochloropsis* | High Lipid Extracted Biomass | 0.1% | +100.0 | +44.4 | +56.9 |
| | | 0.01% | 0.0 | −2.2 | +15.6 |
| | | 0.001% | +6.7 | +37.8 | +34.4 |
| *Nannochloropsis* | High Lipid Extracted Oil | 0.01% | +73.3 | −6.7 | −2.5 |
| | | 0.001% | +20.0 | +17.8 | +18.8 |
| | | 0.0001% | +13.3 | +26.7 | +5.6 |
| *Porphyridium* | PE rich fraction | 0.1% | +162.2 | +271.4 | −4.5 |
| | | 0.01% | 101.9 | 175.7 | −26.4 |
| | | 0.001% | +86.1 | +111.4 | −22.7 |
| *Porphyridium* | PEB 1 lipid + EPS fraction | 0.1% | +142.2 | +144.3 | −34.5 |
| | | 0.01% | +122.2 | +121.4 | −26.4 |
| | | 0.001% | +44.4 | +30.0 | −13.6 |
| *Porphyridium* | Extracted Oil | 0.01% | +93.3 | +117.1 | −42.7 |
| | | 0.001% | +25.0 | +91.1 | −43.2 |
| | | 0.0001% | +48.9 | +57.1 | −27.3 |
| *Porphyridium* | LEB2 + EPS | 0.1% | +118.5 | +154.3 | −35.5 |
| | | 0.01% | +91.7 | +112.5 | −46.6 |
| | | 0.001% | +16.7 | +7.1 | −6.8 |
| *Porphyridium* | Biomass − EPS | 0.1% | +146.7 | +194.3 | −21.6 |
| | | 0.01% | +68.9 | +75.7 | −27.7 |
| | | 0.001% | +60.0 | +61.4 | +13.6 |
| *Porphyridium* | PE rich fraction from Biomass − EPS | 0.1% | −4.4 | −25.7 | −89.8 |
| | | 0.01% | +108.9 | +234.3 | −65.9 |
| | | 0.001% | +22.2 | +24.3 | −17.0 |
| *Porphyridium* | PEB 2 Lipid + PS fraction | 0.1% | +168.9 | +240.0 | −43.2 |
| | | 0.01% | +133.3 | +221.4 | −28.4 |
| | | 0.001% | +44.4 | +54.3 | +6.8 |
| *Aurantiochytrium* sp. | Whole Biomass | 0.1% | +162.2 | +181.4 | +4.5 |
| | | 0.01% | +93.3 | +91.4 | −19.3 |
| | | 0.001% | +60.0 | −5.7 | +89.8 |
| *Aurantiochytrium* sp. | Extracted Biomass (hexane) | 0.1% | +155.6 | +210.0 | −3.4 |
| | | 0.01% | +124.4 | +82.9 | +5.7 |
| | | 0.001% | +42.2 | +30.0 | +26.1 |
| *Aurantiochytrium* sp. | Extracted Oil (hexane) | 0.01% | +60.0 | +72.9 | +19.3 |
| | | 0.001% | −17.8 | +20.0 | +51.1 |
| | | 0.0001% | +4.4 | +14.3 | +13.6 |
| *Aurantiochytrium* sp. | Extracted Biomass (ethanol) | 0.1% | +128.9 | +250.0 | −5.5 |
| | | 0.01% | +37.8 | +77.1 | −18.2 |
| | | 0.001% | +13.3 | +51.4 | 0.0 |
| *Aurantiochytrium* sp. | Extracted Oil (ethanol) | 0.01% | +37.8 | +51.4 | 0.0 |
| | | 0.001% | +37.0 | +2.9 | −29.1 |
| | | 0.0001% | +58.3 | +48.6 | −36.4 |

TABLE 8-continued

| Genus | Treatment | Conc. | Distance of Root Growth from Meristem % Difference vs. Control | Number of Roots % Difference vs. Control | Root Length % Difference vs. Control |
|---|---|---|---|---|---|
| Aurantiochytrium sp. | Extracted Oil (mechanical) | 0.01% | +62.2 | +95.7 | −31.8 |
| | | 0.001% | +36.1 | +42.9 | −21.6 |
| | | 0.0001% | +11.1 | +34.3 | −37.5 |
| Spirulina | Extracted Biomass (hexane) | 0.1% | +100.0 | +012.9 | −2.3 |
| | | 0.01% | +72.2 | +61.4 | −40.9 |
| | | 0.001% | +27.8 | +18.6 | −25.0 |
| Spirulina | Extracted Oil (hexane) | 0.01% | +102.8 | +85.7 | −14.8 |
| | | 0.001% | +44.4 | +60.0 | −1.1 |
| | | 0.0001% | +19.4 | +15.7 | −14.8 |
| Spirulina | Extracted Biomass (acetone) | 0.1% | +72.2 | +167.1 | +19.3 |
| | | 0.01% | +41.7 | +60.0 | −35.2 |
| | | 0.001% | −13.9 | +12.5 | −29.5 |
| Spirulina | Extracted Oil (acetone) | 0.01% | +58.3 | +60.0 | −53.4 |
| | | 0.001% | +11.1 | +50.0 | −12.5 |
| | | 0.0001% | −47.2 | −15.7 | +6.8 |
| Spirulina | Low Protein Whole Biomass | 0.1% | +205.6 | +385.7 | −71.6 |
| | | 0.01% | +94.4 | +152.9 | −50.0 |
| | | 0.001% | +22.2 | +52.9 | +4.5 |
| Spirulina | Protein Fraction | 0.1% | +155.6 | −12.5 | +146.4 |
| | | 0.01% | +88.9 | −20.5 | +77.1 |
| | | 0.001% | +41.7 | +25 | +60.0 |
| Spirulina | Lyzed Whole Biomass | 0.1% | +122.2 | −12.5 | +134.3 |
| | | 0.01% | +22.2 | +50.0 | +34.3 |
| | | 0.001% | +2.8 | +10.2 | +5.7 |
| Scenedesmus | Whole Biomass | 0.1% | +112.4 | +14.5 | +111.3 |
| | | 0.01% | +62.8 | +8.3 | +66.2 |
| | | 0.001% | +51.7 | −26.2 | +6.7 |
| Scenedesmus | Extracted Biomass | 0.1% | +35.2 | −10.2 | +32.3 |
| | | 0.01% | +104.1 | +42.8 | +39.5 |
| | | 0.001% | +79.3 | +26.8 | +33.3 |
| Scenedesmus | Extracted Oil | 0.01% | +98.6 | +23.1 | +109.2 |
| | | 0.001% | +109.7 | +12.0 | +51.8 |
| | | 0.0001% | +96.6 | +23.1 | +43.6 |
| T-Isochrysis | Whole Biomass | 0.1% | +106.9 | +87.7 | +189.7 |
| | | 0.01% | −31.0 | +34.2 | +19.0 |
| | | 0.001% | +34.5 | −27.7 | +25.6 |
| T-Isochrysis | Extracted Biomass (ethanol) | 0.1% | +34.5 | +144.6 | +105.1 |
| | | 0.01% | −36.6 | +158.5 | +43.6 |
| | | 0.001% | +13.1 | +50.2 | +27.2 |
| T-Isochrysis | Extracted Oil (ethanol) | 0.01% | +68.3 | +99.4 | +72.3 |
| | | 0.001% | +65.5 | +39.1 | +66.2 |
| | | 0.0001% | +93.1 | +2.2 | +31.3 |
| Chlorella zofingiensis | Whole Biomass | 0.1% | +369.0 | +12.0 | +158.5 |
| | | 0.01% | +37.9 | +21.8 | +60.0 |
| | | 0.001% | −37.9 | +4.6 | +5.1 |
| Chlorella zofingiensis | Extracted Biomass (ethanol) | 0.1% | +73.8 | −8.9 | +96.9 |
| | | 0.01% | +37.9 | +23.1 | +31.3 |
| | | 0.001% | −22.8 | +25.5 | +25.1 |
| Chlorella zofingiensis | Extracted Oil (ethanol) | 0.01% | +32.4 | −17.5 | +66.2 |
| | | 0.001% | +3.4 | −16.9 | +5.1 |
| | | 0.0001% | +17.2 | +4.6 | +66.7 |
| Chlorella sp. (glucose) | Whole Biomass | 0.1% | +195.2 | −37.8 | +273.3 |
| | | 0.01% | +51.7 | +10.8 | +76.9 |
| | | 0.001% | −13.8 | −18.5 | +12.8 |
| Chlorella sp. (glucose) | Extracted Biomass (ethanol) | 0.1% | +86.2 | −20.0 | +107.7 |
| | | 0.01% | −3.4 | +47.7 | +27.2 |
| | | 0.001% | −25.5 | −12.6 | −11.8 |
| Chlorella sp. (glucose) | Extracted Oil (ethanol) | 0.01% | +15.9 | −12.6 | +74.4 |
| | | 0.001% | −13.8 | +41.5 | +41.0 |
| | | 0.0001% | +13.8 | −27.7 | +25.6 |
| Aurantiochytrium sp. | Whole Biomass (Medium Lipid) | 0.1% | +173.3 | −7.4 | +102.0 |
| | | 0.01% | +6.7 | −27.0 | +8.0 |
| | | 0.001% | +37.5 | −26.3 | +17.5 |
| Aurantiochytrium sp. | Extracted Biomass (High Lipid) (Mechanical Extraction) | 0.1% | +266.7 | +12.3 | +207.5 |
| | | 0.01% | +70.8 | +26.3 | 0.0 |
| | | 0.001% | +90.0 | +51.6 | +42.0 |
| Aurantiochytrium sp. | Extracted Oil (High Lipid) (Hexane) | 0.01% | +91.7 | +32.6 | +50.0 |
| | | 0.001% | +91.7 | +38.6 | +32.5 |
| | | 0.0001% | +41.7 | +52.6 | +20.0 |
| Aurantiochytrium sp. | Extracted Oil (High Lipid) (Ethanol) | 0.01% | +143.3 | +26.3 | +68.0 |
| | | 0.001% | +112.5 | +94.7 | +55.0 |
| | | 0.0001% | +50.0 | −19.3 | +65.0 |

TABLE 8-continued

| Genus | Treatment | Conc. | Distance of Root Growth from Meristem % Difference vs. Control | Number of Roots % Difference vs. Control | Root Length % Difference vs. Control |
|---|---|---|---|---|---|
| Aurantiochytrium sp. | Extracted Oil (High Lipid) (Mechanical Extraction) | 0.01% 0.001% 0.0001% | +20.0 +40.0 +25.0 | +53.0 +50.2 +33.3 | +24.0 +16.0 +10.0 |
| Aurantiochytrium sp. | Extracted Oil (Medium Lipid) (Hexane) | 0.01% 0.001% 0.0001% | +285.7 −4.7 +114.3 | −5.4 −0.9 −27.0 | +94.3 +21.9 +57.1 |
| Aurantiochytrium sp. | Extracted Oil (Medium Lipid) (Ethanol) | 0.01% 0.001% 0.0001% | +185.7 +71.4 +174.3 | −4.1 −10.8 +3.8 | +102.9 +57.1 +50.9 |
| Aurantiochytrium sp. | Extracted Biomass (Medium Lipid) (Hexane) | 0.1% 0.01% 0.001% | +374.3 +265.7 +48.6 | −67.6 −12.4 −8.1 | +185.7 +110.3 +34.9 |
| Aurantiochytrium sp. | Extracted Biomass (Medium Lipid) (Ethanol) | 0.1% 0.01% 0.001% | +381.3 +45.0 +120.0 | −47.0 −32.1 −9.1 | +191.7 +24.4 +62.2 |
| Aurantiochytrium sp. | Whole Biomass (High Lipid) | 0.1% 0.01% 0.001% | +433.3 +230.0 −15.0 | −71.7 −56.4 −4.2 | +129.6 +654.4 +2.2 |
| Aurantiochytrium sp. | Extracted Biomass (High Lipid) (Ethanol) | 0.1% 0.01% 0.001% | +210.0 +100.0 +100.0 | −91.5 −40.6 +49.1 | +46.7 +33.3 +57.8 |
| Aurantiochytrium sp. | Extracted Biomass (High Lipid) (Hexane) | 0.1% 0.01% 0.001% | +290.0 +95.0 +110.0 | −73.3 −62.4 −52.7 | +164.4 +75.6 +66.7 |
| Botryococcus | Lyzed Whole Biomass | 0.1% 0.01% 0.001% | +520.0 +66.7 0.0 | −56.4 +9.1 −56.4 | +417.8 +25.9 +417.8 |
| Botryococcus | Extracted Oil | 0.01% 0.001% 0.0001% | +170.0 −20.0 +5.0 | −34.5 +20.0 −40.6 | +115.6 +28.9 +26.7 |
| Botryococcus | Extracted Biomass | 0.1% 0.01% 0.001% | +435.0 +115.0 +30.0 | −33.3 −28.5 +5.5 | +304.4 +95.6 +40.0 |

Example 14

An experiment was performed to determine the effect of treating *Arabidopsis thaliana* with a variety of microalgae treatments under conditions where the plants are exposed to *Sclerotinia sclerotiorum*. The bioassay was initiated using four week old plantlets grown on Jiffy pellets (peat moss pellets). Plants on Jiffy pellets were placed on trays and the foliar was sprayed with concentrations of 0.1% (0.1 mL/L) or 0.01% (0.01 mL/L) of non-oil treatments, or 0.01% (0.01 mL/L) or 0.001% (0.001 mL/L) of microalgae oil, and compared to an untreated control. The treatments were prepared as described in Example 10. The day after the application of the treatments, the plugs of *Sclerotinia sclerotiorum* were placed on two leaves per plant. The disease severity (diameter of infected area around a plug) was recorded after 3 days. The results are shown in Table 9, which display the results for each tested concentration with respect to the untreated control.

TABLE 9

| Genus | Treatment | Concentration | Diameter of disease infected area % Difference vs. Control |
|---|---|---|---|
| Galdieria | Low Protein Extracted Biomass | 0.1% 0.01% | −34.4 +44.2 |
| Galdieria | Low Protein Extracted Oil | 0.01% 0.001% | −1.8 +31.8 |
| Galdieria | Protein Fraction | 0.1% 0.01% | −29.5 +0.4 |
| Chlorella sp. (acetate) | Whole Biomass | 0.1% 0.01% | +66.8 +2.8 |
| Haematococcus | Extracted Biomass | 0.1% 0.01% | −3.6 +62.6 |
| Isochrysis | Extracted Biomass | 0.1% 0.01% | +57.5 +28.0 |
| Nannochloropsis | Extracted Biomass | 0.1% 0.01% | +3.5 −15.4 |
| Schizochytrium | Extracted Biomass | 0.1% 0.01% | −24.7 +8.2 |
| Schizochytrium | Extracted Oil | 0.01% 0.001% | +43.6 +66.7 |

Example 15

An experiment was performed to determine the effect of *Chlorella* and *Aurantiochytrium* treatments on bell pepper plants when applied to the root zone during salt (NaCl) stress conditions. The treatments consisted of whole pasteurized Chlorella and Aurantiochytrium cells in addition to the normal regiment of plant nutrients. The treatments were applied to plants both receiving and not receiving salt stress at rates of 0.2 mL per plant per week or 2 mL per plant per week, and compared to a control that only received the normal regiment of plant nutrients. The plants that were under salt stress conditions received 60 mM of NaCl starting on day 2 of the experiment and 120 mM of NaCl on day 6 of the experiment in the normal plant nutrient solution. Each treatment was performed on 24 replicates. The plants were monitored and the height, circumference, leaf surface area, bud count, shoot fresh weight, shoot dry weight, root and dry weight were measured. The experiment was run for 21 days and the results are shown in the Tables 10-11 below.

TABLE 10

| | | | % Difference from Control | | | |
|---|---|---|---|---|---|---|
| Treatment | Salt Stress | Rate | Diameter (cm) | Circ. (cm) | Height (cm) | Bud Count |
| Aurantiochytrium sp. | Y | 2 mL | +1.4 | −2.8 | +3.1 | −13.5 |
| | N | 2 mL | −0.9 | −0.9 | +3.2 | −4.6 |
| Aurantiochytrium sp. | Y | 0.2 mL | +5.3 | −1.8 | +1.2 | +7.4 |
| | N | 0.2 mL | −3.6 | −3.6 | +0.3 | −2.9 |
| Chlorella sp. (acetate) | Y | 2 mL | +8.5 | +8.5 | +6.8 | +13.3 |
| | N | 2 mL | −2.5 | −2.5 | +3.2 | +3.5 |
| Chlorella sp. (acetate) | Y | 0.2 mL | +12.3 | +12.3 | +7.6 | +1.7 |
| | N | 0.2 mL | −0.9 | −0.9 | +1.6 | −2.9 |

TABLE 11

| | | | % Difference from Control | | | |
|---|---|---|---|---|---|---|
| Treatment | Salt Stress | Rate | Shoot Fresh Weight (g) | Leaf Surface Area (sq. cm) | Shoot Dry Weight (g) | Root Dry Weight (g) |
| Aurantiochytrium sp. | Y | 2 mL | +2.0 | +5.0 | −3.4 | −3.5 |
| | N | 2 mL | −7.8 | −4.8 | −5.1 | −15.6 |
| Aurantiochytrium sp. | Y | 0.2 mL | +7.7 | +13.0 | +7.2 | −60.7 |
| | N | 0.2 mL | −8.4 | −1.7 | −7.7 | −13.6 |
| Chlorella sp. (acetate) | Y | 2 mL | +18.9 | +20.3 | +21.8 | +15.8 |
| | N | 2 mL | −4.6 | −7.3 | −0.4 | −2.8 |
| Chlorella sp. (acetate) | Y | 0.2 mL | +15.1 | +21.5 | +14.3 | +11.2 |
| | N | 0.2 mL | −2.6 | −3.2 | −3.7 | −8.0 |

Example 16

An experiment was performed to effect of Chlorella and Aurantiochytrium treatments on snap pea plant growth and yield. The Chlorella treatment comprised of mixotrophically cultured cells from a non-axenic culture, which were then pasteurized and pH stabilized as whole cells without being subjected to a drying process. The Aurantiochytrium treatments comprised of multiple different pasteurized and pH stabilized preparations consisting of: a) whole cells from non-axenic cultures, b) disrupted cells that had been subjected to an oil extracted process, c) whole cells from axenic cultures, d) whole cells that were subjected to boiling, and e) whole cells from non-axenic cultures that were subjected to a washing process. The experiment was performed in fields located in Minnesota, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including pod fresh weight, pod count per plant, shoot fresh weight, root fresh weight, total pod yield, total yield, marketable yield, and utilization. The results for each treatment were averaged and compared to the untreated control, and are shown in Tables 12-13

TABLE 12

| | | | % Difference from Control | | | | |
|---|---|---|---|---|---|---|---|
| Genus | Treatment | App. Rate (L/ acre) | Pod Fresh Weight (g) | Pod count/ plant | Shoot Fresh Weight (g) | Root Fresh Weight (g) | Total pod yield (lb/ plot) |
| Chlorella sp. (acetate) | Whole Biomass | 3.7 | −0.4 | +1.3 | +3.5 | +2.7 | +2.0 |
| | | 7.5 | −2.3 | +3.5 | +2.6 | +7.1 | +4.5 |
| | | 15 | −0.8 | +5.7 | +8.0 | +5.4 | +4.0 |
| Aurantiochytrium sp. | Whole Biomass Non-axenic | 3.7 | −2.1 | +4.4 | +7.9 | +11.6 | +2.6 |
| | | 7.5 | −3.3 | +7.0 | +8.2 | +15.2 | +3.4 |
| | | 15 | −1.6 | +5.9 | +9.1 | +17.0 | +4.1 |
| Aurantiochytrium sp. | Extracted Biomass | 3.7 | −4.7 | +5.5 | +8.9 | +21.4 | +3.9 |
| | | 7.5 | −1.2 | +5.7 | +8.5 | +17.9 | +4.9 |
| | | 15 | −1.0 | +4.0 | +8.1 | +27.7 | +4.7 |
| Aurantiochytrium sp. | Whole Biomass Axenic | 3.7 | −3.3 | +9.0 | +8.5 | +23.2 | +3.6 |
| | | 7.5 | +0.4 | +5.7 | +8.3 | +8.9 | +4.4 |
| | | 15 | −5.3 | +4.4 | +8.0 | +27.7 | +3.5 |
| Aurantiochytrium sp. | Whole Biomass Boiled | 3.7 | −2.1 | +6.8 | +7.6 | +19.6 | +1.0 |
| | | 7.5 | +1.4 | +7.3 | +10.2 | +30.4 | +2.2 |
| | | 15 | +0.4 | +4.0 | +10.3 | +17.0 | +4.8 |
| Aurantiochytrium sp. | Whole Biomass Washed | 3.7 | −0.2 | +5.7 | +9.4 | +19.6 | +1.0 |
| | | 7.5 | +1.6 | +5.7 | +9.6 | +24.1 | +3.2 |
| | | 15 | −0.4 | +4.6 | +10.0 | +20.5 | +4.8 |

TABLE 13

| | | | % Difference from Control | | | |
|---|---|---|---|---|---|---|
| Genus | Treatment | App. Rate (L/ acre) | Total Yield (lb/ acre) | Marketable yield (lb pod/plot) | Marketable yield (lb/ acre) | % Utilization |
| Chlorella sp. (acetate) | Whole Biomass | 3.7 | +2.0 | +0.7 | +0.7 | −1.3 |
| | | 7.5 | +4.5 | +6.0 | +6.0 | +1.5 |
| | | 15 | +4.0 | +5.5 | +5.5 | +1.4 |
| Aurantiochytrium sp. | Whole Biomass Non-axenic | 3.7 | +2.6 | +4.6 | +4.6 | +2.3 |
| | | 7.5 | +3.4 | +6.2 | +6.2 | +2.7 |
| | | 15 | +4.1 | +7.1 | +7.1 | +2.8 |
| Aurantiochytrium sp. | Extracted Biomass | 3.7 | +3.9 | +6.2 | +6.2 | +2.3 |
| | | 7.5 | +4.9 | +6.5 | +6.5 | +1.6 |
| | | 15 | +4.7 | +6.7 | +6.7 | +2.0 |
| Aurantiochytrium sp. | Whole Biomass Axenic | 3.7 | +3.6 | +5.7 | +5.7 | +2.1 |
| | | 7.5 | +4.4 | +6.2 | +6.2 | +1.5 |
| | | 15 | +3.5 | +5.5 | +5.5 | +2.0 |
| Aurantiochytrium sp. | Whole Biomass Boiled | 3.7 | +1.0 | +2.6 | +2.6 | +1.8 |
| | | 7.5 | +2.2 | +3.6 | +3.6 | +1.4 |
| | | 15 | +4.8 | +6.9 | +6.9 | +1.3 |
| Aurantiochytrium sp. | Whole Biomass Washed | 3.7 | +1.0 | +2.1 | +2.1 | +1.1 |
| | | 7.5 | +3.2 | +4.7 | +4.7 | +1.5 |
| | | 15 | +4.8 | +7.2 | +7.2 | +2.3 |

Example 17

An experiment was performed to effect of *Chlorella* and *Aurantiochytrium* treatments on snap bean plant growth and yield. The *Chlorella* treatment comprised of mixotrophically cultured cells from a non-axenic culture, which were then pasteurized and pH stabilized as whole cells without being subjected to a drying process. The *Aurantiochytrium* treatments comprised of multiple different pasteurized and pH stabilized preparations consisting of: a) whole cells from non-axenic cultures, b) disrupted cells that had been subjected to an oil extracted process, c) whole cells from axenic cultures, d) whole cells that were subjected to boiling, and e) whole cells from non-axenic cultures that were subjected to a washing process. The experiment was performed in fields located in Minnesota, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including pod fresh weight, pod count per plant, shoot fresh weight, root fresh weight, total pod yield, total yield, marketable yield, and utilization. The results for each treatment were averaged and compared to the untreated control, and are shown in Tables 14-15.

TABLE 14

| | | | % Difference from Control | | | | |
| --- | --- | --- | --- | --- | --- | --- | --- |
| Genus | Treatment | App. Rate (L/acre) | Pod Fresh Weight (g) | Pod count/plant | Shoot Fresh Weight (g) | Root Fresh Weight (g) | Total pod yield (lb/plot) |
| *Chlorella* sp. (acetate) | Whole Biomass | 3.7 7.5 15 | +0.6 +6.6 +2.8 | +7.2 +3.1 +5.2 | +2.5 +3.6 +2.6 | +0.9 +1.3 +1.5 | +6.7 +2.6 +2.8 |
| *Aurantiochytrium* sp. | Whole Biomass Non-axenic | 3.7 7.5 15 | +2.8 +5.5 +2.0 | +4.1 +7.7 +2.6 | +2.6 +3.2 +1.8 | -0.6 +2.8 +4.5 | +6.4 +6.4 +6.0 |
| *Aurantiochytrium* sp. | Extracted Biomass | 3.7 7.5 15 | +5.2 +4.5 +6.0 | +2.6 +4.6 +3.1 | +3.2 +2.5 +3.2 | +1.5 +3.1 +4.8 | +4.9 +4.4 +6.5 |
| *Aurantiochytrium* sp. | Whole Biomass Axenic | 3.7 7.5 15 | +3.2 +7.5 +5.3 | +5.2 +4.1 +7.2 | +3.0 +4.2 +3.8 | +2.5 +4.5 +4.1 | +4.5 +5.9 +8.5 |
| *Aurantiochytrium* sp. | Whole Biomass Boiled | 3.7 7.5 15 | +3.6 +4.7 +6.9 | +1.5 +5.2 +2.1 | +4.0 +4.2 +3.9 | +1.9 +6.2 +5.5 | +4.7 +6.4 +6.9 |
| *Aurantiochytrium* sp. | Whole Biomass Washed | 3.7 7.5 15 | +4.9 +4.2 +6.6 | +1.0 +5.7 +4.6 | +3.8 +4.1 +4.7 | +2.9 +3.5 +6.3 | +5.5 +9.2 +7.5 |

TABLE 15

| | | | % Difference from Control | | |
| --- | --- | --- | --- | --- | --- |
| Genus | Treatment | App. Rate (L/acre) | Total Yield (lb/acre) | Marketable yield (lb pod/plot) | Marketable yield (lb/acre) | % Utilization |

| Genus | Treatment | App. Rate (L/acre) | Total Yield (lb/acre) | Marketable yield (lb pod/plot) | Marketable yield (lb/acre) | % Utilization |
| --- | --- | --- | --- | --- | --- | --- |
| *Chlorella* sp. (acetate) | Whole Biomass | 3.7 7.5 15 | +6.7 +2.6 +2.8 | +6.9 +2.8 +3.3 | +6.9 +2.8 +3.3 | +0.1 +0.2 +0.4 |
| *Aurantiochytrium* sp. | Whole Biomass Non-axenic | 3.7 7.5 15 | +6.4 +6.4 +6.0 | +5.3 +5.5 +5.7 | +5.3 +5.5 +5.7 | -1.1 -0.8 -0.3 |
| *Aurantiochytrium* sp. | Extracted Biomass | 3.7 7.5 15 | +4.9 +4.4 +6.5 | +4.7 +4.3 +7.0 | +4.7 +4.3 +7.0 | -0.2 -0.1 +0.5 |
| *Aurantiochytrium* sp. | Whole Biomass Axenic | 3.7 7.5 15 | +4.5 +5.9 +8.5 | +4.0 +6.2 +7.7 | +4.0 +6.2 +7.7 | -0.5 +0.3 -0.7 |
| *Aurantiochytrium* sp. | Whole Biomass Boiled | 3.7 7.5 15 | +4.7 +6.4 +6.9 | +4.6 +6.3 +6.9 | +4.6 +6.3 +6.9 | -0.1 0.0 0.0 |
| *Aurantiochytrium* sp. | Whole Biomass Washed | 3.7 7.5 15 | +5.5 +9.2 +7.5 | +5.8 +8.9 +7.1 | +5.8 +8.9 +7.1 | +0.2 -0.3 -0.4 |

Example 18

An experiment was performed to effect of microalgae treatments on strawberry plant growth and yield. The *Chlorella* treatment comprised of mixotrophically cultured cells from a non-axenic culture, which were then pasteurized and pH stabilized as whole cells without being subjected to a drying process. The *Aurantiochytrium* treatments comprised multiple different pasteurized and pH stabilized preparations consisting of: a) whole cells from non-axenic cultures, and b) disrupted cells that had been subjected to an oil extracted process. The *Spirulina* treatment comprised of cells from a non-axenic culture, which were then pasteurized and pH stabilized as whole cells without being subjected to a drying process. The *Isochrysis* treatment comprised of cells from a non-axenic culture, which were then pasteurized and pH stabilized as whole cells without being subjected to a drying process. The *Scenedesmus* treatment comprised of cells from a non-axenic polyculture primarily comprised of "demsus" microalgae with the most likely candidate being

*Scenedesmus*, which were then pasteurized and pH stabilized as whole cells without being subjected to a drying process. The experiment was performed in fields located in California, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including Brix, shoot weight, total fruit number, large red fruit number, large red fruit weight, marketable yield, and marketable fruit. The results for each treatment were averaged and compared to the untreated control, and are shown in Tables 16-17.

TABLE 16

| | | | % Difference from Control | | | |
|---|---|---|---|---|---|---|
| Genus | Treatment | App. Rate (L/acre) | % Brix | Shoot Weight (g) | Total Fruit (no.) | Large Red (no.) |
| *Chlorella* sp. (acetate) | Whole Biomass | 3.7 | −6.9 | +1.6 | +10.7 | +21.0 |
| | | 7.5 | −6.2 | +17.7 | −4.7 | +3.6 |
| | | 15 | −2.1 | +43.3 | −3.3 | +13.0 |

TABLE 16-continued

| | | | % Difference from Control | | | |
|---|---|---|---|---|---|---|
| Genus | Treatment | App. Rate (L/acre) | % Brix | Shoot Weight (g) | Total Fruit (no.) | Large Red (no.) |
| *Aurantiochytrium* sp. | Whole Biomass Non-axenic | 3.7 | −4.6 | +41.2 | +10.2 | −2.2 |
| | | 7.5 | +0.9 | +15.1 | +9.3 | +11.6 |
| | | 15 | −6.2 | +13.4 | +15.1 | +31.2 |
| *Aurantiochytrium* sp. | Extracted Biomass | 3.7 | −2.3 | +17.5 | +8.8 | 0.0 |
| | | 7.5 | −4.6 | +2.9 | −8.2 | +1.4 |
| | | 15 | −4.7 | +3.9 | −17.0 | −15.2 |
| *Spirulina* | Whole Biomass | 3.7 | −4.4 | −10.1 | −0.3 | −10.9 |
| | | 7.5 | −1.7 | +29.4 | +20.1 | +18.1 |
| | | 15 | −5.1 | −15.7 | +21.2 | +16.5 |
| *Isochrysis* | Whole Biomass | 3.7 | +0.4 | −30.1 | +20.6 | +31.9 |
| | | 7.5 | −3.2 | −35.7 | +4.7 | −6.5 |
| | | 15 | −2.4 | +1.0 | +0.5 | +26.8 |
| *Scenedesmus* | Whole Biomass | 3.7 | +4.9 | −20.7 | +19.0 | +63.8 |
| | | 7.5 | −7.7 | +1.8 | +4.9 | +22.5 |
| | | 15 | −3.7 | +10.7 | +11.0 | +27.5 |

TABLE 17

| | | | % Difference from Control | | |
|---|---|---|---|---|---|
| Genus | Treatment | App. Rate (L/acre) | Large Red Weight (g) | Marketable yield (lb/acre) | % Marketable Fruit (by no.) | % Marketable Fruit (by wt.) |
| *Chlorella* sp. (acetate) | Whole Biomass | 3.7 | +16.1 | +16.1 | +8.5 | +5.7 |
| | | 7.5 | −6.9 | −6.9 | +11.3 | +6.3 |
| | | 15 | +15.8 | +15.8 | +11.9 | +7.8 |
| *Aurantiochytrium* sp. | Whole Biomass Non-axenic | 3.7 | +9.0 | +9.0 | −1.6 | +2.2 |
| | | 7.5 | +10.9 | +10.9 | +2.8 | +2.5 |
| | | 15 | +35.5 | +35.5 | +8.4 | +6.4 |
| *Aurantiochytrium* sp. | Extracted Biomass | 3.7 | +1.6 | +1.6 | +4.9 | +5.1 |
| | | 7.5 | +6.0 | +6.0 | +24.1 | +11.9 |
| | | 15 | −6.3 | −6.3 | +9.7 | +2.2 |
| *Spirulina* | Whole Biomass | 3.7 | −2.1 | −2.1 | −1.7 | −1.1 |
| | | 7.5 | +7.6 | +7.6 | +3.5 | −0.2 |
| | | 15 | +15.3 | +15.3 | +2.4 | +5.3 |
| *Isochrysis* | Whole Biomass | 3.7 | +27.7 | +27.7 | +9.4 | +6.8 |
| | | 7.5 | −9.9 | −9.9 | −2.7 | −2.1 |
| | | 15 | +24.8 | +24.8 | +21.7 | +11.3 |
| *Scenedesmus* | Whole Biomass | 3.7 | +44.5 | +44.5 | +18.9 | +10.2 |
| | | 7.5 | +22.3 | +22.3 | +9.7 | +7.4 |
| | | 15 | +36.6 | +36.6 | +12.5 | +9.0 |

Example 19

An experiment was performed to effect of *T-Isochrysis* treatments on tomato plant growth and yield. The *T-Isochrysis* treatment comprised of cells from a non-axenic culture, which were then pasteurized and pH stabilized as whole cells without being subjected to a drying process. The experiment was performed in fields located in California, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including plant height, total fruit, and marketable fruit. The results for each treatment were averaged and compared to the untreated control, and are shown in Tables 18-19.

TABLE 18

| | | | % Difference from Control | | | |
|---|---|---|---|---|---|---|
| Organism | Treatment | App. Rate (L/acre) | Plant Height (30 day) | Plant Height (60 day) | Total Fruit count per acre | Total Fruit weight (lb/acre) |
| T-Isochrysis | Whole Biomass | 3.7 | +17.5 | +16.0 | +20.6 | +21.3 |
| | | 7.5 | -2.7 | +8.7 | -15.5 | +3.9 |
| | | 15 | -0.2 | +2.0 | -30.2 | -16.2 |

TABLE 19

| | | | % Difference from Control | | | |
|---|---|---|---|---|---|---|
| Organism | Treatment | App. Rate (L/acre) | Marketable Fruit (lb/acre) | Utilization (by wt) | Large Red Fruit per plot (kg) | Large Green Fruit per plot (kg) |
| T-Isochrysis | Whole Biomass | 3.7 | +26.6 | +6.0 | +20.2 | +70.2 |
| | | 7.5 | -3.1 | -5.6 | +14.3 | +45.9 |
| | | 15 | -18.8 | -4.8 | -19.6 | -11.2 |

Example 20

An experiment was performed to effect of *T-Isochrysis* treatments on tomato plant growth and yield. The *T-Isochrysis* treatment comprised of cells from a non-axenic culture, which were then pasteurized and pH stabilized as whole cells without being subjected to a drying process. The experiment was performed in fields located in New York, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including plant height, total fruit, and marketable fruit. The results for each treatment were averaged and compared to the untreated control, and are shown in Tables 20-22.

TABLE 20

| | | | % Difference from Control | | | |
|---|---|---|---|---|---|---|
| Organism | Treatment | App. Rate (L/acre) | Avg. shoot wt. (g) | Root wt. per 3 plants (g) | Avg. Fruit wt. per plant (g) | Average Fruit wt. (g) |
| T-Isochrysis | Whole Biomass | 3.7 | +65.1 | +46.8 | +245.4 | +72.3 |
| | | 7.5 | +53.5 | +32.9 | +159.1 | +35.3 |
| | | 15 | +3.3 | 0.0 | +149.5 | +30.4 |

TABLE 21

| | | | % Difference from Control | | | |
|---|---|---|---|---|---|---|
| Organism | Treatment | App. Rate (L/acre) | Marketable Yield (lb/acre) $1^{st}$ Harvest | Marketable Yield (lb/acre) $2^{nd}$ Harvest | Total Yield (lb/acre) $1^{st}$ Harvest | Total Yield (lb/acre) $2^{nd}$ Harvest |
| T-Isochrysis | Whole Biomass | 3.7 | +253.1 | +23.1 | +204.5 | +37.7 |
| | | 7.5 | +110.8 | +105.14 | +83.1 | +85.8 |
| | | 15 | +45.0 | +6.7 | +25.7 | +19.7 |

TABLE 22

| | | | % Difference from Control | |
|---|---|---|---|---|
| Organism | Treatment | App. Rate (L/acre) | Utilization $1^{st}$ Harvest | Utilization $2^{nd}$ Harvest |
| T-*Isochrysis* | Whole Biomass | 3.7 | +29.8 | -9.6 |
| | | 7.5 | +8.0 | -66.4 |
| | | 15 | +26.0 | -44.3 |

Example 21

For the experiments described in some of the following examples, flask cultures were used to generate the biomass for the small scale testing (*Arabidopsis* plate, seed germination), and cultures were grown in closed bag bioreactors (90-440 L) to generate larger amounts of biomass needed for the hydroponics platform testing. Throughout the specification and the following examples: the term "photo" means phototrophic conditions; the term "mixo" means mixotrophic conditions; and the term "hetero" means heterotrophic conditions. The use of the terms "acetate" or "glucose" used in combination with the terms "mixo" or "hetero" indicate the source of organic carbon supplied to the microalgae in the specified growth conditions of the microalgae culture. The same species of microalgae were grown in the flask and bag bioreactor cultures for use in treatments described in the following examples.

For the flask cultures, *Nannochloropsis* was found to tolerate glucose. *Galdieria* was found to have considerable growth on glycerol under mixotrophic and heterotrophic conditions. *Chlorella/Micractinium* (HS26) was found to grow under all conditions (Mixo Glucose, Mixo Acetate, Hetero Glucose. Photo, Hetero Acetate).

For the bag bioreactor cultures, the following yields were obtained:

*Haematococcus* pluvialis (HS36)
  Photo
    Volume—440 L (produced from two 220 L cultures)
    Not axenic (i.e., some bacteria contamination)
    Harvest density—0.75 and 0.80 g/L
  Mixo Acetate
    Volume—360 L
    Axenic
    Harvest density—1.93 and 2.22 g/L
    Residual organic carbon—500 mg/L

*Chlamydomonas reinhardtii* (HS206)
  Photo
    Volume—440 L (produced from two 220 L cultures)
    Not axenic
    Harvest density—N/A
  Mixo Acetate
    Volume—220 L
    Not axenic
    Harvest density—2.43 g/L
    Residual organic carbon—470 mg/L

*Galdieria sulphuraria* (HS130)
  Photo
    Cultures died—no biomass for use in experiments
  Mixo Glucose
    Volume—90L
    Axenic
    Harvest density—5.033 g/L
    Residual organic carbon—1000 mg/L
  Hetero Glucose
    Volume—90L, 100L
    Axenic
    Harvest density—5.24, 4.88 g/L
    Residual organic carbon—100 mg/L

*Chlorella* sp./*Micractinium* (HS26)
  Photo
    Volume—220 L
    Axenic
    Harvest density—0.82, 0.78 g/L
  Mixo Acetate
    Volume—360 L
    Axenic
    Harvest density—23.9 g/L
    Residual organic carbon—not measured
  Mixo Glucose
    Volume—360 L
    Axenic
    Harvest density—3.46 g/L
    Residual organic carbon—1,000 mg/L
  Hetero Acetate
    Volume—360 L
    Axenic
    Harvest density—1.26 g/L
    Residual organic carbon—920 mg/L
  Hetero Glucose
    Volume—360 L
    Axenic
    Harvest density—2.74 g/L
    Residual organic carbon—250 mg/L

*Scenedesmus obliquus* (HS199)
  Photo
    Volume—220 L
    Axenic
    Harvest density—0.52, 0.39 g/L
  Mixo Acetate
    Volume—220 L
    Axenic
    Harvest density—2.3 g/L
    Residual organic carbon—1700 mg/L
  Mixo Glucose
    Volume—220 L
    Axenic
    Harvest density—2.78 g/L
    Residual organic carbon—50 mg/L
  Hetero Glucose
    Volume—220 L
    Axenic
    Harvest density—2.66 g/L
    Residual organic carbon—not measured Example 22 (RDT1818)

Experiments were done to test the effects of different microalgae compositions on wild type *Arabidopsis thaliana*. Wild type *Arabidopsis thaliana* seeds were surface sterilized by soaking in 70% ethanol for two minutes, followed by 2.5% bleach for 15 minutes and rinsing with sterile deionized (DI) water three times (15 plants per treatment). Seeds were vernalized by soaking in filtered reverse osmosis (RO) water at 4° C. then sown on 0.1× MS media for germination and placed on a lighting rack. Week old seedlings were transferred to experimental plates and inoculated with the described treatments.

The conditions of the experiments were as follows:
Temperature—25° C.
Day length—16 hr light/8 hr dark lighting cycle
Light irradiance—120-140 umol/m$^2$/s.

The following treatments were tested (18 mL/gal, biomass from flask cultures):
1. *Chlorella* Hetero Acetic
2. *Chlorella* Hetero Glucose
3. *Chlorella* Mixo Acetic
4. *Chlorella* Mixo Glucose
5. *Chlorella* Photo
6. *Galdieria* Hetero Glycerol
7. *Galdieria* Mixo Glycerol
8. *Galdieria* Photo
9. Control—NTC
10. Control—Mock The NTC control consisted of plants growing on an agar plate made up of a type of media called Murashige and Skoog basal salts. It was also buffered with MES buffer at pH 6.1 This media was the base media on top of which all the treatments were added. In other words, all of the plants "received" MS media. The microalgae biomass for the treatments was obtained from axenic flask cultures as described in Example 21.

The Mock control comprised the same nutrient formulation of nutrients found in the average PhycoTerra Production Batch (i.e., *Chlorella* [H526] Mixo Acetate) (also used in the Seed Germination studies), specifically:
  1.5% of *Chlorella* (HS26) lipids
  8.5% of protein and carbohydrates
  128 ppb of Abscisic acid (ABA)
  3.3 ppb of trans-ABA
  2.8 ppb of trans-zeatin-O-glucoside (ZOG)
  8.6 ppb of trans-zeatin (Z)
  16.4 ppb of cis-Z 1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

Leaf and root surface area ($cm^2$) were analyzed using imageJ. Root hair was also scored on a scale of 0-3 based on the following criteria: 0=no visible root hairs, 1=occasional visible root hairs in isolated areas, 2=obvious root hairs on some roots, 3=extensive root hairs across most roots.

Results from experiments are provided in Table 23.

TABLE 23

| | % Difference from Control – NTC | | |
|---|---|---|---|
| Treatment | Leaf SA | Root SA | Root Hair |
| *Chlorella* Photo | +5.2 | +43.7 | +5.6 |
| *Chlorella* Hetero Acetic | +12.9 | +57.2 | +111.1 |
| *Chlorella* Hetero Glucose | +10.8 | +46.0 | −5.6 |
| *Chlorella* Mixo Acetic | +9.5 | +14.2 | −16.7 |
| *Chlorella* Mixo Glucose | +37.7 | +75.3 | −33.3 |
| *Galdieria* Hetero | +9.1 | +26.1 | −28.9 |
| *Galdieria* Mixo | −1.7 | +32.7 | +4.7 |
| *Galdieria* Photo | +0.5 | +18.1 | −33.3 |
| Mock | −3.4 | +13.1 | −11.1 |

Example 23 (1818 repeat)

The experiments described in Example 22 was repeated with the following treatments (18 mL/gal, biomass from flask cultures):

1. *Chlorella* Hetero Acetic
2. *Chlorella* Hetero Glucose
3. *Chlorella* Mixo Acetic
4. *Chlorella* Mixo Glucose
5. *Chlorella* Photo
6. *Galdieria* Hetero Glycerol
7. *Galdieria* Mixo Glycerol
8. *Galdieria* Photo
9. *Nannochloropsis* Mixo Glucose
10. *Nannochloropsis* Photo
11. *Spirulina* Mixo Glucose
12. *Spirulina* Photo
13. Control—NTC
14. Control—Mock Combined results from experiments of Example 22 and 23 are provided in Table 24.

TABLE 24

| | % Difference from Control – NTC | | |
|---|---|---|---|
| Treatment | Leaf SA | Root SA | Root Hair |
| *Chlorella* Photo | +14.9 | +41.3 | −21.7 |
| *Chlorella* Hetero Acetic | +8.2 | +78.4 | +242.7 |
| *Chlorella* Hetero Glucose | +31.1 | +49.5 | +80.3 |
| *Chlorella* Mixo Acetic | +0.3 | +42.5 | 0.0 |
| *Chlorella* Mixo Glucose | +20.9 | +33.6 | −6.7 |
| *Galdieria* Hetero | −16.4 | −4.8 | −51.0 |
| *Galdieria* Mixo | −9.6 | +14.4 | −11.9 |
| *Galdieria* Photo | +30.1 | +62.5 | +72.7 |
| Mock | +12.7 | +36.0 | −2.1 |
| *Nannochloropsis* Mixo | +15.6 | +48.4 | +36.4 |
| *Nannochloropsis* Photo | +0.3 | +13.8 | −25.8 |
| *Spirulina* Mixo | +39.5 | +57.5 | +63.6 |
| *Spirulina* Photo | +9.5 | +34.3 | +37.1 |

TABLE 25

| Experiment | Treatment | Leaf area ($cm^2$) | Root area ($cm^2$) |
|---|---|---|---|
| Initial | NTC | 0.424 | 0.031 |
| | Mock | 0.410 | 0.035 |
| | *Chlorella* Hetero Acetic | 0.479 | 0.049 |
| | *Chlorella* Hetero Glucose | 0.470 | 0.045 |
| | *Chlorella* Mixo Acetic | 0.464 | 0.035 |
| | *Chlorella* Mixo Glucose | 0.584 | 0.054 |
| | *Chlorella* Photo | 0.446 | 0.045 |
| | *Galdieria* Hetero | 0.463 | 0.039 |
| | *Galdieria* Mixo | 0.423 | 0.042 |
| | *Galdieria* Photo | 0.426 | 0.037 |
| Repeat | NTC | 0.257 | 0.023 |
| | Mock | 0.295 | 0.032 |
| | *Chlorella* Hetero Acetic | 0.277 | 0.043 |
| | *Chlorella* Hetero Glucose | 0.319 | 0.033 |
| | *Chlorella* Mixo Acetic | 0.255 | 0.033 |
| | *Chlorella* Mixo Glucose | 0.305 | 0.031 |
| | *Chlorella* Photo | 0.293 | 0.033 |
| | *Galdieria* Hetero | 0.192 | 0.020 |
| | *Galdieria* Mixo | 0.227 | 0.026 |
| | *Galdieria* Photo | 0.334 | 0.038 |
| | *Nannochloropsis* Mixo | 0.294 | 0.034 |
| | *Nannochloropsis* Photo | 0.253 | 0.026 |
| | *Spirulina* Mixo | 0.343 | 0.035 |
| | *Spirulina* Photo | 0.276 | 0.032 |

Example 24 (1913)

The experiments described in Example 40 was repeated with the following treatments (18 mL/gal, biomass from flask cultures):

1. *Chlorella* Photo
2. *Chlorella* Mixo Acetate
3. *Chlorella* Mixo Glucose
4. *Chlorella* Hetero Acetate
5. *Chlorella* Hetero Glucose
6. Control—NTC
7. Control—Mock Acetate
8. Control—Mock Glucose The Mock Acetate and Mock Glucose consisted of the normal Mock solution that had been supplemented with either 2 g/L sodium acetate (Acetate) or 2 g/L glucose (Glucose), respectively.

Results from experiments are provided in Table 26.

TABLE 26

| Treatment | % Difference from Control – NTC Root Hair |
|---|---|
| *Chlorella* Hetero Acetic | +151.3 |
| *Chlorella* Hetero Glucose | −15.2 |
| *Chlorella* Mixo Acetic | +16.7 |
| *Chlorella* Mixo Glucose | +32.2 |
| *Chlorella* Photo | +8.3 |
| Mock Acetic | +16.7 |
| Mock Glucose | +16.7 |

Example 25 (1914)

The experiments described in Example 22 was repeated with the following treatments (18 mL/gal, biomass from flask cultures):

1. *Galdieria* Hetero Glycerol
2. *Galdieria* Mixo Glycerol
3. *Galdieria* Photo
4. *Nannochloropsis* Mixo Glucose
5. *Nannochloropsis* Photo 6. *Spirulina* Mixo Glucose
7. *Spirulina* Photo
8. Control—NTC
9. Control—Mock Combined results from experiments of Examples 24 and 25 are provided in Table 27. Combined results from experiments of Examples 22-25 are provided in Table 28.

TABLE 27

| Treatment | Mean Root Hair Score |
|---|---|
| NTC | 0.9231 |
| Mock | 1.3636 |
| Mock Acetic | 1.0000 |
| Mock Glucose | 1.0000 |
| *Chlorella* Hetero Acetic | 2.1538 |
| *Chlorella* Hetero Glucose | 0.7273 |
| *Chlorella* Mixo Acetic | 1.0000 |
| *Chlorella* Mixo Glucose | 1.1333 |
| *Chlorella* Photo | 0.9286 |
| *Galdieria* Hetero | 1.4167 |
| *Galdieria* Mixo | 1.2222 |
| *Galdieria* Photo | 1.7000 |
| *Nannochloropsis* Mixo | 1.3333 |
| *Nannochloropsis* Photo | 0.7500 |
| *Spirulina* Mixo | 0.6154 |
| *Spirulina* Photo | 1.0000 |

TABLE 28

| | % Difference from Control - NTC | | |
|---|---|---|---|
| Treatment | Leaf SA | Root SA | Root Hair |
| *Galdieria* Hetero | −38.8 | −33.6 | +41.7 |
| *Galdieria* Mixo | −22.2 | −42.4 | +22.2 |
| *Galdieria* Photo | −48.8 | −57.4 | +70.0 |
| Mock | +17.1 | −15.6 | +36.4 |
| *Nannochloropsis* Mixo | +1.6 | −38.5 | +33.3 |
| *Nannochloropsis* Photo | +9.8 | −32.9 | −25.0 |
| *Spirulina* Mixo | −20.4 | −33.0 | −38.5 |
| *Spirulina* Photo | −26.7 | −22.9 | +6.7 |

Example 26 (ADT 0049)

Experiments were done to test effects of microalgae compositions on corn, bean, and pepper seed germination in soil. Seeds were planted in Sunshine Mix #4 soil in trays, and germinated in a greenhouse. Fortex Pole Beans, Hydro Peppers, and RD4AG Corn plant species were tested. Nine deep 50 cell plug trays were packed with Sunshine Mix #4. All trays were dibbled and then soaked in water until soil was visibly wet, but seed hole was still exposed. Trays were left over night to soak up water, and the next day the seeds were planted at a 2 inch depth. Solutions of treatments were made so that when 4 mL of treatment solution were applied to a single plug cell the plant received 0.02 mL of treatment. Treatment solutions were applied directly to seedosphere before the hole was covered. There was a 4 mL Carrier Volume/200 mL solution: 0.02 mL treatment/plant=1 mL treatment and 199 mL reverse osmosis water (RO). Applications of treatments were applied in a random layout. Plug trays were left in greenhouse to germinate and watered every 24 hours. Plug trays were observed multiple times daily for germination:
  Corn—17 observations over a total of 141.5 hours
  Beans—27 observations over a total of 233 hours
  Peppers—37 observations over a total of 327.5 hours.

The following treatments were tested (0.02 mL/plant in a 4 mL carrier volume [0.25 gallon/acre in furrow], all microalgae biomass for treatments was produced in axenic flask cultures as described in Example 21):

1. *Chlorella* Hetero Acetic
2. *Chlorella* Hetero Glucose
3. *Chlorella* Mixo Acetic
4. *Chlorella* Mixo Glucose
5. *Chlorella* Photo
6. *Galdieria* Hetero Glycerol
7. *Galdieria* Mixo Glycerol
8. *Galdieria* Photo
9. Control—Reverse Osmosis (RO) water
10. Control—Mock (Mock is nutrient formulation of nutrients found in the average PhycoTerra Production Batch (i.e., *Chlorella* [H526] Mixo Acetate)

MOCK:

1.5% of *Chlorella* (HS26) lipids 8.5% of protein and carbohydrates 128 ppb of Abscisic acid (ABA)

3.3 ppb of trans-ABA 2.8 ppb of trans-zeatin-O-glucoside (ZOG)

8.6 ppb of trans-zeatin (Z)

16.4 ppb of cis-Z 1.6 ppb of trans-zeatin riboside (ZR)

42.5 ppb of cis-ZR 9.8 ppb of isopentenyladenine (iP)

4.1 ppb of isopentenyladenine riboside (iPR)

86.3 ppb of indole acetic acid (IAA)

Results are provided in Tables 29-31.

TABLE 29

| Corn | % Difference from Control (RO) regarding % Germination at Designated Time | | | | | | |
|---|---|---|---|---|---|---|---|
| Treatment | 88.5 h | 92.5 h | 95.5 h | 111.5 h | 115.5 h | 120 h | 136 h |
| Mock Control | −60.6 | +13.2 | −8.0 | −7..0 | −7..0 | −7..0 | −7..0 |
| *Galdieria* Photo | −18.2 | 0.0 | 0.0 | −7.0 | −7.0 | −7.0 | −7.0 |
| *Galdieria* Mixo Glycerol | −60.6 | +50.9 | 0.0 | 0.0 | 0.0 | 0.0 | 0.0 |
| *Galdieria* Hetero Glycerol | +21.2 | +37.7 | 0.0 | 0.0 | 0.0 | 0.0 | 0.0 |
| *Chlorella* Photo | +42.4 | 0.0 | −23.0 | −7.0 | −7.0 | −7.0 | 0.0 |
| *Chlorella* Mixo Glucose | 0.0 | +26.4 | 0.0 | −7.0 | −7.0 | −7.0 | 0.0 |
| *Chlorella* Mixo Acetate | 0.0 | +50.9 | −8.0 | 0.0 | 0.0 | 0.0 | 0.0 |
| *Chlorella* Hetero Glucose | +60.6 | +64.2 | 0.0 | 0.0 | 0.0 | 0.0 | 0.0 |
| *Chlorella* Hetero Acetic | −39.4 | +13.2 | −16.1 | 0.0 | 0.0 | 0.0 | 0.0 |

TABLE 30

| Bean Treatment | % Difference from Control (RO) regarding % Germination at Designated Time | | | | | | |
|---|---|---|---|---|---|---|---|
| | 88.5 h | 92.5 h | 95.5 h | 111.5 h | 115.5 h | 120 h | 136 h |
| Mock Control | −65.0 | −65.0 | −51.9 | −21.7 | −21.7 | −17.8 | −17.8 |
| Galdieria Photo | −65.0 | +35.0 | +22.2 | +11.7 | +21.7 | +9.6 | +9.6 |
| Galdieria Mixo Glycerol | 0.0 | +35.0 | 0.0 | −33.3 | −21.7 | 0.0 | +9.6 |
| Galdieria Hetero Glycerol | −100 | −35.0 | −25.9 | −21.7 | −11.7 | −17.8 | −8.2 |
| Chlorella Photo | −100 | −65.0 | −25.9 | −11.3 | −11.7 | −17.8 | −8.2 |
| Chlorella Mixo Glucose | +65.0 | +100 | +96.3 | +21.7 | +21.7 | +19.2 | +19.2 |
| Chlorella Mixo Acetate | −65.0 | −35.0 | −25.9 | −11.7 | −11.7 | −17.8 | −8.2 |
| Chlorella Hetero Glucose | −100 | −65.0 | +48.1 | 0.0 | 0.0 | 0.0 | +9.6 |
| Chlorella Hetero Acetate | −65.0 | −65.0 | −51.9 | 0.0 | 0.0 | −8.2 | +9.6 |

| Bean Treatment | % Difference from Control (RO) regarding % Germination at Designated Time | | | | | | |
|---|---|---|---|---|---|---|---|
| | 141.5 h | 145.5 h | 160.5 h | 165.5 h | 170 h | 185.5 h | 189 h |
| Mock Control | 0.0 | 0.0 | 0.0 | +9.6 | +9.6 | +9.6 | +19.2 |
| Galdieria Photo | +9.6 | +9.6 | +19.2 | +27.4 | +27.4 | +27.4 | +27.4 |
| Galdieria Mixo Glycerol | +9.6 | +9.6 | +9.6 | +19.2 | +19.2 | +19.2 | +19.2 |
| Galdieria Hetero Glycerol | −8.2 | −8.2 | 0.0 | 0.0 | 0.0 | 0. | 0.0 |
| Chlorella Photo | 0.0 | 0.0 | 0.0 | 0.0 | 0.0 | +9.6 | +9.6 |
| Chlorella Mixo Glucose | +19.2 | +19.2 | +19.2 | +19.2 | +19.2 | +19.2 | +19.2 |
| Chlorella Mixo Acetate | −8.2 | −8.2 | −8.2 | −8.2 | −8.2 | −8.2 | −8.2 |
| Chlorella Hetero Glucose | +9.6 | +9.6 | +9.6 | +9.6 | +19.2 | +19.2 | +19.2 |
| Chlorella Hetero Acetate | +9.6 | +9.6 | +9.6 | +9.6 | +9.6 | +9.6 | +9.6 |

| Bean Treatment | % Difference from Control (RO) regarding % Germination at Designated Time | | |
|---|---|---|---|
| | 192 h | 209.5 h | 216.5 h |
| Mock Control | 19.2 | +19.2 | +8.8 |
| Galdieria Photo | +27.4 | +27.4 | +16.3 |
| Galdieria Mixo Glycerol | +19.2 | +19.2 | +8.8 |
| Galdieria Hetero Glycerol | 0.0 | 0.0 | −8.7 |
| Chlorella Photo | +9.6 | +9.6 | 0.0 |
| Chlorella Mixo Glucose | +19.2 | +27.4 | +16.3 |
| Chlorella Mixo Acetate | −8.2 | −8.2 | −16.2 |
| Chlorella Hetero Glucose | +19.2 | +19.2 | +8.8 |
| Chlorella Hetero Acetate | +9.6 | +9.6 | 0.0 |

TABLE 31

| Pepper Treatment | % Difference from Control (RO) regarding % Germination at Designated Time | | | | | | |
|---|---|---|---|---|---|---|---|
| | 240.5 h | 257 h | 261.5 h | 264 h | 279.5 h | 289 h | 305 h |
| Mock Control | +42.6 | +9.6 | 0.0 | 0.0 | 0.0 | 0.0 | 0.0 |
| Galdieria Photo | −14.9 | −8.2 | +14.9 | +14.9 | +7.5 | +7.5 | +7.5 |
| Galdieria Mixo Glycerol | −42.6 | −45.2 | −23.0 | −8.0 | −1.0 | −14.0 | −14.0 |
| Galdieria Hetero Glycerol | −14.9 | −8.2 | +6.9 | +6.9 | +7.5 | +7.5 | +7.5 |
| Chlorella Photo | +12.8 | −17.8 | −23.0 | −23.0 | −6.5 | −6.5 | −6.5 |
| Chlorella Mixo Glucose | +42.6 | 0.0 | −8.0 | −8.0 | 0.0 | 0.0 | 0.0 |
| Chlorella Mixo Acetate | 0.0 | +27.4 | +6.9 | +6.9 | +7.5 | +7.5 | +7.5 |
| Chlorella Hetero Glucose | +12.8 | +9.6 | +6.9 | +14.9 | +7.5 | +7.5 | +7.5 |
| Chlorella Hetero Acetate | +42.6 | +19.2 | +6.9 | +6.9 | 0.0 | 0.0 | 0.0 |

| Pepper Treatment | % Difference from Control (RO) regarding % Germination at Designated Time | | |
|---|---|---|---|
| | 308 h | 313 h | 3273 h |
| Mock Control | 0.0 | 0.0 | −7.0 |
| Galdieria Photo | 7.5 | 7.5 | 0.0 |
| Galdieria Mixo Glycerol | −14.0 | −14.0 | −13.0 |
| Galdieria Hetero Glycerol | +7.5 | +7.5 | 0.0 |
| Chlorella Photo | −6.5 | −6.5 | −13.0 |
| Chlorella Mixo Glucose | 0.0 | 0.0 | −7.0 |
| Chlorella Mixo Acetate | +7.5 | +7.5 | 0.0 |
| Chlorella Hetero Glucose | +7.5 | +7.5 | 0.0 |
| Chlorella Hetero Acetate | 0.0 | 0.0 | −7.0 |

Example 27 (ADT 0055)

Experiments were done to test effects of microalgae compositions on corn, bean, and pepper seed germination in soil. Seeds were planted in Sunshine Mix #4 soil in trays, and germinated in a greenhouse. Fortex Pole Bean, Hydro Peppers, and RD4AG Corn plant species were tested. Nine deep 50 cell plug trays were packed with Sunshine mix #4. All trays were dibbled and then soaked in water until soil was visibly wet, but seed hole was still exposed. Trays were left over night to soak up water, and the next day the seeds were planted at a 2 inch depth. Solutions of treatments were made so that when 4 mL of solution were applied to a single plug cell the plant received 0.04 mL of treatment. Treatment solutions were applied directly to seedosphere before hole was covered. There was a 4 mL Carrier Volume/200 mL solution: 0.04 mL treatment/plant=2 mL treatment and 198 mL reverse osmosis water (RO). Applications were applied in a random layout. Plug trays were left in greenhouse to germinate and watered every 24 hours. Plug trays were observed multiple times daily for germination:

Corn—14 observations over 117 hours
Beans—24 observations over 216.5 hours
Peppers—33 observations over 305 hours The following treatments were tested (0.04 mL/plant in a 4 mL carrier volume [0.50 gallon/acre in furrow], all microalgae biomass for treatments was produced in axenic flask cultures as described in Example 21):

1. *Chlorella* Hetero Acetic
2. *Chlorella* Hetero Glucose
3. *Chlorella* Mixo Acetic
4. *Chlorella* Mixo Glucose
5. *Chlorella* Photo
6. *Galdieria* Hetero Glycerol
7. *Galdieria* Mixo Glycerol
8. *Galdieria* Photo
9. Control—Reverse Osmosis (RO) water
10. Control—Mock ((Mock is nutrient formulation of nutrients found in the average PhycoTerra Production Batch (i.e., *Chlorella* [HS26] Mixo Acetate)

MOCK:
1.5% of *Chlorella* (HS26) lipids
8.5% of protein and carbohydrates
128 ppb of Abscisic acid (ABA)
3.3 ppb of trans-ABA
2.8 ppb of trans-zeatin-O-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

Results are provided in Tables 32-34.

TABLE 32

| Corn Treatment | % Difference from Control (RO) regarding % Germination at Designated Time | | | | | |
|---|---|---|---|---|---|---|
| | 71 h | 88 h | 94.5 h | 97.5 h | 110.5 h | 113.5 h |
| Mock Control | −10.4 | −6.5 | −6.5 | −6.5 | −6.5 | −6.5 |
| Galdieria Photo | 0.0 | 0.0 | 0.0 | 0.0 | 0.0 | 0.0 |
| Galdieria Mixo Glycerol | −20.9 | 0.0 | 0.0 | 0.0 | 0.0 | +7.5 |
| Galdieria Hetero Glycerol | −50.7 | 0.0 | +7.5 | +7.5 | +7.5 | +7.5 |
| Chlorella Photo | −10.4 | 0.0 | +7.5 | +7.5 | +7.5 | +7.5 |
| Chlorella Mixo Glucose | −20.9 | 0.0 | 0.0 | 0.0 | 0.0 | 0.0 |
| Chlorella Mixo Acetate | −40.3 | −14.0 | −6.5 | −6.5 | −6.5 | −6.5 |
| Chlorella Hetero Glucose | −40.3 | −14.0 | 0.0 | 0.0 | 0.0 | 0.0 |
| Chlorella Hetero Acetate | −10.4 | +7.5 | +7.5 | +7.5 | +7.5 | +7.5 |

TABLE 33

| Bean Treatment | % Difference from Control (RO) regarding % Germination at Designated Time | | | | | | |
|---|---|---|---|---|---|---|---|
| | 71 h | 88 h | 94.5 h | 97.5 h | 110.5 h | 113.5 h | 117 h |
| Mock Control | −35.0 | −11.7 | +9.0 | +9.0 | 0.0 | 0.0 | −8.7 |
| Galdieria Photo | +100 | −11.7 | +19.4 | +19.4 | +19.2 | +19.2 | +8.8 |
| Galdieria Mixo Glycerol | −65.0 | −33.3 | 0.0 | 0.0 | −8.2 | −8.2 | +8.7 |
| Galdieria Hetero Glycerol | −35.0 | −11.7 | +9.0 | +9.0 | +9.6 | +19.2 | +8.8 |
| Chlorella Photo | 0.0 | +11.7 | +9.0 | +9.0 | 0.0 | 0.0 | 0.0 |
| Chlorella Mixo Glucose | 0.0 | +21.7 | +19.4 | +19.4 | +9.6 | +9.6 | 0.0 |
| Chlorella Mixo Acetate | +100.0 | +11.7 | +9.0 | +9.0 | 0.0 | 0.0 | −8.7 |

TABLE 33-continued

| | | | | | | | |
|---|---|---|---|---|---|---|---|
| *Chlorella* Hetero Glucose | +100.0 | +11.7 | +19.4 | +19.4 | +19.2 | +19.2 | +8.8 |
| *Chlorella* Hetero Acetate | +35.0 | −21.7 | 0.0 | 0.0 | 0.0 | 0.0 | −8.7 |

| Bean | % Difference from Control (RO) regarding % Germination at Designated Time | | | | |
|---|---|---|---|---|---|
| Treatment | 121 h | 136.5 h | 145 h | 214 h | 216.5 h |
| Mock Control | −8.7 | −8.0 | −8.0 | −8.0 | −8.0 |
| *Galdieria* Photo | +8.8 | 0.0 | 0.0 | 0.0 | 0.0 |
| *Galdieria* Mixo Glycerol | 0.0 | −8.0 | −8.0 | −8.0 | −8.0 |
| *Galdieria* Hetero Glycerol | +8.8 | +6.9 | +6.9 | +6.9 | +6.9 |
| *Chlorella* Photo | 0.0 | −8.0 | −8.0 | −8.0 | −8.0 |
| *Chlorella* Mixo Glucose | 0.0 | −8.0 | 0.0 | 0.0 | 0.0 |
| *Chlorella* Mixo Acetate | 0.0 | −8.0 | −8.0 | −8.0 | −8.0 |
| *Chlorella* Hetero Glucose | +8.8 | +6.9 | +6.9 | +6.9 | +14.9 |
| *Chlorella* Hetero Acetate | 0.0 | −8.0 | −8.0 | −8.0 | −8.0 |

TABLE 34

| Pepper | % Difference from Control (RO) regarding % Germination at Designated Time | | | | | | |
|---|---|---|---|---|---|---|---|
| Treatment | 185 h | 192.5 h | 209.5 h | 214 h | 216.5 h | 233 h | 237 h |
| Mock Control | 0.0 | −25.9 | +12.8 | +55.0 | +27.4 | +27.4 | +37.0 |
| *Galdieria* Photo | 0.0 | +48.1 | +55.3 | +45.0 | +19.2 | +37.0 | +37.0 |
| *Galdieria* Mixo Glycerol | 0.0 | 0.0 | +12.8 | +11.7 | 0.0 | +9.6 | +9.6 |
| *Galdieria* Hetero Glycerol | 0.0 | 0.0 | +12.8 | +45.0 | +27.4 | +37.0 | +37.0 |
| *Chlorella* Photo | 0.0 | 0.0 | 0.0 | 0.0 | −8.2 | 0.0 | 0.0 |
| *Chlorella* Mixo Glucose | +85.7 | +96.3 | +70.2 | +45.0 | +19.2 | +27.4 | +27.4 |
| *Chlorella* Mixo Acetate | −100.0 | −51.9 | −29.8 | −11.7 | +8.2 | +19.2 | +19.2 |
| *Chlorella* Hetero Glucose | 0.0 | +48.1 | +12.8 | +11.7 | 0.0 | +27.4 | +27.4 |
| *Chlorella* Hetero Acetate | 0.0 | −25.9 | +42.6 | +33.3 | +19.2 | +27.4 | +37.0 |

TABLE 34-continued

| Pepper | % Difference from Control (RO) regarding % Germination at Designated Time | | | | |
|---|---|---|---|---|---|
| Treatment | 240 h | 256.5 h | 260.5 h | 264 h | 280 h |
| Mock Control | +25.0 | +14.9 | 0.0 | 0.0 | 0.0 |
| *Galdieria* Photo | +25.0 | +14.9 | 0.0 | 0.0 | 0.0 |
| *Galdieria* Mixo Glycerol | 0.0 | 0.0 | −7.0 | −7.0 | −7.0 |
| *Galdieria* Hetero Glycerol | +25.0 | +14.9 | 0.0 | 0.0 | 0.0 |
| *Chlorella* Photo | −8.7 | 0.0 | −13.0 | −13.0 | −13.0 |
| *Chlorella* Mixo Glucose | +16.3 | +6.9 | 0.0 | 0.0 | 0.0 |
| *Chlorella* Mixo Acetate | +8.8 | +6.9 | 0.0 | 0.0 | 0.0 |
| *Chlorella* Hetero Glucose | +16.3 | +6.9 | −7.0 | −7.0 | 0.0 |
| *Chlorella* Hetero Acetate | +25.0 | +14.9 | 0.0 | 0.0 | 0.0 |

Example 28 (ADT 0058)

Experiments were done to test effects of microalgae compositions on corn, bean, and pepper seed germination in soil. Seeds were planted in Sunshine Mix #4 soil in trays, and germinated in a greenhouse. Fortex Pole Bean Hydro Peppers, and RD4AG Corn plant species were tested. Twelve deep 50 cell plug trays were packed with Sunshine mix #4. All trays were dibbled and then soaked in water until soil was visibly wet, but seed hole was still exposed. Solutions of treatments were made so that when 4 mL of treatment solution were applied to a single plug cell the plant received 0.04 mL of treatment. Seeds were planted at a 2 inch depth and treatment solutions were applied directly to seedosphere before hole was covered. There was a 4 mL Carrier Volume/200 mL solution: 0.04 mL treatment/plant=2 mL treatment and 198 mL reverse osmosis water (RO). Applications were applied in a random layout. Plug trays were left in greenhouse to germinate and watered every 24 hours. Plug trays were observed multiple times daily for germination:

Corn—16 observations over a total of 145 hours

Beans—17 observations over a total of 161.5 hours

Peppers—32 observations over a total of 293.5 hours.

The following treatments were tested (0.04 mL/plant in a 4 mL carrier volume [0.50 gallon/acre in furrow], all microalgae biomass for treatments in axenic flask cultures as described in Example 21):

1. *Chlorella* Hetero Acetic
2. *Chlorella* Hetero Glucose
3. *Chlorella* Mixo Acetic
4. *Chlorella* Mixo Glucose
5. *Chlorella* Photo
6. *Galdieria* Hetero Glycerol
7. *Galdieria* Mixo Glycerol
8. *Galdieria* Photo
9. *Nannochloropsis* Photo
10. *Nannochloropsis* Mixo Glucose
11. *Spirulina* Photo
12. *Spirulina* Mixo Glucose
13. Control—Reverse Osmosis (RO) water
14. Control—Mock The Mock is nutrient formulation of nutrients found in the average PhycoTerra Production Batch (i.e., *Chlorella* [HS26] Mixo Acetate)

1.5% of *Chlorella* (HS26) lipids 8.5% of protein and carbohydrates 128 ppb of Abscisic acid (ABA)

3.3 ppb of trans-ABA 2.8 ppb of trans-zeatin-O-glucoside (ZOG)

8.6 ppb of trans-zeatin (Z)

16.4 ppb of cis-Z 1.6 ppb of trans-zeatin riboside (ZR)

42.5 ppb of cis-ZR 9.8 ppb of isopentenyladenine (iP)

4.1 ppb of isopentenyladenine riboside (iPR)

86.3 ppb of indole acetic acid (IAA)

Results are shown in FIG. 1. Combined results from Examples 26-28 are shown in Tables 35-37.

TABLE 35

| Corn Treatment | % Difference from Control (RO) regarding % Germination at Designated Time | | | | | | |
|---|---|---|---|---|---|---|---|
| | 64.5 h | 68.5 h | 72.5 h | 89 h | 94 h | 97.5 h | 112 h |
| Mock Control | −100 | −100 | −42.0 | −8.1 | −7.5 | −14.0 | −14.0 |
| Galdieria Photo | −100 | +100 | −42.0 | +8.1 | +7.5 | 0.0 | 0.0 |
| Galdieria Mixo Glycerol | 0.0 | 0.0 | 0.0 | +8.1 | 0.0 | −7.0 | −7.0 |
| Galdieria Hetero Glycerol | −100 | −100 | −28.0 | 0.0 | 0.0 | 0.0 | 0.0 |
| Chlorella Photo | −100 | −100 | −28.0 | −8.1 | 0.0 | 0.0 | 0.0 |
| Chlorella Mixo Glucose | −100 | −100 | −28.0 | −8.1 | 0.0 | −7.0 | −7.0 |
| Chlorella Mixo Acetate | −100 | −100 | −42.0 | +16.3 | +7.5 | 0.0 | 0.0 |
| Chlorella Hetero Glucose | 0.0 | 0.0 | 0.0 | 0.0 | +7.5 | 0.0 | 0.0 |
| Chlorella Hetero Acetate | −100 | 0.0 | −28.0 | +16.3 | +7.5 | 0.0 | 0.0 |
| Nannochloropsis Photo | −100 | −100 | −28.0 | 0.0 | −6.5 | −13.0 | −13.0 |
| Nannochloropsis Mixo Glucose | −100 | 0.0 | +14.0 | +16.3 | +7.5 | 0.0 | 0.0 |
| Spirulina Photo | −100 | −100 | −28.0 | +16.3 | +7.5 | 0.0 | 0.0 |
| Spirulina Mixo Glucose | −100 | 0.0 | 0.0 | +16.3 | +7.5 | 0.0 | 0.0 |

| Corn Treatment | % Difference from Control (RO) regarding % Germination at Designated Time | |
|---|---|---|
| | 142.5 h | 145 h |
| Mock Control | −14.0 | −14.0 |
| Galdieria Photo | 0.0 | 0.0 |
| Galdieria Mixo Glycerol | −7.0 | −7.0 |
| Galdieria Hetero Glycerol | 0.0 | 0.0 |
| Chlorella Photo | 0.0 | 0.0 |
| Chlorella Mixo Glucose | −7.0 | 0.0 |
| Chlorella Mixo Acetate | 0.0 | 0.0 |
| Chlorella Hetero Glucose | 0.0 | 0.0 |
| Chlorella Hetero Acetate | 0.0 | 0.0 |
| Nannochloropsis Photo | −13.0 | −13.0 |
| Nannochloropsis Mixo Glucose | 0.0 | 0.0 |
| Spirulina Photo | 0.0 | 0.0 |
| Spirulina Mixo Glucose | 0.0 | 0.0 |

TABLE 36

| Bean Treatment | % Difference from Control (RO) regarding % Germination at Designated Time | | | | | | |
|---|---|---|---|---|---|---|---|
| | 68.5 h | 72.5 h | 89 h | 94 h | 97.5 h | 112 h | 117.5 h |
| Mock Control | 0.0 | +314.3 | +12.3 | 0.0 | −8.1 | +8.1 | +8.1 |
| Galdieria Photo | 0.0 | +100.0 | +24.6 | +17.7 | +8.1 | +16.3 | +16.3 |
| Galdieria Mixo Glycerol | +100.0 | +100.0 | +38.6 | +8.9 | 0.0 | 0.0 | 0.0 |
| Galdieria Hetero Glycerol | −100 | 0.0 | −12.3 | −10.1 | −17.4 | −17.4 | −17.4 |
| Chlorella Photo | 0.0 | +100.0 | +12.3 | +8.9 | 0.0 | 0.0 | 0.0 |
| Chlorella Mixo Glucose | +100.0 | +314.3 | +12.3 | −10.1 | −8.1 | 0.0 | 0.0 |
| Chlorella Mixo Acetate | +100.0 | +200.0 | +12.3 | 0.0 | −8.1 | −8.1 | −8.1 |
| Chlorella Hetero Glucose | −100.0 | +100.0 | +38.6 | +17.7 | +8.1 | +8.1 | +8.1 |
| Chlorella Hetero Acetate | +100.0 | +314.3 | +12.3 | +8.9 | +8.1 | +16.3 | +16.3 |
| Nannochloropsis Photo | +100.0 | +200.0 | −36.8 | −10.14 | −17.4 | −17.4 | −8.1 |
| Nannochloropsis Mixo Glucose | −100.0 | +314.3 | +24.6 | 0.0 | −8.1 | −8.1 | 0.0 |
| Spirulina Photo | 0.0 | +314.3 | +12.3 | −19.0 | −17.4 | 0.0 | 0.0 |
| Spirulina Mixo Glucose | −100.0 | −100.0 | −24.6 | 0.0 | −8.1 | 0.0 | +8.1 |
| Treatment | 120 h | 136.5 h | 142.5 h | 145 h | 161.5 h | | |
| Mock Control | +8.1 | +8.1 | +8.1 | +8.1 | +8.1 | | |
| Galdieria Photo | +16.3 | +16.3 | +16.3 | +16.3 | +16.3 | | |
| Galdieria Mixo Glycerol | +8.1 | +8.1 | +8.1 | +8.1 | +8.1 | | |
| Galdieria Hetero Glycerol | −17.4 | −17.4 | −17.4 | −17.4 | −17.4 | | |
| Chlorella Photo | 0.0 | 0.0 | +8.1 | +8.1 | +8.1 | | |
| Chlorella Mixo Glucose | 0.0 | 0.0 | 0.0 | 0.0 | 0.0 | | |
| Chlorella Mixo Acetate | −8.1 | −8.1 | −8.1 | −8.1 | −8.1 | | |
| Chlorella Hetero Glucose | +8.1 | +8.1 | +8.1 | +8.1 | +8.1 | | |
| Chlorella Hetero Acetate | +16.3 | +16.3 | +16.3 | +16.3 | +16.3 | | |
| Nannochloropsis Photo | −8.1 | −8.1 | 0.0 | 0.0 | 0.0 | | |
| Nannochloropsis Mixo Glucose | 0.0 | 0.0 | 0.0 | 0.0 | 0.0 | | |
| Spirulina Photo | 0.0 | 0.0 | 0.0 | 0.0 | 0.0 | | |
| Spirulina Mixo Glucose | +8.1 | +8.1 | +8.1 | +8.1 | +8.1 | | |

TABLE 37

| Pepper Treatment | % Difference from Control (RO) regarding % Germination at Designated Time | | | | | | |
|---|---|---|---|---|---|---|---|
| | 190.5 h | 193.5 h | 196.5 h | 214.5 h | 217 h | 220.5 h | 237.5 h |
| Mock Control | −10.9 | −33.7 | −17.4 | −8.1 | −15.1 | −21.0 | −21.0 |
| Galdieria Photo | −43.7 | −17.4 | −8.1 | 0.0 | 0.0 | 0.0 | 0.0 |
| Galdieria Mixo Glycerol | −33.8 | −50.0 | −41.9 | +8.1 | 0.0 | 0.0 | 0.0 |
| Galdieria Hetero Glycerol | −21.9 | −25.6 | −17.4 | 0.0 | −7.5 | −14.0 | −7.0 |
| Chlorella Photo | 0.0 | −17.4 | −8.1 | 0.0 | 0.0 | −7.0 | 0.0 |
| Chlorella Mixo Glucose | −67.2 | −33.7 | −33.7 | −8.1 | −7.5 | −14.0 | −14.0 |
| Chlorella Mixo Acetate | −21.9 | −17.4 | −8.1 | +16.3 | +7.5 | 0.0 | 0.0 |
| Chlorella Hetero Glucose | −33.8 | −41.9 | −41.9 | −8.1 | −7.5 | −7.0 | −7.0 |
| Chlorella Hetero Acetate | −54.7 | −33.7 | −33.7 | −17.4 | −23.7 | −29.0 | −29.0 |
| Nannochloropsis Photo | 0.0 | −25.6 | −25.6 | −25.6 | −23.7 | −21.0 | −21.0 |

TABLE 37-continued

| Pepper | % Difference from Control (RO) regarding % Germination at Designated Time | | | | | | |
|---|---|---|---|---|---|---|---|
| Nannochloropsis Mixo Glucose | −10.9 | −8.1 | −8.1 | +16.3 | +7.5 | 0.0 | 0.0 |
| Spirulina Photo | −54.7 | −50.0 | −50.0 | −17.4 | −7.5 | −14.0 | −14.0 |
| Spirulina Mixo Glucose | −54.7 | −50.0 | −33.7 | 0.0 | 0.0 | 0.0 | 0.0 |

| Treatment | 242 h | 245.5 h | 261h | 267 h | 286.5 h | 293.5 h | 406 h |
|---|---|---|---|---|---|---|---|
| Mock Control | −21.0 | −21.0 | −21.0 | −21.0 | −21.0 | −21.0 | 0.0 |
| Galdieria Photo | 0.0 | 0.0 | 0.0 | 0.0 | 0.0 | 0.0 | 0.0 |
| Galdieria Mixo Glycerol | 0.0 | 0.0 | 0.0 | 0.0 | 0.0 | 0.0 | 0.0 |
| Galdieria Hetero Glycerol | −7.0 | −7.0 | −7.0 | 0.0 | 0.0 | 0.0 | 0.0 |
| Chlorella Photo | 0.0 | 0.0 | 0.0 | 0.0 | 0.0 | 0.0 | 0.0 |
| Chlorella Mixo Glucose | −14.0 | −14.0 | −14.0 | −14.0 | −14.0 | 0.0 | 0.0 |
| Chlorella Mixo Acetate | 0.0 | 0.0 | 0.0 | 0.0 | 0.0 | 0.0 | 0.0 |
| Chlorella Hetero Glucose | −7.0 | 0.0 | 0.0 | 0.0 | 0.0 | 0.0 | 0.0 |
| Chlorella Hetero Acetate | −29.0 | −21.0 | −7.0 | 0.0 | 0.0 | 0.0 | 0.0 |
| Nannochloropsis Photo | −21.0 | −1.0 | −14.0 | −14.0 | −14.0 | 0-14.0 | 0.0 |
| Nannochloropsis Mixo Glucose | 0.0 | 0.0 | 0.0 | 0.0 | 0.0 | 0.0 | 0.0 |
| Spirulina Photo | −7.0 | −7.0 | −7.0 | −7.0 | −7.0 | −7.0 | 0.0 |
| Spirulina Mixo Glucose | 0.0 | 0.0 | 0.0 | 0.0 | 0.0 | 0.0 | 0.0 |

Example 29 (ADT 0056)

Experiments were done to test the effects of microalgae-based compositions on germination of corn seeds subjected to temperature stress. In these experiments, all seeds began in 26° C. conditions for 15.5 hours; experienced a period of temperature stress (Cold period of 5° C., Heat period of 50° C., Normal always at 26° C.) for 8 hours; after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. An application rate of 9 mL/gal was selected after comparison of 2.25 mL/gallon, 4.5 mL/gallon, 9 mL/gallon, and 18 mL/gallon and there was found to be no statistical difference for the 9 mL/gallon rate with respect to the control or other tested application rates. The biomass was produced in axenic flask cultures as described in Example 21.

1. Chlorella Hetero Acetate
2. Chlorella Hetero Glucose
3. Chlorella Mixo Acetate
4. Chlorella Mixo Glucose
5. Chlorella Photo
6. Control—Mock ((Mock is nutrient formulation of nutrients found in the average PhycoTerra Production Batch (i.e., Chlorella [HS26] Mixo Acetate)
   MOCK:
   1.5% of Chlorella (HS26) lipids
   8.5% of protein and carbohydrates
   128 ppb of Abscisic acid (ABA)
   3.3 ppb of trans-ABA
   2.8 ppb of trans-zeatin-O-glucoside (ZOG)
   8.6 ppb of trans-zeatin (Z)
   16.4 ppb of cis-Z
   1.6 ppb of trans-zeatin riboside (ZR)
   42.5 ppb of cis-ZR
   9.8 ppb of isopentenyladenine (iP)
   4.1 ppb of isopentenyladenine riboside (iPR)
   86.3 ppb of indole acetic acid (IAA)
7. Control—PhycoTerra Production Batch (Chlorella [HS26] Mixo Acetate produced outdoors in open culture)
8. Control—Reverse Osmosis (RO) Water Percent germination was determined with observations occurring multiple times per day. The criteria for counting germination was when the radical root was at least 1 mm in length. Percent germination was analyzed as a complete time series for each experiment and using a Dunnet's test to compare treatments to untreated control at 25 hours for normal temperatures, and 45 hours for temperature stressed experiments. Results are shown in Tables 38-40.

TABLE 38

| Treatment | Temperature | % Difference from Control (RO) of % Germination at 23.5 h |
|---|---|---|
| Chlorella Hetero Acetate | Normal | +3.7 |
| Chlorella Hetero Glucose | Normal | +22.2 |
| Chlorella Mixo Acetate | Normal | +3.7 |
| Chlorella Mixo Glucose | Normal | +26.0 |
| Chlorella Photo | Normal | +11.2 |
| Mock | Normal | +29.7 |
| Production Batch | Normal | −14.8 |

TABLE 39

| Treatment | Temperature | % Difference from Control (RO) of % Germination at 45 h |
|---|---|---|
| *Chlorella* Hetero Acetate | Cold Stress | −4.6 |
| *Chlorella* Hetero Glucose | Cold Stress | +2.2 |
| *Chlorella* Mixo Acetate | Cold Stress | 0.0 |
| *Chlorella* Mixo Glucose | Cold Stress | +2.2 |
| *Chlorella* Photo | Cold Stress | −2.2 |
| Mock | Cold Stress | −2.2 |
| Production Batch | Cold Stress | 0.0 |

TABLE 40

| Treatment | Temperature | % Difference from Control (RO) of % Germination at 45 h |
|---|---|---|
| *Chlorella* Hetero Acetate | Heat Stress | +13.7 |
| *Chlorella* Hetero Glucose | Heat Stress | +18.2 |
| *Chlorella* Mixo Acetate | Heat Stress | +18.2 |
| *Chlorella* Mixo Glucose | Heat Stress | +40.9 |
| *Chlorella* Photo | Heat Stress | +9.0 |
| Mock | Heat Stress | +4.5 |
| Production Batch | Heat Stress | +9.2 |

Example 30 (ADT 0061)

Experiments were done to test the effects of microalgae-based compositions on germination of corn seed subjected to temperature stress. In these experiments, all seeds began in 26° C. conditions for 6 hours; experienced a period of temperature stress (Cold period of 0° C., Heat period of 45° C., Normal always at 26° C.) for 15 hours; after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.
 1. *Chlorella* Hetero Acetate
 2. *Chlorella* Hetero Glucose
 3. *Chlorella* Mixo Acetate
 4. *Chlorella* Mixo Glucose
 5. *Chlorella* Photo
 6. Control—Mock ((Mock is nutrient formulation of nutrients found in the average PhycoTerra Production Batch (i.e., *Chlorella* [HS26] Mixo Acetate)
  MOCK:
   1.5% of *Chlorella* (HS26) lipids
   8.5% of protein and carbohydrates
   128 ppb of Abscisic acid (ABA)
   3.3 ppb of trans-ABA
   2.8 ppb of trans-zeatin-O-glucoside (ZOG)
   8.6 ppb of trans-zeatin (Z)
   16.4 ppb of cis-Z
   1.6 ppb of trans-zeatin riboside (ZR)
   42.5 ppb of cis-ZR
   9.8 ppb of isopentenyladenine (iP)
   4.1 ppb of isopentenyladenine riboside (iPR)
   86.3 ppb of indole acetic acid (IAA)
 7. Control—PhycoTerra Production Batch (*Chlorella* Mixo Acetate produced outdoors in open culture)
 8. Control—Reverse Osmosis (RO) Water Percent germination was determined with observations occurring multiple times per day. The criteria for counting germination was when the radical root was at least 1 mm in length. Percent germination was analyzed as a complete time series for each experiment and using a Dunnet's test to compare treatments to untreated control at 25 hours for normal temperatures, and 45 hours for temperature stressed experiments. Dry Weight (g) of plants was determined in heat stress experiments. Results are shown in Tables 41-43.

TABLE 41

| Treatment | Temperature | % Difference from Control (RO) of % Germination at 21 h |
|---|---|---|
| *Chlorella* Hetero Acetate | Normal | −22.2 |
| *Chlorella* Hetero Glucose | Normal | +11.1 |
| *Chlorella* Mixo Acetate | Normal | +44.5 |
| *Chlorella* Mixo Glucose | Normal | +55.6 |
| *Chlorella* Photo | Normal | +33.4 |
| Mock | Normal | +44.5 |
| Production Batch | Normal | +88.9 |

TABLE 42

| Treatment | Temperature | % Difference from Control (RO) of % Germination at 45 h |
|---|---|---|
| *Chlorella* Hetero Acetate | Cold Stress | +35.7 |
| *Chlorella* Hetero Glucose | Cold Stress | +35.7 |
| *Chlorella* Mixo Acetate | Cold Stress | +10.7 |
| *Chlorella* Mixo Glucose | Cold Stress | +10.7 |
| *Chlorella* Photo | Cold Stress | +39.3 |
| Mock | Cold Stress | +39.3 |
| Production Batch | Cold Stress | +32.1 |

TABLE 43

| Treatment | Temperature | % Difference from Control (RO) of % Germination at 45 h |
|---|---|---|
| *Chlorella* Hetero Acetate | Heat Stress | −12.5 |
| *Chlorella* Hetero Glucose | Heat Stress | −40.6 |
| *Chlorella* Mixo Acetate | Heat Stress | −12.5 |
| *Chlorella* Mixo Glucose | Heat Stress | −34.4 |
| *Chlorella* Photo | Heat Stress | +6.3 |
| Mock | Heat Stress | −25.0 |
| Production Batch | Heat Stress | −43.7 |

TABLE 44

| Treatment | ADT0061 Dry Weight (g) | ADT0063 Dry Weight (g) |
|---|---|---|
| RO Control | 2.71 | 2.15 |
| Mock | 2.23 | 2.55 |
| Production Batch | 2.02 | no test |
| *Chlorella* Photo | 2.80 | 2.31 |
| *Chlorella* Hetero Acetate | 2.21 | 2.27 |
| *Chlorella* Hetero Glucose | 2.07 | 3.09 |
| *Chlorella* Mixo Acetate | 2.65 | 2.40 |
| *Chlorella* Mixo Glucose | 2.05 | 2.78 |
| Nanno Photo | no test | 2.95 |
| Nano Mixo Glucose | no test | 2.46 |
| Spirulina Mixo Glucose | no test | 2.71 |
| Spirulina Photo | no test | 2.88 |

Example 31 (ADT 0063)

Experiments were done to test the effects of microalgae-based compositions on germination of corn seed subjected to temperature stress. In these experiments, all seeds began in 26° C. conditions for 6 hours; experienced a period of temperature stress (Cold period of 24 hours at 0° C., Heat period of 15 hours at 45° C., Normal always at 26° C.); after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.
 1. *Chlorella* Hetero Acetate
 2. *Chlorella* Hetero Glucose
 3. *Chlorella* Mixo Acetate
 4. *Chlorella* Mixo Glucose
 5. *Chlorella* Photo
 6. *Nannochloropsis* Mixo Glucose
 7. *Nannochloropsis* Photo
 8. *Spirulina* Mixo Glucose
 9. *Spirulina* Photo
 10. Control—Mock ((Mock is nutrient formulation of nutrients found in the average PhycoTerra Production Batch (i.e., *Chlorella* [HS26] Mixo Acetate)
   MOCK:
     1.5% of *Chlorella* (HS26) lipids
     8.5% of protein and carbohydrates
     128 ppb of Abscisic acid (ABA)
     3.3 ppb of trans-ABA
     2.8 ppb of trans-zeatin-O-glucoside (ZOG)
     8.6 ppb of trans-zeatin (Z)
     16.4 ppb of cis-Z
     1.6 ppb of trans-zeatin riboside (ZR)
     42.5 ppb of cis-ZR
     9.8 ppb of isopentenyladenine (iP)
     4.1 ppb of isopentenyladenine riboside (iPR)
     86.3 ppb of indole acetic acid (IAA)
 11. Control—Reverse Osmosis (RO) Water Percent germination was determined with observations occurring multiple times per day. The criteria for counting germination was when the radical root was at least 1 mm in length. Dry Weight (g) of plants was determined in heat stress experiments. Combined results from Examples 30 and 31 are shown in FIGS. 13-14 and Tables 45-47.

TABLE 45

| Treatment | Temperature | % Difference from Control (RO) of % Germination at 28 h |
| --- | --- | --- |
| Spirulina Photo | Normal | −22.5 |
| Spirulina Mixo Glucose | Normal | −12.5 |
| Nannochloropsis Photo | Normal | −25.0 |
| Nannochloropsis Mixo Glucose | Normal | −25.0 |
| Chlorella Hetero Acetate | Normal | −12.5 |
| Chlorella Hetero Glucose | Normal | −32.5 |
| Chlorella Mixo Acetate | Normal | −5.0 |
| Chlorella Mixo Glucose | Normal | −20.0 |
| Chlorella Photo | Normal | −22.5 |
| Mock | Normal | −20.0 |

TABLE 46

| Treatment | Temperature | % Difference from Control (RO) of % Germination at 44.5 h |
| --- | --- | --- |
| Spirulina Photo | Cold Stress | +75.0 |
| Spirulina Mixo Glucose | Cold Stress | +33.3 |
| Nannochloropsis Photo | Cold Stress | +83.3 |
| Nannochloropsis Mixo Glucose | Cold Stress | +83.3 |
| Chlorella Hetero Acetate | Cold Stress | +25.0 |
| Chlorella Hetero Glucose | Cold Stress | +41.7 |
| Chlorella Mixo Acetate | Cold Stress | +50.0 |
| Chlorella Mixo Glucose | Cold Stress | +41.7 |
| Chlorella Photo | Cold Stress | +25.0 |
| Mock | Cold Stress | +16.6 |

TABLE 47

| Treatment | Temperature | % Difference from Control (RO) of % Germination at 44.5 h |
| --- | --- | --- |
| Spirulina Photo | Heat Stress | +27.3 |
| Spirulina Mixo Glucose | Heat Stress | +40.9 |
| Nannochloropsis Photo | Heat Stress | +13.6 |
| Nannochloropsis Mixo Glucose | Heat Stress | −18.2 |
| Chlorella Hetero Acetate | Heat Stress | +18.2 |
| Chlorella Hetero Glucose | Heat Stress | +63.6 |
| Chlorella Mixo Acetate | Heat Stress | +27.3 |
| Chlorella Mixo Glucose | Heat Stress | +22.7 |
| Chlorella Photo | Heat Stress | +18.2 |
| Mock | Heat Stress | 0.0 |

Example 32 (ADT 0066)

Experiments were done to test the effects of microalgae-based compositions on germination of corn seed subjected to temperature stress. In these experiments, all seeds began in 26° C. conditions for 6 hours; experienced a period of temperature stress (Cold period of 24 hours at 0° C., Heat period of 15 hours at 45° C., Normal always at 26° C.); after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.
 1. *Chlorella* Hetero Acetate
 2. *Chlorella* Hetero Glucose
 3. *Chlorella* Mixo Acetate
 4. *Chlorella* Mixo Glucose
 5. *Chlorella* Photo
 6. *Nannochloropsis* Mixo Glucose
 7. *Nannochloropsis* Photo
 8. *Spirulina* Mixo Glucose
 9. *Spirulina* Photo
 10. Control—Mock ((Mock is nutrient formulation of nutrients found in the average PhycoTerra Production Batch (i.e., *Chlorella* [HS26] Mixo Acetate)
   MOCK:
     1.5% of *Chlorella* (HS26) lipids
     8.5% of protein and carbohydrates
     128 ppb of Abscisic acid (ABA)
     3.3 ppb of trans-ABA
     2.8 ppb of trans-zeatin-O-glucoside (ZOG)
     8.6 ppb of trans-zeatin (Z)

16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

11. Control—Reverse Osmosis (RO) Water

Figure 2:
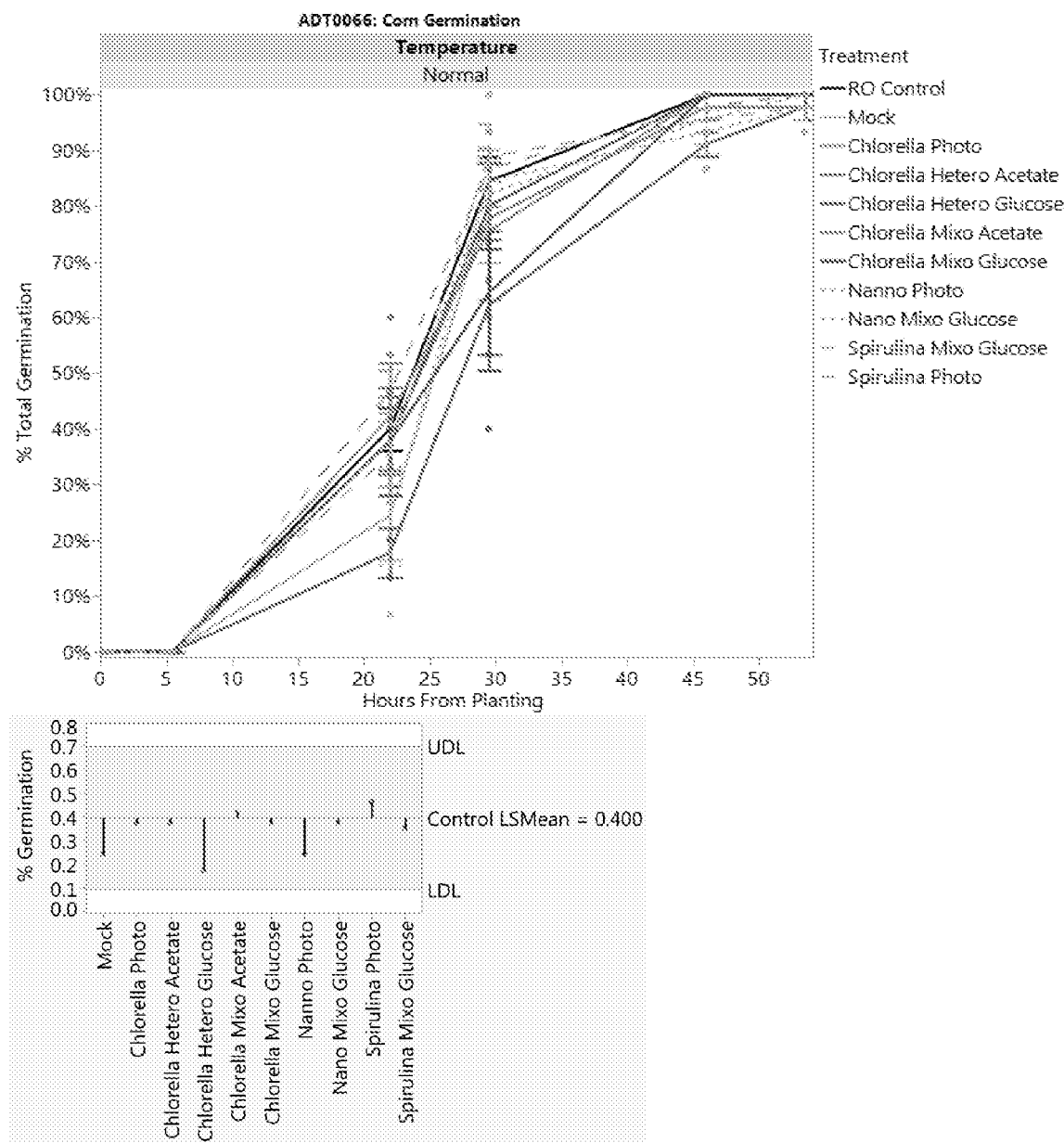
FIG. 2 depicts results of experiments involving microalgae-based compositions on corn, bean and pepper seed germination.
Figure 2:
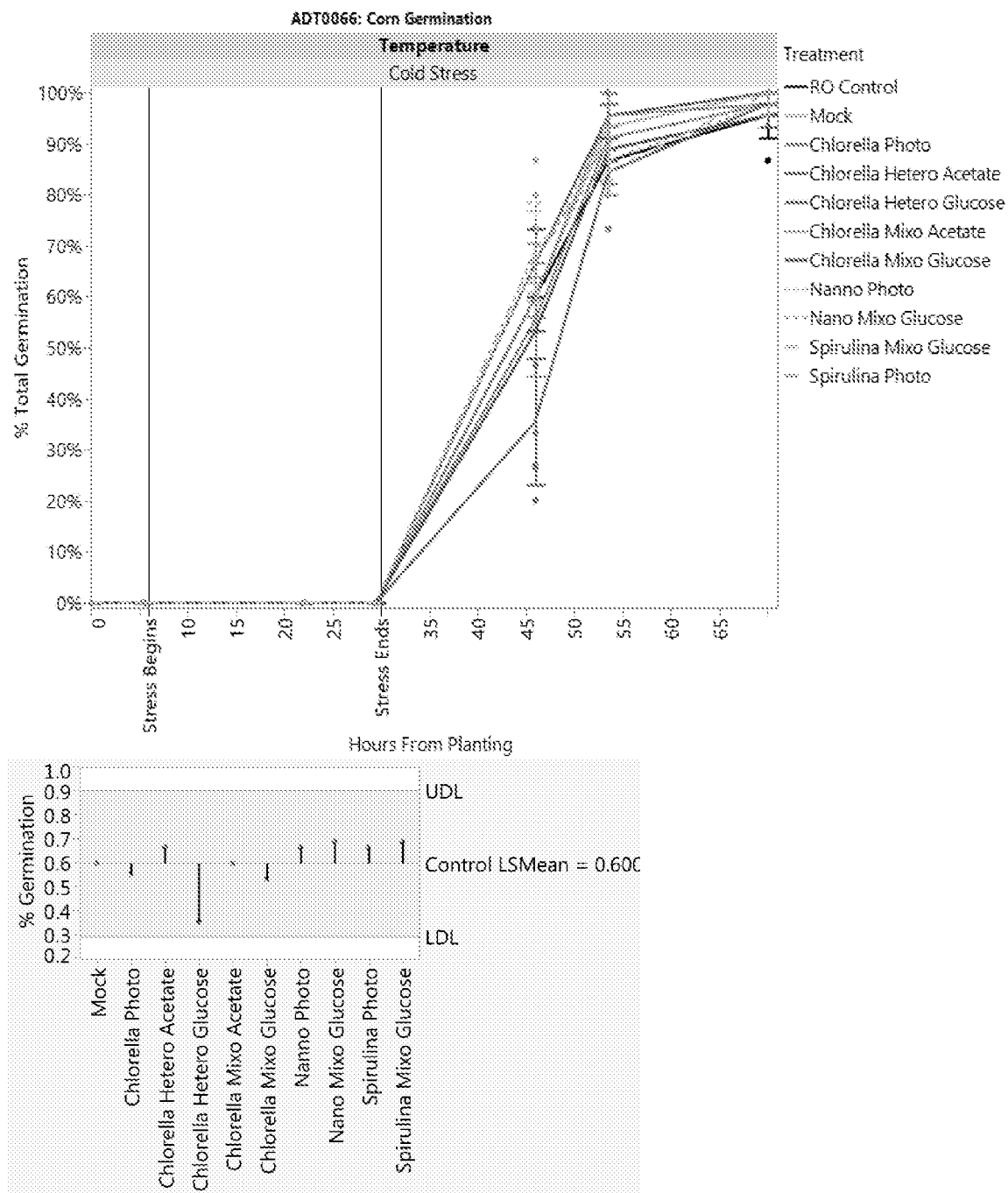
Figure 2:
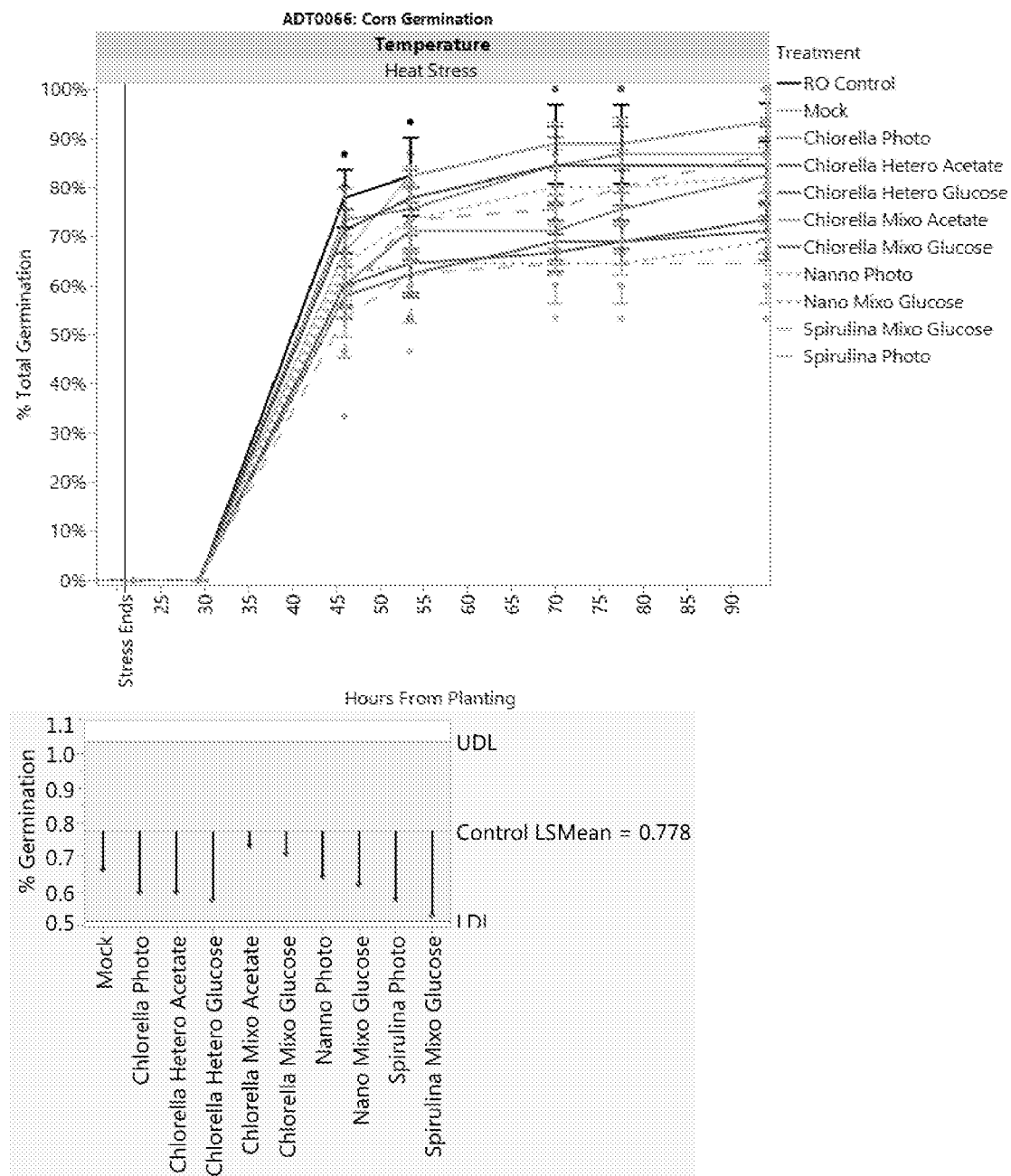

Percent germination was determined with observations occurring multiple times per day. The criteria for counting germination was when the radical root was at least 1 mm in length. Percent germination was analyzed as a complete time series for each experiment and using a Dunnet's test to compare treatments to untreated control at 25 hours for normal temperatures, and 45 hours for temperature stressed experiments. Results are shown in FIG. 2. Combined results from Examples 29-31 standardized to the RO Control are shown in Tables 48-50.

TABLE 48

| Treatment | Temperature | % Difference from Control (RO) of % Germination at 22 h |
|---|---|---|
| Spirulina Photo | Normal | +16.7 |
| Spirulina Mixo Glucose | Normal | −11.1 |
| Nannochloropsis Photo | Normal | −38.9 |
| Nannochloropsis Mixo Glucose | Normal | −5.5 |
| Chlorella Hetero Acetate | Normal | −5.5 |
| Chlorella Hetero Glucose | Normal | −55.5 |
| Chlorella Mixo Acetate | Normal | +5.6 |
| Chlorella Mixo Glucose | Normal | −5.5 |
| Chlorella Photo | Normal | −5.5 |
| Mock | Normal | −38.9 |

TABLE 49

| Treatment | Temperature | % Difference from Control (RO) of % Germination at 46 h |
|---|---|---|
| Spirulina Photo | Cold Stress | +11.1 |
| Spirulina Mixo Glucose | Cold Stress | +14.8 |
| Nannochloropsis Photo | Cold Stress | +11.1 |
| Nannochloropsis Mixo Glucose | Cold Stress | +14.8 |
| Chlorella Hetero Acetate | Cold Stress | +11.1 |
| Chlorella Hetero Glucose | Cold Stress | −40.7 |
| Chlorella Mixo Acetate | Cold Stress | 0.0 |
| Chlorella Mixo Glucose | Cold Stress | −11.1 |
| Chlorella Photo | Cold Stress | −7.4 |
| Mock | Cold Stress | 0.0 |

TABLE 50

| Treatment | Temperature | % Difference from Control (RO) of % Germination at 46 h |
|---|---|---|
| Spirulina Photo | Heat Stress | −25.7 |
| Spirulina Mixo Glucose | Heat Stress | −31.4 |
| Nannochloropsis Photo | Heat Stress | −17.2 |
| Nannochloropsis Mixo Glucose | Heat Stress | −20.0 |
| Chlorella Hetero Acetate | Heat Stress | −22.9 |
| Chlorella Hetero Glucose | Heat Stress | −25.7 |
| Chlorella Mixo Acetate | Heat Stress | −5.7 |
| Chlorella Mixo Glucose | Heat Stress | −8.6 |
| Chlorella Photo | Heat Stress | −22.9 |
| Mock | Heat Stress | −14.3 |

Example 33 (ADT 0069)

Experiments were done to test the effects of microalgae-based compositions on germination of corn seed subjected to temperature stress. In these experiments, all seeds began in 26° C. conditions for 6 hours; experienced a period of temperature stress (Cold period of 24 hours at 0° C., Heat period of 15 hours at 45° C., Normal always at 26° C.); after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.

1. Chlorella Hetero Acetate
2. Chlorella Hetero Glucose
3. Chlorella Mixo Acetate
4. Chlorella Mixo Glucose
5. Chlorella Photo
6. Galdieria Hetero Glucose
7. Galdieria Mixo Glucose
8. Haematococcus Mixo Acetate
9. Haematococcus Photo
10. Control—Mock Mock is nutrient formulation of nutrients found in the average PhycoTerra Production Batch (i.e., Chlorella [HS26] Mixo Acetate)

1.5% of Chlorella (HS26) lipids
8.5% of protein and carbohydrates
128 ppb of Abscisic acid (ABA)
3.3 ppb of trans-ABA
2.8 ppb of trans-zeatin-O-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

Percent germination was determined once for each temperature, 24 hours after seeding for normal temperatures and 45 hours after seeding for cold and heat stress; The criteria for counting germination was when the radical root was at least 1 mm in length. Results are shown in Tables 51-53.

TABLE 51

| Treatment | Temperature | % Difference from Control (RO) of % Germination at 24 h |
|---|---|---|
| Mock | Normal | −18.7 |
| Chlorella Photo | Normal | −40.6 |
| Chlorella Mixo Glucose | Normal | −25.0 |
| Chlorella Mixo Acetate | Normal | −9.4 |
| Chlorella Hetero Glucose | Normal | −6.2 |
| Chlorella Hetero Acetate | Normal | −15.6 |
| Haematococcus Photo | Normal | −15.6 |
| Haematococcus Mixo Acetate | Normal | −12.5 |
| Galdieria Mixo Glucose | Normal | −25.0 |
| Galdieria Hetero Glucose | Normal | −12.5 |

TABLE 52

| Treatment | Temperature | % Difference from Control (RO) of % Germination at 45 h |
|---|---|---|
| Mock | Cold Stress | −30.3 |
| Chlorella Photo | Cold Stress | −34.8 |

TABLE 52-continued

| Treatment | Temperature | % Difference from Control (RO) of % Germination at 45 h |
|---|---|---|
| Chlorella Mixo Glucose | Cold Stress | −26.0 |
| Chlorella Mixo Acetate | Cold Stress | −30.3 |
| Chlorella Hetero Glucose | Cold Stress | +4.3 |
| Chlorella Hetero Acetate | Cold Stress | −21.7 |
| Haematococcus Photo | Cold Stress | +17.4 |
| Haematococcus Mixo Acetate | Cold Stress | −21.7 |
| Galdieria Mixo Glucose | Cold Stress | 0.0 |
| Galdieria Hetero Glucose | Cold Stress | −13.1 |

TABLE 53

| Treatment | Temperature | % Difference from Control (RO) of % Germination at 45 h |
|---|---|---|
| Mock | Heat Stress | −61.2 |
| Chlorella Photo | Heat Stress | −41.9 |
| Chlorella Mixo Glucose | Heat Stress | −38.8 |
| Chlorella Mixo Acetate | Heat Stress | −22.6 |
| Chlorella Hetero Glucose | Heat Stress | −3.2 |
| Chlorella Hetero Acetate | Heat Stress | −19.3 |
| Haematococcus Photo | Heat Stress | −3.2 |
| Haematococcus Mixo Acetate | Heat Stress | −22.6 |
| Galdieria Mixo Glucose | Heat Stress | −12.9 |
| Galdieria Hetero Glucose | Heat Stress | −35.6 |

TABLE 54

| | % Difference From Treatment with no Microalgae for % Germination at Designated Time | | | | | | | |
|---|---|---|---|---|---|---|---|---|
| Treatment | 20.5 h | 28h | 44.5 h | 52 h | 68.5 h | 76 h | 92.5 h | Points of largest spread |
| RO + microalgae | −36.3 | −23.1 | −4.4 | −2.2 | −2.2 | −2.2 | −2.2 | −23.1 |
| 200 mMol salt + microalgae | — | +200.5 | −33.3 | 0.0 | −5.9 | −8.6 | −8.6 | −33.3 |
| 220 mMOl salt + microalgae | — | −33.3 | −15.4 | −9.1 | 0.0 | 0.0 | 0.0 | −15.4 |

TABLE 55

| Treatment | Tissue Water Content (%) | Fresh Weight (g) | Dry Weight (g) |
|---|---|---|---|
| RO Water | 55% | 7.25 | 3.24 |
| RO + PT | 56% | 7.53 | 3.27 |
| 200 mMol salt | 50% | 5.14 | 2.55 |
| 200 mMol salt + PT | 55% | 5.11 | 2.34 |
| 220 mMol salt | 52% | 5.15 | 2.48 |
| 220 mMol salt + PT | 50% | 5.15 | 2.55 |
| PT soak/220 mMol salt | 60% | 4.97 | 2.02 |

Example 34 (ADT 0064)

Experiments were done to test the effects of microalgae-based compositions on germination of corn seeds subjected to salt stress. In these experiments, petri plates were lined with filter paper water with 10 mL of treatment solutions (application rate/concentration of 9 mL/gallon) one time at the beginning of the experiment. The plates located in a temperature chamber to control the temperature conditions. Triplicate plates with 15 corn seeds were used on each plate. The seeds in the soak treatment were soaked for two hours.

1. Control—Reverse Osmosis (RO) Water
2. Control—RO water+PhycoTerra Production Batch (*Chlorella* Mixo [HS26] Acetate produced outdoors in open culture)
3. 200 mM salt ((NaCl in RO water)
4. 200 mM salt (NaCl in RO water)+PhycoTerra Production Batch
5. 220 mM salt (NaCl in RO water)
6. 220 mM salt (NaCl in RO water)+PhycoTerra Production Batch
7. PhycoTerra Production Batch Soak/220 mM salt (NaCl in RO water)

Percent germination was determined with observations occurring multiple times per day. The criteria for counting germination was when the radical root was at least 1 mm in length. Results are shown in Table 54.

Example 35 (ADT 0067)

Experiments were done to test the effects of microalgae-based compositions on germination of corn seeds subjected to salt stress. In these experiments, petri plates were lined with filter paper water with 10 mL of treatment solutions (application rate/concentration of 9 mL/gallon) one time at the beginning of the experiment. The plates located in a temperature chamber to control the temperature conditions. The triplicate plates with 15 corn seeds were on each plate. The seeds in the soak treatment were soaked for two hours.

1. Control—Reverse Osmosis (RO) Water
2. Control—RO water+PhycoTerra Production Batch (*Chlorella* [HS26] Mixo Acetate produced outdoors in open culture)
3. 200 mM salt ((NaCl in RO water)
4. 200 mM salt (NaCl in RO water)+PhycoTerra Production Batch
5. 220 mM salt (NaCl in RO water)
6. 220 mM salt (NaCl in RO water)+PhycoTerra Production Batch
7. PhycoTerra Production Batch Soak/220 mM salt (NaCl in RO water)

Percent germination was determined with observations occurring multiple times per day. The criteria for counting germination was when the radical root was at least 1 mm in length. Results are shown in Tables 56-57.

TABLE 56

% Difference From Treatment with no Microalgae for
% Germination at Designated Time

| Treatment | 29 h | 45.5 h | 53 h | 69.5 h | 77 h | 93.5 h | 101 h | 117.5 h |
|---|---|---|---|---|---|---|---|---|
| RO + microalgae | −7.4 | 0.0 | 0.0 | 0.0 | 0.0 | 0.0 | 0.0 | 0.0 |
| 200 mMol salt + microalgae | −33.1 | −56.7 | −51.4 | −44.2 | −41.3 | −41.3 | −34.3 | −34.3 |
| 220 mMOl salt + microalgae | −40.4 | −27.2 | −23.2 | −11.2 | −12.9 | −12.8 | −18.1 | −18.1 |

TABLE 57

% Difference From Treatment with no Microalgae

| Treatment | Seed Weight | Fresh Weight | Dry Weight | STD Dry Content | Water |
|---|---|---|---|---|---|
| RO + microalgae | −1.2 | −18.5 | +0.1 | +0.1 | −16.9 |
| 200 mMol salt + microalgae | −1.8 | −17.5 | −0.7 | −38.1 | +7.8 |
| 220 mMOl salt + microalgae | −1.2 | −15.7 | −2.1 | −21.2 | +0.2 |

Example 36 (Hydroponic 1)

Experiments were done to test the effects of microalgae-based compositions administered hydroponically on bell peppers. In these experiments, the microalgae biomass for the identified treatments was produced in bag bioreactors (Example 21). Germinated pepper seedlings were grown in 4 inch pots with Turface-a calcined clay substrate. Everyday all plants were fertilized with 150 mL of nutrient solution (i.e., the Veg Only composition) to which various microalgae treatments were added at a concentration of 9 mL/gallon. The trays were randomized and location switched within the testing platform on one week schedules. All of the trays were harvested 22 days after the start of the experiment due to a pest infestation. The treatments tested comprised:

1. Control—Veg Only1
2. Control—Veg Only2

Both Veg Only Controls comprise the following nutrients:
$KH_2PO_4$
$KNO_3$
$Ca(NO_3)_2$ $4H_2O$
$MgSO_4$ $7H_2O$
$NaFe(III)EDTA$
$H_3HO_3$
$MnC_{12}$ $4H_2O$
$ZnSO_4$ $7H_2O$
$CuSO_4$ $5H_2O$
$Na_2MoO_3$ 3. Control—PhycoTerra Production Batch # HG160303 (*Chlorella* [HS26] Mixo Acetate produced outdoors in open culture)
4. *Chlorella* Photo
5. *Chlorella* Mixo Acetate
6. *Chlorella* Mixo Glucose
7. *Chlorella* Hetero Acetate
8. *Chlorella* Hetero Glucose
9. *Haematococcus* Photo
10. *Haematococcus* Mixo Acetate
11. *Galdieria* Hetero Glucose
12. *Galdieria* Mixo Glucose
13. *Scenedesmus* Photo
14. *Scenedesmus* Mixo Acetate
15. *Scenedesmus* Mixo Glucose
16. *Scenedesmus* Hetero Glucose
17. *Chlamydomonas* Mixo Acetate
18. *Chlamydomonas* Photo A damage score at the time of harvest was observed for all plants, as well as a plant dry weight (g). The *Chlamydomonas* treatments were not applied to plants but were analyzed for micronutrient content. Below is a table of Micronutrient analysis of microalgal biomass used in treatments (questionable values are shaded).

| Treat | pH (SU) | Chloride, Cl (ppm) | Cobalt, Co (ppb) | Molybdenum, Mo (ppb) | Phosphorus, $P_2O_5$ (%) | Potassium, $K_2O$ (%) | Calcium, Ca (%) | Magnesium, Mg (%) | Sodium, Na (%) | Sulfur, S (%) | Iron, Fe (ppm) |
|---|---|---|---|---|---|---|---|---|---|---|---|
| Veg Only | 0.9 | 7.74 | <10 | 10 | 10 | 0.019 | 0.016 | 0.0052 | 0.0012 | 0.0067 | 2.2 |
| HG160303 | 3 | 141 | 130 | 170 | 0.86 | 0.16 | 0.045 | 0.017 | 0.052 | 0.047 | 29 |
| Photo Chlorella | 3.8 | 65 | 250 | 160 | 0.82 | 0.27 | 0.045 | 0.042 | 0.037 | 0.067 | 38 |
| Mixo Acetate Chlorella | 3.8 | 34 | 20 | 240 | 0.23 | 0.13 | 0.031 | 0.0083 | 0.022 | 0.005 | 45 |
| Mixo Glucose Chlorella | 3.8 | 123 | 190 | 930 | .68 | 0.21 | 0.038 | 0.022 | 0.065 | 0.036 | 18 |
| Hetero Acetate Chlorella | 3.8 | 111 | 120 | 200 | 0.4 | 0.14 | 0.036 | 0.017 | 0.061 | 0.039 | 22 |
| Hetero Glucose Chlorella | 3.9 | 90 | 120 | 480 | 0.8 | 0.29 | 0.037 | 0.028 | 0.093 | 0.068 | 23 |
| Photo Haematococcus | 4 | 85 | 0.69 | 800 | 0.9 | 0.25 | 0.041 | 0.048 | 0.0093 | 0.054 | 52 |
| Mixo Haematococcus | 4.2 | 131 | 10 | 1270 | 0.63 | 0.21 | 0.033 | 0.029 | 0.015 | 0.05 | 19 |
| Mixo Galdieria | 3.9 | 246 | 440 | 570 | 0.36 | 0.11 | 0.028 | 0.013 | 0.047 | 0.026 | 62 |
| Hetero Glucose Galdieria | 3.8 | 208 | 1150 | 890 | 0.72 | 0.14 | 0.032 | 0.027 | 0.04 | 0.068 | 45 |
| Photo Scenedesmus | 4.1 | 65 | 100 | 310 | 0.82 | 0.25 | 0.031 | 0.038 | 0.036 | 0.059 | 36 |
| Mixo Acetate Scenedesmus | 4 | 147 | 120 | 5150 | 0.73 | 0.16 | 0.029 | 0.026 | 0.049 | 0.057 | 42 |
| Mixo Glucose Scenedesmus | 3.8 | 169 | 140 | 2780 | 0.8 | 0.18 | 0.028 | 0.019 | 0.031 | 0.04 | 25 |

-continued

| | | | | | | | | | | |
|---|---|---|---|---|---|---|---|---|---|---|
| Hetero Glucose Scenedesmus | 3.8 | 47 | 80 | 1690 | 0.83 | 0.19 | 0.028 | 0.017 | 0.029 | 0.04 | 22 |
| Mixo Acetate Chlamydomonas | 3.5 | 65 | 10 | 220 | 0.95 | 0.14 | 0.038 | 0.027 | 0.031 | 0.057 | 27 |
| Photo Chlamydomonas | 3.7 | 93 | 0.93 | 140 | 0.93 | 0.13 | 0.077 | 0.042 | 0.012 | 0.056 | 34 |

| Treat | Zinc, Zn (ppm) | Manganese, Mn (ppm) | Copper, Cu (ppm) | Boron, B (ppm) | Ammonium-Nitrogen, NH4-N (ppm) | Nitrate-Nitrogen, NO3-N (ppm) | Insoluble Nitrogen (ppm) | Total Nitrogen, N (ppm) | Moisture (%) | Dry Matter (%) |
|---|---|---|---|---|---|---|---|---|---|---|
| Veg Only | 0.46 | 0.26 | 0.026 | 0.61 | 22.5 | 201 | 811 | 1,034 | 99.9 | 0.1 |
| HG160303 | 1.5 | 3 | 1.2 | 0.77 | 270 | 105 | 4,448 | 4,823 | 88.2 | 11.8 |
| Photo Chlorella | 6 | 13 | 2.7 | 0.62 | 81.6 | 203 | 6,830 | 7,115 | 88.8 | 11.2 |
| Mixo Acetate Chlorella | 1.1 | 1.2 | 1.2 | 0.39 | 43.8 | 124 | 2,415 | 2,583 | 95.2 | 11.3 |
| Mixo Glucose Chlorella | 3.2 | 12 | 1.9 | 1.2 | 88.9 | 101 | 9,249 | 9,301 | 89.1 | 10.9 |
| Hetero Acetate Chlorella | 3.3 | 9.6 | 1.8 | 1 | 60.1 | 187 | 1,259 | 1,486 | 90.8 | 14 |
| Hetero Glucose Chlorella | 3.3 | 5.1 | 3.2 | 1 | 51 | 198 | 6,879 | 7,128 | 86.3 | 11.7 |
| Photo Haematococcus | 6.4 | 18 | 7.6 | 0.028 | 281 | 375 | 8,193 | 8,849 | 88.7 | 11.3 |
| Mixo Haematococcus | 3.8 | 4.3 | 4.2 | 0.17 | 75.8 | 57.7 | 892 | 1,025 | 89.2 | 10.8 |
| Mixo Galdieria | 36 | 19 | 2.5 | 4.5 | 149 | 15.9 | 6,736 | 6,901 | 97 | 12 |
| Hetero Glucose Galdieria | 49 | 27 | 2.1 | 5.4 | 488 | 12.8 | 12,438 | 12,939 | 88.2 | 11.8 |
| Photo Scenedesmus | 11 | 11 | 6.6 | 0.71 | 73.8 | 183 | 9,504 | 9,761 | 89.7 | 10.3 |
| Mixo Acetate Scenedesmus | 4 | 7.9 | 1.3 | 0.84 | 274 | 122 | 4,805 | 5,201 | 88.5 | 11.5 |
| Mixo Glucose Scenedesmus | 2.7 | 9.3 | 1.2 | 0.37 | 133 | 75.5 | 10,408 | 10,616 | 88.5 | 11.5 |
| Hetero Glucose Scenedesmus | 2.8 | 11 | 1.4 | 0.45 | 92.6 | 75.2 | 8,831 | 8,999 | 88.5 | 11.7 |
| Mixo Acetate Chlamydomonas | 3.7 | 4.4 | 5.2 | 0.5 | 487 | 3.08 | 6,241 | 6,731 | 88.5 | 11.5 |
| Photo Chlamydomonas | 3.9 | 6.2 | 5.9 | 0.12 | 240 | 3.52 | 8,667 | 8,911 | 90 | 10 |

TABLE 59

Damage score for plants at termination of experiment
Damage LSMeans Differences Tukey HSD

| Level | | | | Least Sq Mean |
|---|---|---|---|---|
| Veg Only1 | A | | | 2.1000000 |
| Mixo Acetic Chlorella | A | | | 2.1000000 |
| Mixo glucose Galdieria | A | | | 2.1000000 |
| Hetero glucose Chlorella | A | B | | 2.0666667 |
| Hetero glucose Galdieria | A | B | | 2.0666667 |
| Hetero glucose Scenedesmus | A | B | | 2.0666667 |
| Hetero acetic Chlorella | A | B | | 2.0333333 |
| Mixo acetic Haematococcus | A | B | | 2.0333333 |
| Photo Haematococcus | A | B | | 2.0333333 |
| Photo Scenedesmus | A | B | | 2.0333333 |
| Photo Chlorella | A | B | | 2.0000000 |
| Mixo Glucose Chlorella | A | B | | 1.9333333 |
| Veg Only 2 | A | B | | 1.8333333 |
| Mixo Acetate Scenedesmus | A | B | | 1.7666667 |
| HG160303 | | B | | 1.7333333 |
| Mixo Glucose Scenedesmus | | | C | 1.1333333 |

TABLE 60

Dry Weight for plants at termination of experiment
Damage LSMeans Differences Tukey HSD

| Level | | | | Least Sq Mean |
|---|---|---|---|---|
| Mixo Glucose Scenedesmus | A | | | 0.67933333 |
| HG160303 | A | B | | 0.62300000 |

TABLE 60-continued

Dry Weight for plants at termination of experiment
Damage LSMeans Differences Tukey HSD

| Level | | | | Least Sq Mean |
|---|---|---|---|---|
| Mixo Acetate Scenedesmus | A | B | C | 0.59966667 |
| Photo Chlorella | | B | C | D | 0.54066667 |
| Photo Haematococcus | | B | C | D | 0.52166667 |
| Hetero Glucose Galdieria | | B | C | D | 0.50566667 |
| Photo Scenedesmus | | B | C | D | 0.50433333 |
| Mixo acetic Haematococcus | | B | C | D | 0.50233333 |
| Hetero Glucose Scenedesmus | | B | C | D | 0.49866667 |
| Veg Only 2 | | B | C | D | 0.49600000 |
| Mixo Glucose Chlorella | | B | C | D | 0.49566667 |
| Mixo Acetic Chlorella | | | C | D | 0.47600000 |
| Hetero glucose Chlorella | | | | D | 0.44766667 |
| Veg Only 1 | | | | D | 0.43933333 |
| Hetero acetic Chlorella | | | | D | 0.43833333 |
| Mixo Glucose Scenedesmus | | | | D | 0.43100000 |

Example 37 (ADT0059—Hydroponic 2)

Experiments were done to test the effects of microalgae-based compositions administered hydroponically on bell peppers. In these experiments, the biomass for the identified treatments was produced in bag bioreactors (Example 21). Germinated pepper seedlings were grown in 4 inch pots with Turface-a calcined clay substrate. Everyday all plants were fertilized with 150 mL of nutrient solution (i.e., the Veg Only composition) to which various microalgae treatments were added at a concentration of 9 mL/gallon. The trays randomized and location switched within the testing platform on one week schedules. Half of the trays were harvested 22 days after the start of the experiment to collect vegetative growth data. Non-destructive measurements (e.g., height, circumference) were taken on the remaining plants 31 days after the start of the experiment. The remaining plants were harvested 44 days after the start of the experiment to collect additional vegetative growth and yield data.

Control—Veg Only1
Control—Veg Only
Both Veg Only Controls comprise the following nutrients
KH2PO4
KNO3
Ca(NO3)2 4H2O
MgSO4 7H2O
NaFe(III)EDTA
H3HO3
MnC12 4H2O
ZnSO4 7H2O
CuSO4 5H2O
Na2MoO3

Control—PhycoTerra Production Batch # HG160303 (*Chlorella* [HS26] Mixo Acetate produced outdoors in open culture)
*Chlorella* Photo
*Chlorella* Mixo Acetate
*Chlorella* Mixo Glucose
*Chlorella* Hetero Acetate
*Chlorella* Hetero Glucose
*Haematococcus* Photo
*Haematococcus* Mixo Acetate
*Galdieria* Hetero Glucose
*Galdieria* Mixo Glucose
*Scenedesmus* Photo
*Scenedesmus* Mixo Acetate
*Scenedesmus* Mixo Glucose
*Scenedesmus* Hetero Glucose Plant height, plant circumference, plant fresh weight, plant dry weight, bud count and fruit count were observed. Results are shown in Tables 61-67.

TABLE 61

| DAY 22 Treatment | % Difference from Control 1 | | | | % Difference from Control 2 | | | |
|---|---|---|---|---|---|---|---|---|
| | Dia. | Circ. | Height | Bud count | Dia. | Circ. | Height | Bud count |
| Control 1 | | | | | +1.3 | +1.3 | −11.2 | +8.9 |
| Control 2 | −1.3 | −1.3 | +12.6 | −8.2 | | | | |
| Production Batch HG160303 | +4.9 | +4.9 | −1.0 | +5.5 | +6.2 | +6.2 | −12.1 | +14.9 |
| Chlorella Photo | +3.8 | +3.8 | +11.5 | −0.9 | +5.1 | +5.1 | −1.0 | +7.9 |
| Chlorella Mixo Glucose | +0.3 | +0.3 | −2.3 | +5.5 | +1.6 | +1.6 | −13.2 | +14.9 |
| Chlorella Mixo Acetate | −6.8 | −6.8 | +1.5 | +8.2 | −5.6 | −5.6 | −9.9 | +17.8 |
| Chlorella Hetero Glucose | +4.2 | +4.2 | −1.8 | +24.5 | +5.6 | +5.6 | −12.8 | +35.6 |
| Chlorella Hetero Acetate | +4.6 | +4.6 | +12.3 | −6.4 | +5.9 | +5.9 | −0.3 | +2.0 |
| Scenedesmus Photo | +3.8 | +3.8 | +14.8 | −3.6 | +5.2 | +5.2 | +1.9 | +5.0 |
| Scenedesmus Mixo Glucose | +0.3 | +0.3 | +10.8 | 0.0 | +1.6 | +1.6 | −1.6 | +8.9 |
| Scenedesmus Mixo Acetate | +5.1 | +5.1 | −0.1 | +9.1 | +6.4 | +6.4 | −11.2 | +18.8 |
| Scenedesmus Hetero Glucose | +6.3 | +6.3 | +2.0 | +11.8 | +7.6 | +7.6 | −9.4 | +21.8 |
| Haematococcus Photo | −1.1 | −1.1 | −3.6 | −3.6 | +0.2 | +0.2 | −14.4 | +5.0 |
| Haematococcus Mixo Acetate | −2.4 | −2.4 | +14.1 | −5.5 | −1.2 | −1.2 | +1.3 | +3.0 |
| Galdieria Mixo Glucose | +3.0 | +3.0 | +0.9 | +18.2 | +4.3 | +4.3 | −10.4 | +28.7 |
| Galdieria Hetero Glucose | +2.8 | +2.8 | +11.0 | 0.0 | +4.1 | +4.1 | −1.4 | +8.9 |

TABLE 62

| DAY 22 Treatment | % Difference from Control 1 | | | | % Difference from Control 2 | | | |
|---|---|---|---|---|---|---|---|---|
| | Shoot FW | Root FW | Shoot DW | Root DW | Shoot FW | Root FW | Shoot DW | Root DW |
| Control 1 | | | | | +15.8 | +6.5 | +0.2 | −3.7 |
| Control 2 | −13.6 | −6.1 | −0.2 | +3.8 | | | | |
| Production Batch HG160303 | −0.5 | −44.8 | −1.2 | −8.5 | +15.2 | −41.2 | −0.9 | −11.9 |
| Chlorella Photo | +2.3 | −14.0 | +3.4 | +3.0 | +18.5 | −8.4 | +3.6 | −0.8 |
| Chlorella Mixo Glucose | −9.6 | −33.2 | −12.3 | +2.3 | +4.7 | −28.9 | −12.1 | −1.5 |
| Chlorella Mixo Acetate | −2.4 | +15.7 | +17.5 | +23.5 | +13.0 | +23.3 | +17.8 | +19.0 |
| Chlorella Hetero Glucose | −3.1 | −24.0 | −3.0 | −5.1 | +12.2 | −19.1 | −2.7 | −8.6 |
| Chlorella Hetero Acetate | +1.8 | −31.4 | −0.8 | −3.5 | +17.9 | −26.9 | −0.5 | −7.0 |
| Scenedesmus Photo | +8.8 | +18.0 | +22.5 | +31.2 | +26.0 | +25.7 | +22.8 | +26.3 |
| Scenedesmus Mixo Glucose | −6.0 | −20.4 | −4.8 | +2.1 | +8.8 | −15.2 | −4.6 | −1.7 |
| Scenedesmus Mixo Acetate | −10.3 | −34.2 | −3.8 | −4.7 | +3.9 | −29.9 | −3.6 | −8.2 |
| Scenedesmus Hetero Glucose | +0.4 | −1.0 | +0.4 | −11.1 | +16.3 | +5.5 | +0.7 | −14.4 |
| Haematococcus Photo | −12.2 | −36.5 | −9.7 | −6.4 | +1.7 | −33.4 | −9.5 | −9.9 |
| Haematococcus Mixo Acetate | +5.9 | +10.5 | +23.4 | +28.4 | +22.6 | +17.7 | +23.7 | +23.7 |
| Galdieria Mixo Glucose | −8.1 | −11.0 | −4.1 | −3.0 | +6.4 | −5.2 | −3.9 | −6.5 |
| Galdieria Hetero Glucose | +5.3 | −2.4 | +5.9 | +11.3 | +22.0 | +4.0 | +6.1 | +7.2 |

TABLE 63

| DAY 31 Treatment | % Difference from Control 1 | | | % Difference from Control 2 | | |
|---|---|---|---|---|---|---|
| | Dia. | Circ. | Height | Dia. | Circ. | Height |
| Control 1 | | | | −4.7 | −4.7 | −10.3 |
| Control 2 | +4.9 | +4.9 | +11.5 | | | |
| Production Batch HG160303 | −0.9 | −0.9 | +10.2 | −5.5 | −5.5 | −1.1 |
| Chlorella Photo | −1.7 | −1.7 | +5.2 | −6.3 | −6.3 | −5.7 |
| Chlorella Mixo Glucose | −2.6 | −2.6 | −4.8 | −7.1 | −7.1 | −14.6 |
| Chlorella Mixo Acetate | +3.0 | +3.0 | +7.0 | −1.9 | −1.9 | −4.0 |
| Chlorella Hetero Glucose | −4.5 | −4.5 | +1.2 | −9.0 | −9.0 | −9.3 |
| Chlorella Hetero Acetate | +0.1 | +0.1 | +9.1 | −4.6 | −4.6 | −2.1 |
| Scenedesmus Photo | +1.7 | +1.7 | −1.7 | −3.1 | −3.1 | −11.8 |
| Scenedesmus Mixo Glucose | +0.9 | +0.9 | +4.3 | −3.8 | −3.8 | −6.4 |
| Scenedesmus Mixo Acetate | −5.1 | −5.1 | +4.6 | −9.5 | −9.5 | −6.2 |
| Scenedesmus Hetero Glucose | −1.8 | −1.8 | +5.1 | −6.4 | −6.4 | −5.7 |
| Haematococcus Photo | −0.2 | −0.2 | +7.3 | −4.9 | −4.9 | −3.7 |
| Haematococcus Mixo Acetate | +5.3 | +5.3 | +6.1 | +0.4 | +0.4 | −4.9 |
| Galdieria Mixo Glucose | −2.0 | −2.0 | +4.3 | −6.6 | −6.6 | −6.5 |
| Galdieria Hetero Glucose | +3.5 | +3.5 | +0.2 | −1.4 | −1.4 | −10.1 |

TABLE 64

| DAY 44 Treatment | % Difference from Control 1 | | | | % Difference from Control 2 | | | |
|---|---|---|---|---|---|---|---|---|
| | Dia. | Circ. | Height | Bud count | Dia. | Circ. | Height | Bud count |
| Control 1 | | | | | +8.1 | +8.1 | +2.9 | +29.9 |
| Control 2 | −7.5 | −7.5 | −2.9 | −23.0 | | | | |
| Production Batch HG160303 | −4.3 | −4.3 | −14.6 | −10.7 | +3.4 | +3.4 | −12.1 | +16.0 |
| Chlorella Photo | −7.4 | −7.4 | −10.2 | −20.7 | +0.1 | +0.1 | −7.5 | +3.1 |
| Chlorella Mixo Glucose | +0.8 | +0.8 | −10.0 | +2.6 | +8.9 | +8.9 | −7.4 | +33.3 |

TABLE 64-continued

| DAY 44 Treatment | % Difference from Control 1 | | | | % Difference from Control 2 | | | |
| --- | --- | --- | --- | --- | --- | --- | --- | --- |
| | Dia. | Circ. | Height | Bud count | Dia. | Circ. | Height | Bud count |
| Chlorella Mixo Acetate | −5.2 | −5.2 | −4.1 | −12.8 | +2.5 | +2.5 | −1.3 | +13.3 |
| Chlorella Hetero Glucose | −4.1 | −4.1 | +10.2 | +11.1 | +3.6 | +3.6 | +13.5 | +44.4 |
| Chlorella Hetero Acetate | +2.4 | +2.4 | +3.7 | −4.2 | +10.7 | +10.7 | +6.7 | +24.5 |
| Scenedesmus Photo | +1.6 | +1.6 | 0.0 | 0.0 | +9.8 | +9.8 | +2.9 | +29.9 |
| Scenedesmus Mixo Glucose | −2.5 | −2.5 | −.03 | −9.7 | +5.4 | +5.4 | +2.6 | +17.3 |
| Scenedesmus Mixo Acetate | −3.0 | −3.0 | +76 | +6.8 | +4.8 | +4.8 | +10.8 | +38.8 |
| Scenedesmus Hetero Glucose | −2.4 | −2.4 | +7.5 | −6.3 | +5.5 | +5.5 | +10.6 | +21.8 |
| Haematococcus Photo | +0.5 | +0.5 | −1.9 | −1.2 | +8.7 | +8.7 | +1.0 | +28.2 |
| Haematococcus Mixo Acetate | −0.7 | −0.7 | 0.0 | −6.3 | +7.4 | +7.4 | +2.9 | +21.8 |
| Galdieria Mixo Glucose | −0.1 | −0.1 | +12.8 | −9.7 | +8.0 | +8.0 | +16.1 | +17.3 |
| Galdieria Hetero Glucose | −1.4 | −1.4 | −2.5 | −16.0 | +6.6 | +6.6 | +0.3 | +9.2 |

TABLE 65

| DAY 44 Treatment | % Difference from Control 1 | | | | % Difference from Control 2 | | | |
| --- | --- | --- | --- | --- | --- | --- | --- | --- |
| | Flower Count | Micro Fruit | Inter. Fruit | Pepper Count | Flower Count | Micro Fruit | Inter. Fruit | Pepper Count |
| Control 1 | | | | | +53.6 | +51.6 | −50.0 | +50.0 |
| Control 2 | −34.9 | −34.0 | +100 | −33.3 | | | | |
| Production Batch HG160303 | −18.6 | −4.3 | −100 | 0.0 | +25.0 | +45.2 | −100 | +50.0 |
| Chlorella Photo | −43.0 | −21.3 | +200.0 | −12.5 | −12.5 | +19.4 | +50.0 | +31.3 |
| Chlorella Mixo Glucose | −22.1 | −2.1 | +100 | 0.0 | +19.6 | +48.4 | 0.0 | +50.0 |
| Chlorella Mixo Acetate | −18.6 | −27.7 | +200.0 | −22.9 | +25.0 | +9.7 | +50.0 | +15.6 |
| Chlorella Hetero Glucose | −27.6 | −22.0 | +11.1 | −21.3 | +11.1 | +18.3 | −44.4 | +18.1 |
| Chlorella Hetero Acetate | −37.2 | −34.0 | +100.0 | −33.3 | −3.6 | 0.0 | 0.0 | 0.0 |
| Scenedesmus Photo | −19.8 | −44.7 | 0.0 | −39.6 | +23.2 | −16.1 | −50.0 | −9.4 |
| Scenedesmus Mixo Glucose | −45.3 | −8.5 | −100 | −8.3 | −16.1 | +38.7 | −100 | +37.5 |
| Scenedesmus Mixo Acetate | −33.6 | −40.4 | 0.0 | −39.6 | +3.6 | −9.7 | −50.0 | −9.4 |
| Scenedesmus Hetero Glucose | −27.9 | −38.3 | 0.0 | −35.4 | +10.7 | −6.5 | −50.0 | −3.1 |
| Haematococcus Photo | −23.3 | −17.0 | −100 | −16.7 | +17.9 | +25.8 | −100 | +25.0 |
| Haematococcus Mixo Acetate | −26.7 | −51.1 | −100 | −52.1 | +12.5 | −25.8 | −100 | −28.1 |
| Galdieria Mixo Glucose | −25.6 | −2.1 | −100 | −4.2 | +14.3 | +48.4 | −100 | +43.8 |
| Galdieria Hetero Glucose | −37.2 | −36.2 | +100.0 | −35.4 | −3.6 | −3.2 | 0.0 | −3.1 |

TABLE 66

| DAY 44 Treatment | % Difference from Control 1 | | | % Difference from Control 2 | | |
|---|---|---|---|---|---|---|
| | Shoot DW | Root DW | Corrected Root DW | Shoot DW | Root DW | Corrected Root DW |
| Control 1 | | | | +25.2 | −25.4 | −2.9 |
| Control 2 | −20.1 | +34.1 | +2.9 | | | |
| Production Batch HG160303 | −9.1 | +25.9 | +5.2 | +13.9 | −6.1 | +2.2 |
| Chlorella Photo | −21.1 | +23.5 | +9.8 | −1.2 | −7.9 | +6.7 |
| Chlorella Mixo Glucose | +4.6 | +22.4 | +4.2 | +31.0 | −8.7 | +1.2 |
| Chlorella Mixo Acetate | −14.7 | +80.8 | −0.6 | +6.9 | +34.8 | −3.4 |
| Chlorella Hetero Glucose | +1.3 | −5.1 | −0.3 | +26.8 | −29.2 | −3.1 |
| Chlorella Hetero Acetate | −1.5 | +4.1 | +0.3 | +23.3 | −22.4 | −2.6 |
| Scenedesmus Photo | +1.0 | +5.7 | −10.2 | +26.4 | −21.2 | −12.7 |
| Scenedesmus Mixo Glucose | −3.2 | +19.7 | −7.4 | +21.2 | −10.7 | −10.1 |
| Scenedesmus Mixo Acetate | +1.1 | −26.5 | −12.8 | +26.6 | −45.2 | −15.3 |
| Scenedesmus Hetero Glucose | +4.0 | +8.3 | +5.7 | +30.3 | −19.3 | +2.6 |
| Haematococcus Photo | +4.2 | +81.4 | +0.8 | +30.5 | +35.2 | −2.1 |
| Haematococcus Mixo Acetate | −2.9 | +72.3 | +0.3 | +21.6 | +28.5 | −2.6 |
| Galdieria Mixo Glucose | +6.1 | −6.6 | +7.9 | +32.8 | −30.4 | +4.8 |
| Galdieria Hetero Glucose | −15.7 | +7.0 | −20.0 | +5.5 | −20.2 | −22.3 |

TABLE 67

| DAY 44 Treatment | % Difference from Control 1 | | | % Difference from Control 2 | | |
|---|---|---|---|---|---|---|
| | Tray Micro Fruit Count | Tray Int. Fruit Count | Tray Total | Tray Micro Fruit Count | Tray Int. Fruit Count | Tray Total |
| Control 1 | | | | +51.6 | −50.0 | +45.5 |
| Control 2 | −34.0 | +100.0 | −31.2 | | | |
| Production Batch HG160303 | −4.3 | −100 | 0.0 | +45.2 | −100 | +45.5 |
| Chlorella Photo | −21.3 | +200.0 | −12.5 | +19.4 | +50.0 | +27.3 |
| Chlorella Mixo Glucose | −2.1 | +100.0 | 0.0 | +48.4 | 0.0 | +45.5 |
| Chlorella Mixo Acetate | −27.7 | +200.0 | −22.9 | +9.7 | +50.0 | +12.1 |
| Chlorella Hetero Glucose | −29.8 | 0.0 | −29.2 | +6.5 | −50.0 | +3.0 |
| Chlorella Hetero Acetate | −34.0 | +100 | −31.2 | 0.0 | 0.0 | 0.0 |
| Scenedesmus Photo | −44.7 | 0.0 | −39.6 | −16.1 | −50.0 | −12.1 |
| Scenedesmus Mixo Glucose | −8.5 | −100 | −8.3 | +38.7 | −100 | +33.3 |
| Scenedesmus Mixo Acetate | −40.4 | 0.0 | −39.6 | −9.7 | −50.0 | −12.1 |
| Scenedesmus Hetero Glucose | −38.3 | 0.0 | −35.4 | −6.5 | −50.0 | −6.1 |
| Haematococcus Photo | −17.0 | −100 | −16.7 | +25.8 | −100 | +21.2 |
| Haematococcus Mixo Acetate | −51.1 | −100 | −52.1 | −25.8 | −100 | −30.3 |
| Galdieria Mixo Glucose | −2.1 | −100 | −4.2 | +48.4 | −100 | +39.4 |
| Galdieria Hetero Glucose | −36.2 | +100.0 | −33.3 | −3.2 | 0.0 | −3.0 |

Example 38

Below is a table of Micronutrient analysis of microalgal biomass used in treatments (questionable values are shaded).

TABLE 68

| Titmnt | pH (SU) | Chloride, Cl (ppm) | Phosphorus, P2O5 (%) | Potassium, K2O (%) | Calcium, Ca (%) | Magnesium, Mg (%) | Sodium, Na (%) | Sulfur, S (%) | Iron, Fe (ppm) |
|---|---|---|---|---|---|---|---|---|---|
| Veg Only | 5.9 | 7.74 | 0.0072 | 0.019 | 0.016 | 0.0052 | 0.0012 | 0.0067 | 2.2 |
| HG160303 | 3.0 | 141 | 0.86 | 0.16 | 0.045 | 0.017 | 0.052 | 0.047 | 29 |
| Photo Chlorella | 3.8 | 66 | 0.82 | 0.27 | 0.045 | 0.042 | 0.037 | 0.067 | 38 |
| Mixo Acetate Chlorella | 3.8 | 34 | 0.25 | 0.13 | 0.031 | 0.0083 | 0.022 | 0.005 | 45 |
| Mixo Glucose Chlorella | 3.8 | 123 | 0.68 | 0.21 | 0.038 | 0.022 | 0.065 | 0.036 | 18 |

TABLE 68-continued

| | | | | | | | | | |
|---|---|---|---|---|---|---|---|---|---|
| Hetero Acetate Chlorella | 3.8 | 111 | 0.4 | 0.14 | 0.036 | 0.017 | 0.061 | 0.039 | 22 |
| Hetero Glucose Chlorella | 3.9 | 90 | 0.8 | 0.29 | 0.037 | 0.028 | 0.093 | 0.068 | 23 |
| Photo Haematococcus | 4.0 | 85 | 0.9 | 0.25 | 0.041 | 0.048 | 0.0093 | 0.054 | 52 |
| Mixo Haematococcus | 4.2 | 133 | 0.63 | 0.21 | 0.033 | 0.029 | 0.015 | 0.05 | 19 |
| Mixo Galdieria | 3.9 | 246 | 0.36 | 0.11 | 0.028 | 0.013 | 0.047 | 0.026 | 62 |
| Hetero Glucose Galdieria | 3.8 | 208 | 0.72 | 0.14 | 0.032 | 0.027 | 0.04 | 0.068 | 45 |
| Photo Scenedesmus | 4.1 | 55 | 0.82 | 0.25 | 0.031 | 0.038 | 0.036 | 0.059 | 36 |
| Mixo Acetate Scenedesmus | 4.0 | 147 | 0.73 | 0.16 | 0.029 | 0.026 | 0.049 | 0.057 | 42 |
| Mixo Glucose scenedesmus | 3.8 | 159 | 0.6 | 0.18 | 0.028 | 0.019 | 0.031 | 0.04 | 25 |
| Hetero Gluose Scenedesmus | 3.8 | 47 | 0.63 | 0.19 | 0.028 | 0.017 | 0.029 | 0.04 | 22 |
| Mixo Acetate Chlamydomonas | 3.5 | 66 | 0.95 | 0.14 | 0.038 | 0.027 | 0.031 | 0.057 | 27 |
| Photo Chlamydomonas | 3.7 | 93 | 0.93 | 0.13 | 0.077 | 0.042 | 0.012 | 0.056 | 34 |

| Titmnt | Zinc, Zn (ppm) | Manganese, Mn (ppm) | Copper, Cu (ppm) | Boron, B (ppm) | Insoluble Nitrogen (ppm) | Total Nitrogen, N (ppm) | Moisture (%) | Dry Matter (%) |
|---|---|---|---|---|---|---|---|---|
| Veg Only | 0.46 | 0.26 | 0.026 | 0.61 | 811 | 1,034 | 99.9 | 0.1 |
| HG160303 | 1.5 | 3.0 | 1.2 | 0.77 | 4,448 | 4,823 | 88.2 | 11.8 |
| Photo Chlorella | 6.0 | 13 | 2.7 | 0.62 | 6,830 | 7,115 | 88.8 | 11.2 |
| Mixo Acetate Chlorella | 1.1 | 1.2 | 1.2 | 0.39 | 2,415 | 2,583 | 95.2 | 11.3 |
| Mixo Glucose Chlorella | 3.2 | 12 | 1.9 | 1.2 | 9,249 | 9,301 | 89.1 | 10.9 |
| Hetero Acetate Chlorella | 3.5 | 9.6 | 1.8 | 1.0 | 1,259 | 1,486 | 90.8 | 14 |
| Hetero Glucose Chlorella | 3.3 | 5.1 | 3.2 | 1.0 | 6,879 | 7,128 | 86.3 | 11.7 |
| Photo Haematococcus | 6.4 | 18 | 7.6 | 0.028 | 8,193 | 8,849 | 88.7 | 11.3 |
| Mixo Haematococcus | 3.8 | 4.3 | 4.2 | 0.17 | 892 | 1,025 | 89.2 | 10.8 |
| Mixo Galdieria | 36 | 19 | 2.5 | 4.5 | 6,736 | 6,901 | 97.0 | 12.0 |
| Hetero Glucose Galdieria | 49 | 27 | 2.1 | 5.4 | 12,438 | 12,939 | 88.2 | 11.8 |
| Photo Scenedesmus | 11 | 11 | 6.6 | 0.71 | 9,504 | 9,761 | 89.7 | 10.3 |
| Mixo Acetate Scenedesmus | 4.0 | 7.9 | 1.3 | 0.84 | 4,805 | 5,201 | 88.5 | 11.5 |
| Mixo Glucose scenedesmus | 2.7 | 9.3 | 1.2 | 0.37 | 10,408 | 10,616 | 88.5 | 11.5 |
| Hetero Gluose Scenedesmus | 2.8 | 11 | 1.4 | 0.45 | 8,831 | 8,999 | 88.3 | 11.7 |
| Mixo Acetate Chlamydomonas | 3.7 | 4.4 | 5.2 | 0.50 | 6,241 | 6,731 | 88.5 | 11.5 |
| Photo Chlamydomonas | 3.9 | 6.2 | 5.9 | 0.12 | 8,667 | 8,911 | 90.0 | 10.0 |

Figure 3:
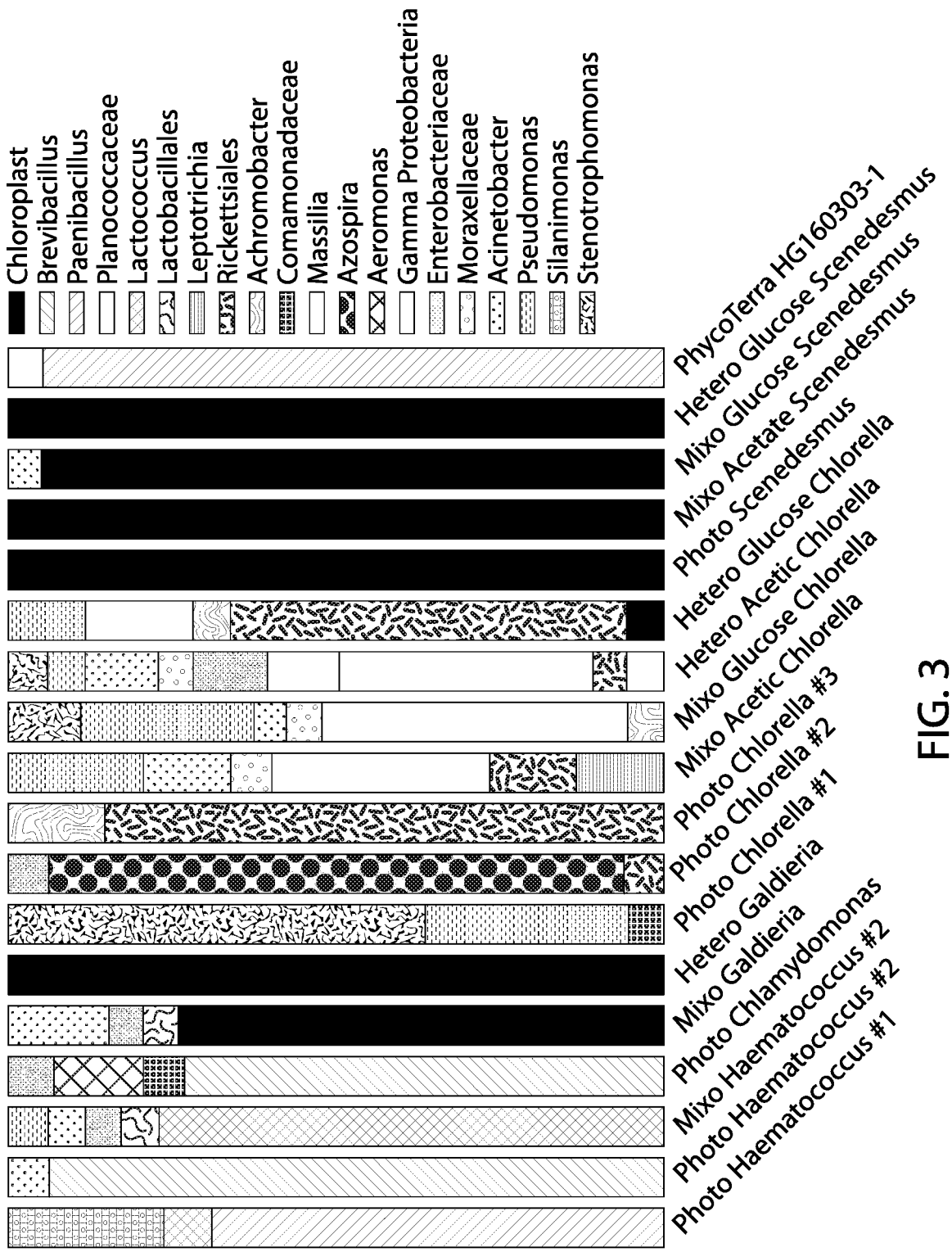
FIG. 3 depicts a composition analyses of example microalgae-based compositions.

Results of analyses of phytohormone and bacterial communities in an example of the composition are provided in Table 69 and FIG. 3.

TABLE 69

| Treatment | Phytohormone | Concentration (ng/g FW) |
|---|---|---|
| HG160303 | c-Z | 8.7 |
| | c-ZR | 0.6 |
| | IAA | 21.1 |
| | t-ABA | . |
| | t-ZR | 0.2 |
| | iP | 6 |
| | iPR | 0.5 |
| Chlorella HA | c-Z | 0.1 |
| | c-ZR | 41.3 |
| | IAA | . |
| | t-ABA | . |
| | t-ZR | 1.1 |
| | iP | 0.1 |
| | iPR | 25 |
| Chlorella HG | c-Z | . |
| | c-ZR | 15.6 |
| | IAA | 3.9 |
| | t-ABA | . |
| | t-ZR | 3.4 |

TABLE 69-continued

| Treatment | Phytohormone | Concentration (ng/g FW) |
|---|---|---|
| | iP | . |
| | iPR | 3 |
| Chlorella MA | c-Z | . |
| | c-ZR | 0.8 |
| | IAA | 1.3 |
| | t-ABA | . |
| | t-ZR | . |
| | iP | . |
| | iPR | 0.2 |
| Chlorella MG | c-Z | . |
| | c-ZR | 34.7 |
| | IAA | 5.7 |
| | t-ABA | . |
| | t-ZR | 2.6 |
| | iP | . |
| | iPR | 32.1 |
| Chlorella Photo | c-Z | . |
| | c-ZR | 0.9 |
| | IAA | 9.9 |
| | t-ABA | . |
| | t-ZR | 0.3 |
| | iP | . |
| | iPR | 0.5 |

TABLE 69-continued

| Treatment | Phytohormone | Concentration (ng/g FW) |
|---|---|---|
| Galdi HG | c-Z | . |
| | c-ZR | . |
| | IAA | 10.7 |
| | t-ABA | . |
| | t-ZR | . |
| | iP | 3.9 |
| | iPR | 18.8 |
| Galdi MG | c-Z | . |
| | c-ZR | . |
| | IAA | 16.5 |
| | t-ABA | . |
| | t-ZR | . |
| | iP | 1.7 |
| | iPR | 6.9 |
| Haemy MA | c-Z | 0.8 |
| | c-ZR | 7.1 |
| | IAA | 96.4 |
| | t-ABA | . |
| | t-ZR | 0.2 |
| | iP | 0.8 |
| | iPR | 3.4 |
| Haemy Photo | c-Z | 11 |
| | c-ZR | 1.1 |
| | IAA | 1830.8 |
| | t-ABA | 0.4 |
| | t-ZR | . |
| | iP | 18 |
| | iPR | 2.2 |
| Scen HG | c-Z | 1.7 |
| | c-ZR | 4.6 |
| | IAA | 5.2 |
| | t-ABA | . |
| | t-ZR | . |
| | iP | 0.6 |
| | iPR | 0.6 |
| Scen MA | c-Z | 7.5 |
| | c-ZR | 12.5 |
| | IAA | 12.4 |
| | t-ABA | 0.4 |
| | t-ZR | 0.4 |
| | iP | 4.6 |
| | iPR | 1.5 |
| Scen MG | c-Z | 2.1 |
| | c-ZR | 27.6 |
| | IAA | 2 |
| | t-ABA | . |
| | t-ZR | 2 |
| | iP | 0.6 |
| | iPR | 2.5 |
| Scen Photo | c-Z | 0.7 |
| | c-ZR | 4.8 |
| | IAA | 6.7 |
| | t-ABA | 0.8 |
| | t-ZR | 0.4 |
| | iP | 0.5 |
| | iPR | 2.2 |

It will be apparent to one skilled in the art that varying substitutions and modifications can be made to the invention disclosed herein without departing from the scope and spirit of the invention.

Those skilled in the art recognize that the aspects and embodiments of the invention set forth herein can be practiced separate from each other or in conjunction with each other. Therefore, combinations of separate embodiments are within the scope of the invention as disclosed herein.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method of plant enhancement comprising administering to a plant, seedling, or seed a composition comprising 0.001-0.1% by weight of microalgae biomass to enhance at least one plant characteristic, wherein the microalgae biomass is pasteurized, and the microalgae comprise at least one from the group consisting of *Spirulina*, *Isochrysis*, and *Scenedesmus*.

2. The method of claim 1, wherein the composition is applied when the plant is under at least one of salt stress and temperature stress conditions.

3. The method of claim 1, wherein the microalgae biomass has been subjected to a protein extraction process.

4. The method of claim 1, wherein the microalgae biomass comprises whole microalgae biomass.

5. The method of claim 1, wherein the microalgae comprise *Isochrysis*.

6. The method of claim 1, wherein the microalgae biomass comprises whole microalgae biomass, oil extracted from the microalgae biomass, or extracted microalgae biomass from which oil has been removed.

7. The method of claim 6, wherein the microalgae biomass comprises oil extracted from the microalgae biomass.

8. The method of claim 7, wherein the oil is extracted from the microalgae biomass with ethanol, hexane, or acetone.

9. The method of claim 1, wherein the at least one plant characteristic is selected from the group consisting of seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sunburn.

10. The method of claim 9, wherein the at least one plant characteristic is plant fresh weight or plant dry weight.

11. The method of claim 9, wherein the at least one plant characteristic is root length or root mass.

12. The method of claim 9, wherein the at least one plant characteristic is fruit production or fruit quality.

13. The method of claim 1, wherein the microalgae comprise *Scenedesmus*.

14. The method of claim 1, wherein the microalgae comprise *Spirulina*.

15. A method of plant enhancement comprising administering to a plant, seedling, or seed a composition comprising of 0.001-0.1% by weight of extracted microalgae protein to enhance at least one plant characteristic, wherein the extracted microalgae protein is pasteurized, and the microalgae comprise at least one from the group consisting of *Spirulina, Isochrysis*, and *Scenedesmus*.

16. The method of claim 15, wherein the composition is applied when the plant is under at least one of salt stress and temperature stress conditions.

17. The method of claim 15, wherein the microalgae comprise *Spirulina*.

18. The method of claim 15, wherein the microalgae comprise *Scenedesmus*.

* * * * *